(12) United States Patent  
Swanson et al.

(10) Patent No.: US 11,759,784 B2
(45) Date of Patent: Sep. 19, 2023

(54) REAGENT CARTRIDGE

(71) Applicant: Precision Planting LLC, Tremont, IL (US)

(72) Inventors: Todd Swanson, Morton, IL (US); Dale Koch, Tremont, IL (US)

(73) Assignee: Precision Planting LLC, Tremont, IL (US)

( * ) Notice: Subject to any disclaimer, the term of this patent is extended or adjusted under 35 U.S.C. 154(b) by 267 days.

(21) Appl. No.: 17/040,040

(22) PCT Filed: Mar. 19, 2019

(86) PCT No.: PCT/US2019/022982
§ 371 (c)(1),
(2) Date: Sep. 21, 2020

(87) PCT Pub. No.: WO2019/183103
PCT Pub. Date: Sep. 26, 2019

(65) Prior Publication Data
US 2021/0016286 A1  Jan. 21, 2021

Related U.S. Application Data

(60) Provisional application No. 62/646,177, filed on Mar. 21, 2018.

(51) Int. Cl.
*B01L 1/00* (2006.01)
*B01L 3/00* (2006.01)
(Continued)

(52) U.S. Cl.
CPC ............... *B01L 3/527* (2013.01); *G01N 1/04* (2013.01); *G01N 1/4055* (2013.01);
(Continued)

(58) Field of Classification Search
None
See application file for complete search history.

(56) References Cited

U.S. PATENT DOCUMENTS 9,645,143 B2 *  5/2017  Holmes ............. G01N 35/1065
2002/0138201 A1  9/2002  Greensides
(Continued)

FOREIGN PATENT DOCUMENTS

GB  2532780 A  1/2015
GB  2532780 A  6/2016
(Continued)

OTHER PUBLICATIONS

USPTO WIPO Recieving Office, International Search Report for International Application No. PCT/US2019/022982, dated Jun. 17, 2019.
(Continued)

Primary Examiner — Jyoti Nagpaul

(57) ABSTRACT

In one embodiment, a cartridge includes at least one compartment and a reagent in the at least one compartment. The reagent is a chemical composition for testing at least one of soil and vegetation for a chemical contained in the soil or vegetation. The reagent can be used in a soil and/or vegetation analysis test. The cartridge can contain an authentication chip to ensure that the reagent is the correct reagent for the analysis test.

30 Claims, 47 Drawing Sheets

(51) Int. Cl.
*G01N 1/04* (2006.01)
*G01N 1/40* (2006.01)
*G01N 35/00* (2006.01)

(52) U.S. Cl.
CPC .. *G01N 35/00029* (2013.01); *B01L 2200/143* (2013.01); *B01L 2200/16* (2013.01); *B01L 2300/023* (2013.01); *B01L 2300/0803* (2013.01); *B01L 2300/123* (2013.01); *G01N 2001/4061* (2013.01); *G01N 2035/00188* (2013.01)

(56) References Cited

U.S. PATENT DOCUMENTS

| | | | |
|---|---|---|---|
| 2005/0194316 A1* | 9/2005 | Pourahmadi | B01L 3/502753 436/178 |
| 2010/0037712 A1* | 2/2010 | Burton | E21B 49/02 53/284.7 |
| 2010/0262380 A1 | 10/2010 | Matievich, Jr. et al. | |
| 2016/0184826 A1* | 6/2016 | Nemoto | B01L 3/527 436/66 |

FOREIGN PATENT DOCUMENTS

| | | |
|---|---|---|
| WO | 9853312 A1 | 11/1988 |
| WO | 98/53312 A1 | 11/1998 |
| WO | 2009/076244 A1 | 6/2009 |

OTHER PUBLICATIONS

European Patent Office, International Search Report related to International Patent Application No. PCT/US2019022982, dated Nov. 15, 2021.

CCPIT Patent and Trademark Law Office, Search Report related to Chinese Application for Invention No. 201980020148.2, dated Oct. 19, 2022.

* cited by examiner

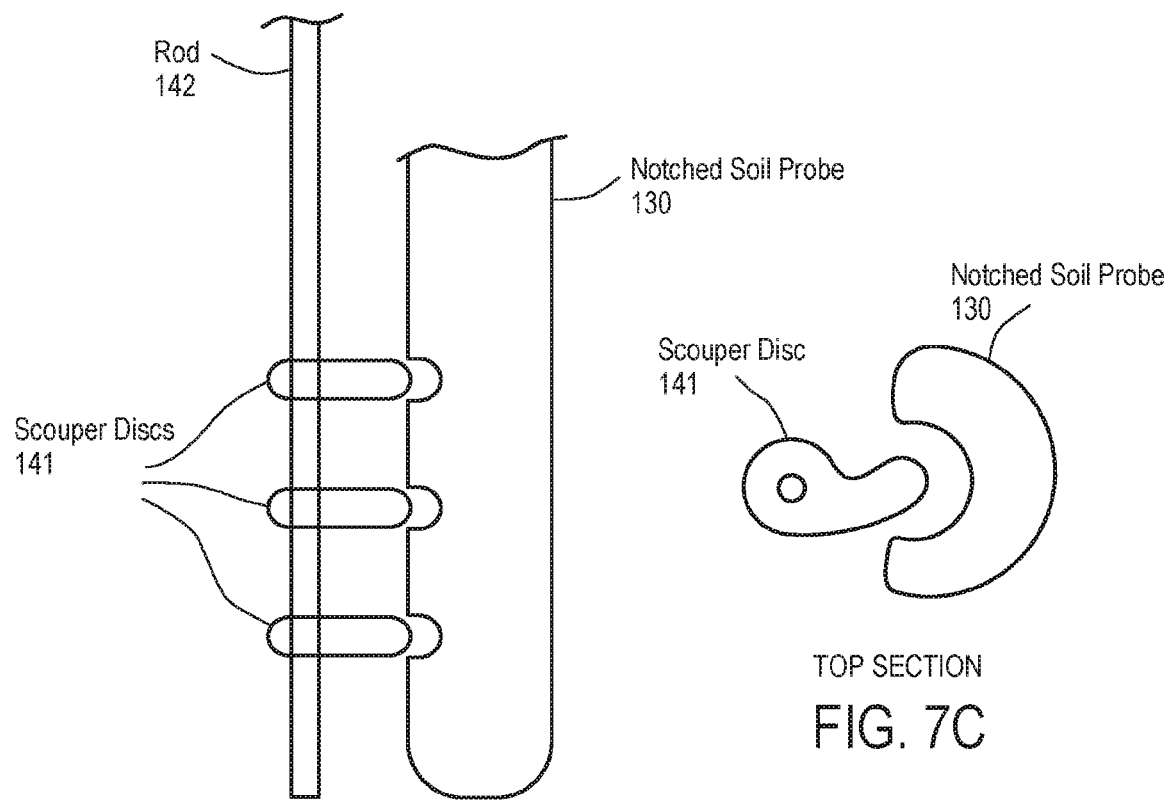
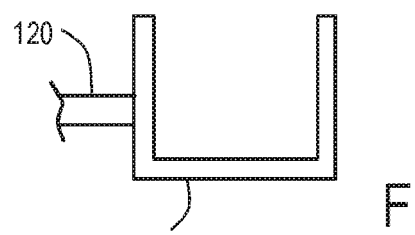
FIG. 7B
FIG. 7C
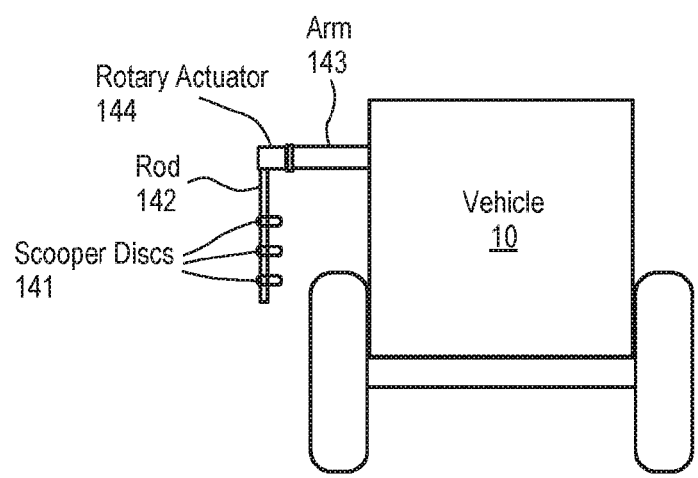
FIG. 7D

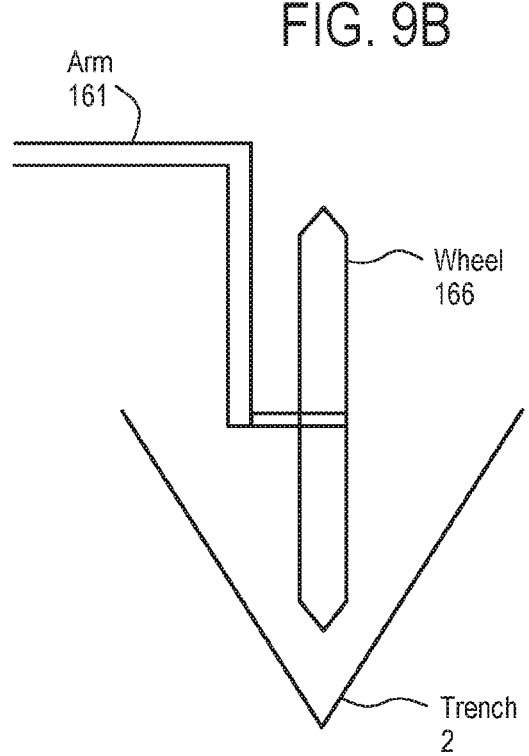

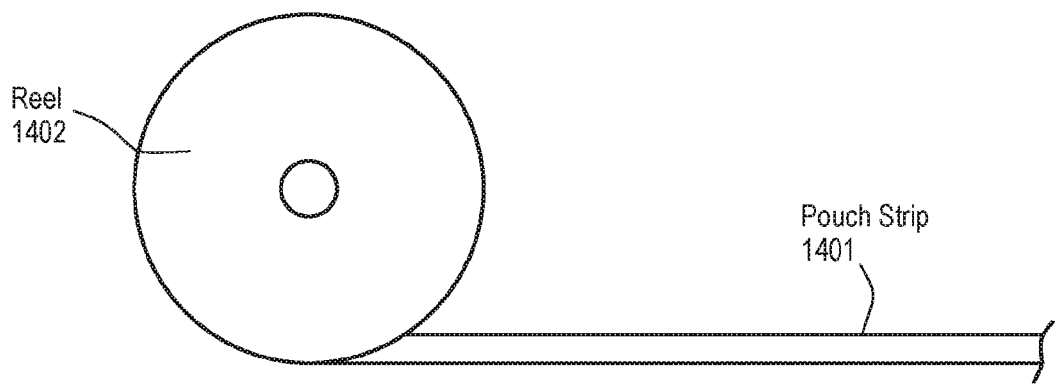
FIG. 24A
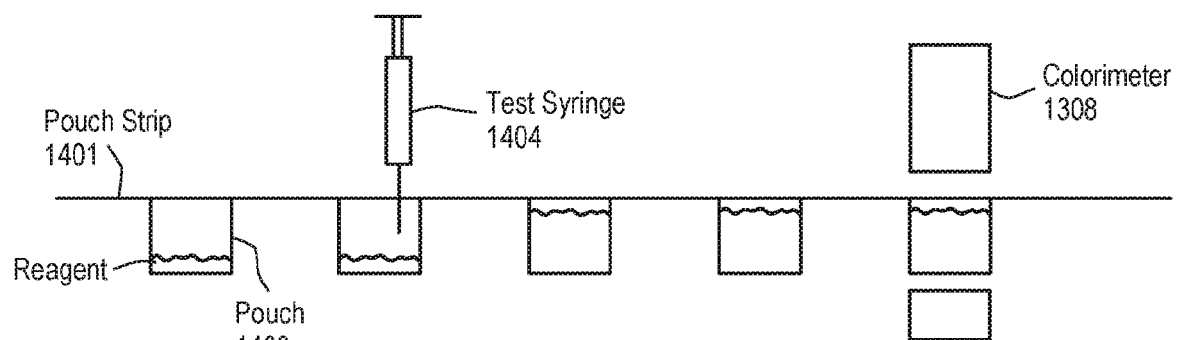
FIG. 24B
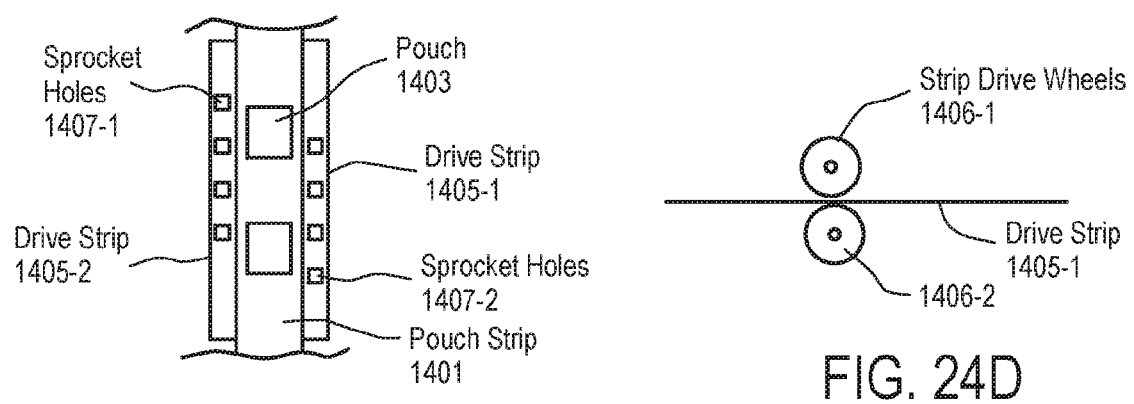
FIG. 24C
FIG. 24D
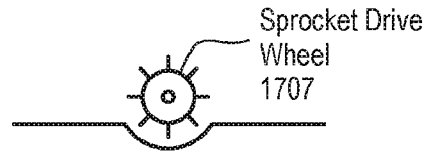
FIG. 24E

SIDE VIEW

REAGENT CARTRIDGE

RELATED APPLICATIONS

This application claims the benefit of U.S. Provisional Application No. 62/646,177 filed on Mar. 21, 2018 entitled: REAGENT CARTRIDGE, the entire contents of which are incorporated by reference herein.

TECHNICAL FIELD

Embodiments of the present disclosure relate to cartridges containing reagents.

BACKGROUND

Cartridges can be created that contain one or more reagents that can be used in a chemical analysis of a sample. For a given chemical analysis, there will be one reagent having a specific chemical composition that can be used in the chemical analysis that will provide accurate results.

Changing a concentration of a chemical in the reagent or having one or more impurities in the reagent will affect the validity of the chemical analysis. Impurities could react with a test sample and change the test results. Having an invalid analysis will lead a person to take an inappropriate action based on the invalid analysis. For example, if testing soil for a nutrient, and the nutrient level is not correctly measured, a person could apply an incorrect amount of the nutrient to soil. This could either be too little, which would result in plants being under nourished. Or, this could be too much, which could result in too much nutrient, which could harm or kill a plant, or result in waste of the nutrient and added cost.

It is critical to ensure that a chemical analysis is conducted with the correct reagent for the chemical analysis.

BRIEF DESCRIPTION OF THE DRAWINGS

The present disclosure is illustrated by way of example, and not by way of limitation, in the figures of the accompanying drawings and in which:

FIG. 7B is side elevation view of the soil probe of FIG. 7A with rod with scooper discs according to one embodiment.

FIG. 7C is a top sectional view of the soil probe of FIG. 7B with the scooper disc according to one embodiment.

FIG. 7D is a front elevation view of the soil probe and rod with scooper discs of FIG. 7B on a vehicle according to one embodiment.

FIG. 9B is a rear elevation view of an alternative disc for FIG. 9A according to one embodiment.

FIG. 24A is a side elevation view of a pouch strip according to one embodiment.

FIG. 24B is a top elevation view of the pouch strip of FIG. 24A according to one embodiment.

FIG. 24C is a top elevation view of the pouch strip of FIG. 24A and drive strips according to one embodiment.

FIG. 24D is a side elevation view of drive wheels for the pouch strip of FIG. 24A.

FIG. 24E is a side elevation view of a sprocket drive wheel 1707 for the pouch strip of FIG. 24B.

BRIEF SUMMARY

A reagent cartridge with at least one chamber contains at least one reagent.

DETAILED DESCRIPTION

All references cited herein are hereby incorporated by reference in their entireties. In the event of a conflict in a definition in the present disclosure and that of a cited reference, the present disclosure controls.

Described herein are implements for sensing and/or testing soil and/or vegetation. As described more fully below, sensing is measuring a property of soil and/or vegetation without taking a sample of the soil and/or vegetation for testing.

Examples of sensing include, but are not limited to, spectrographic measurement, electrical conductivity, apparent electrical conductivity, LIDAR, radar, ground penetrating radar, sonar, optical height, camera, time of flight camera. Examples of spectrographic measurement include, but are not limited to, visible light, laser, near-infrared, mid-infrared, infrared, transient infrared spectroscopy, RAMAN spectroscopy, ultraviolet, and x-ray.

Figure 1:
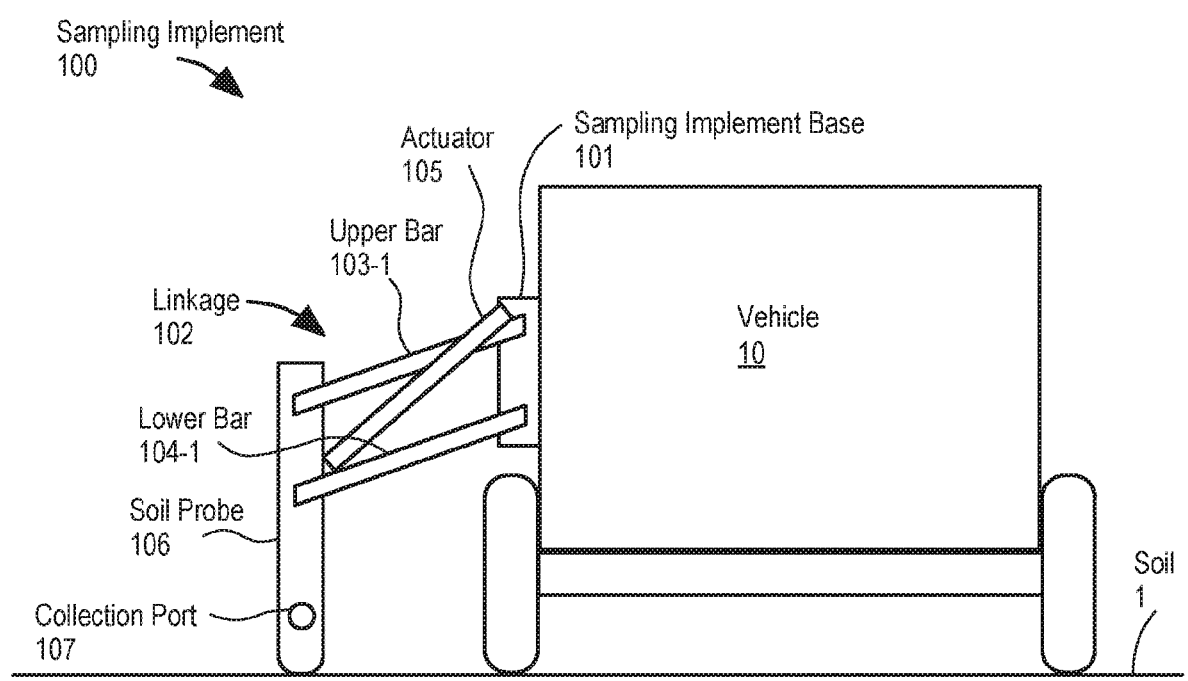
FIG. 1 is a front elevation view of a soil probe on a vehicle according to one embodiment.
Figure 2:
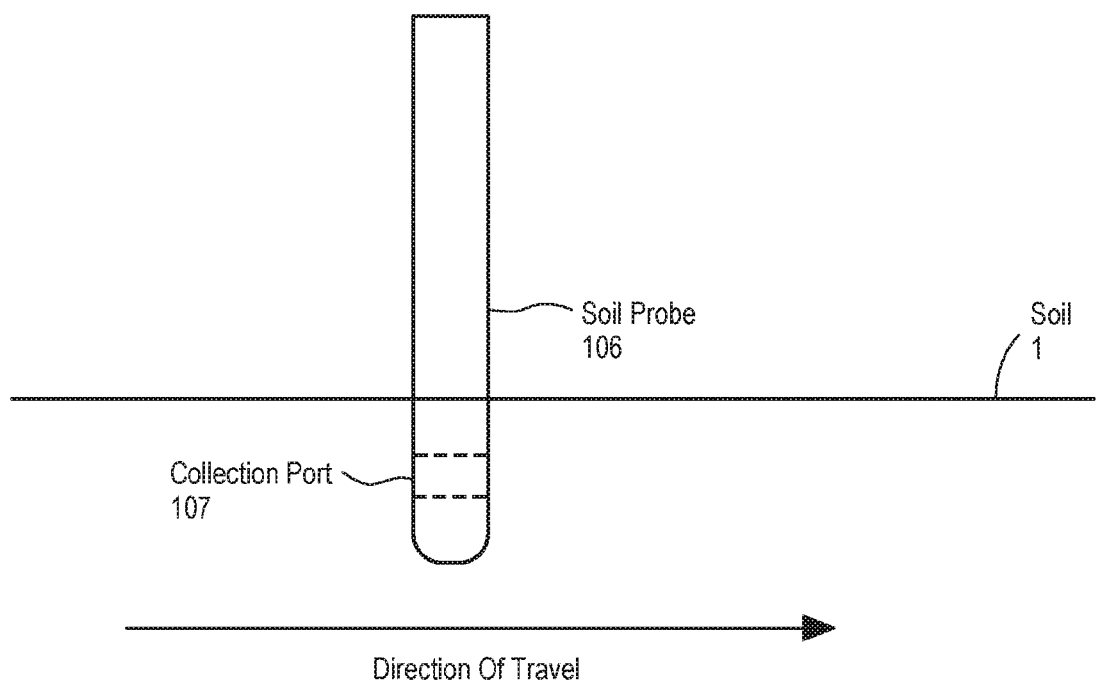
FIG. 2 is a side elevation view of the soil probe from FIG. 1.
Figure 3:
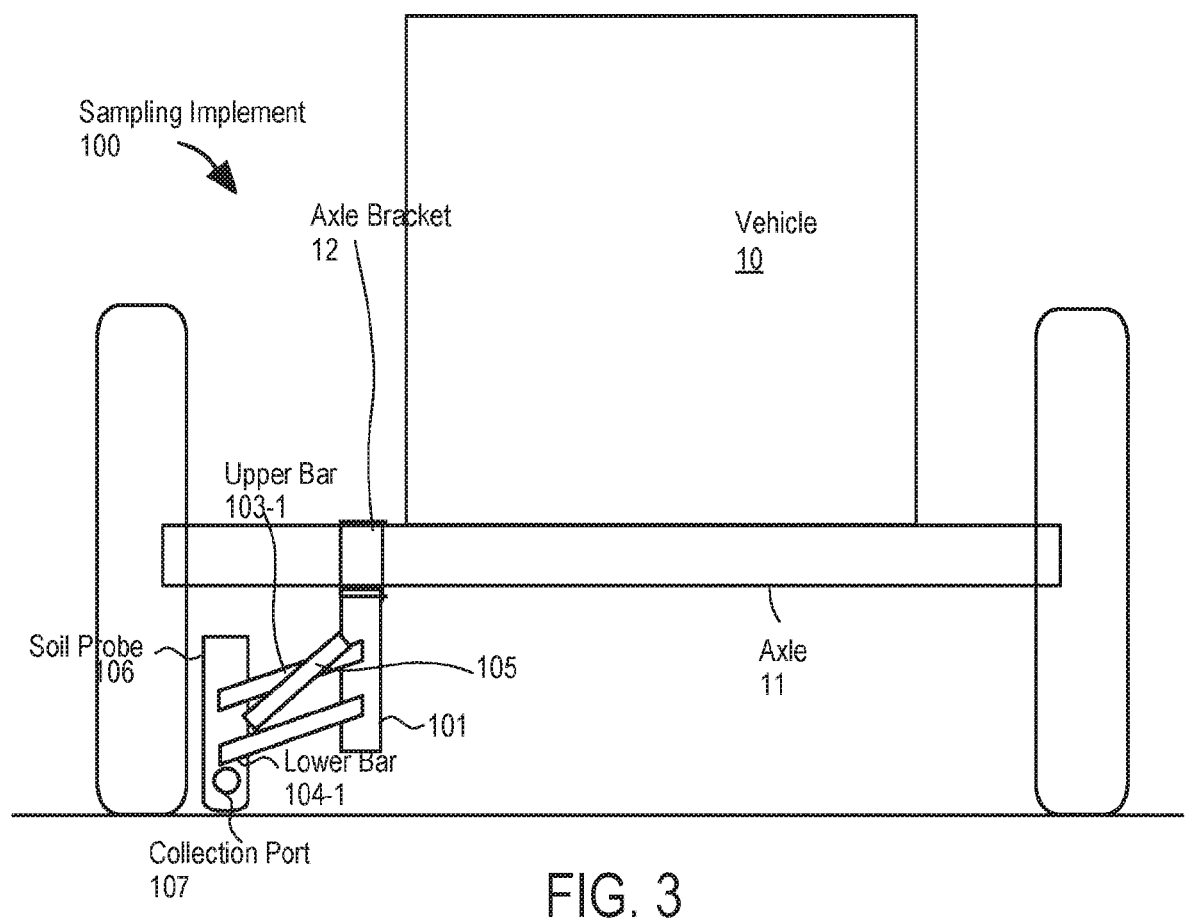
FIG. 3 is a front elevation view of a soil probe mounted to an axle according to one embodiment.
Figure 4:
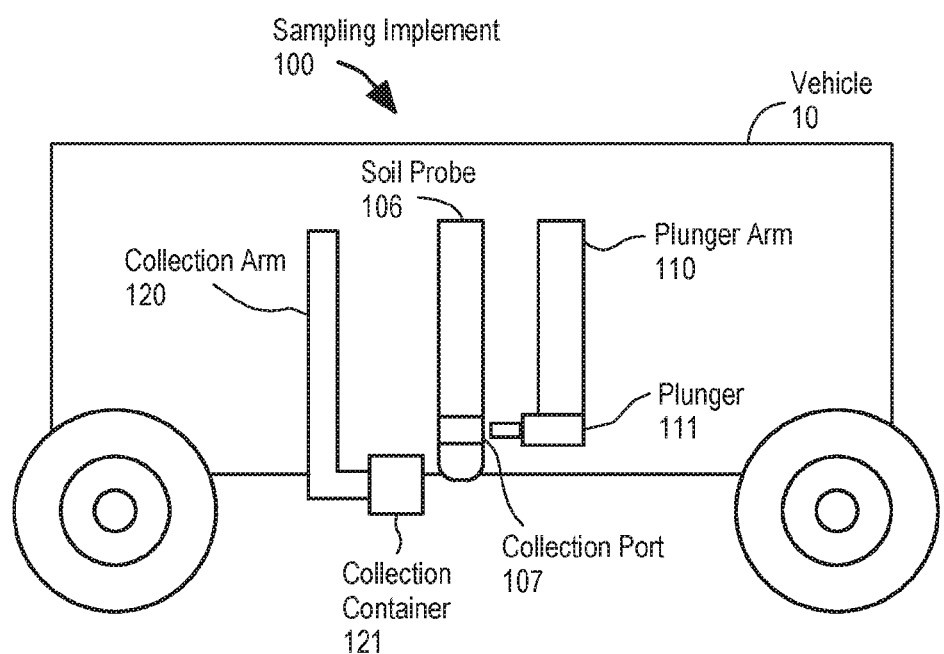
FIG. 4 is a side elevation view of a soil probe on a vehicle according to one embodiment.
Figure 5:
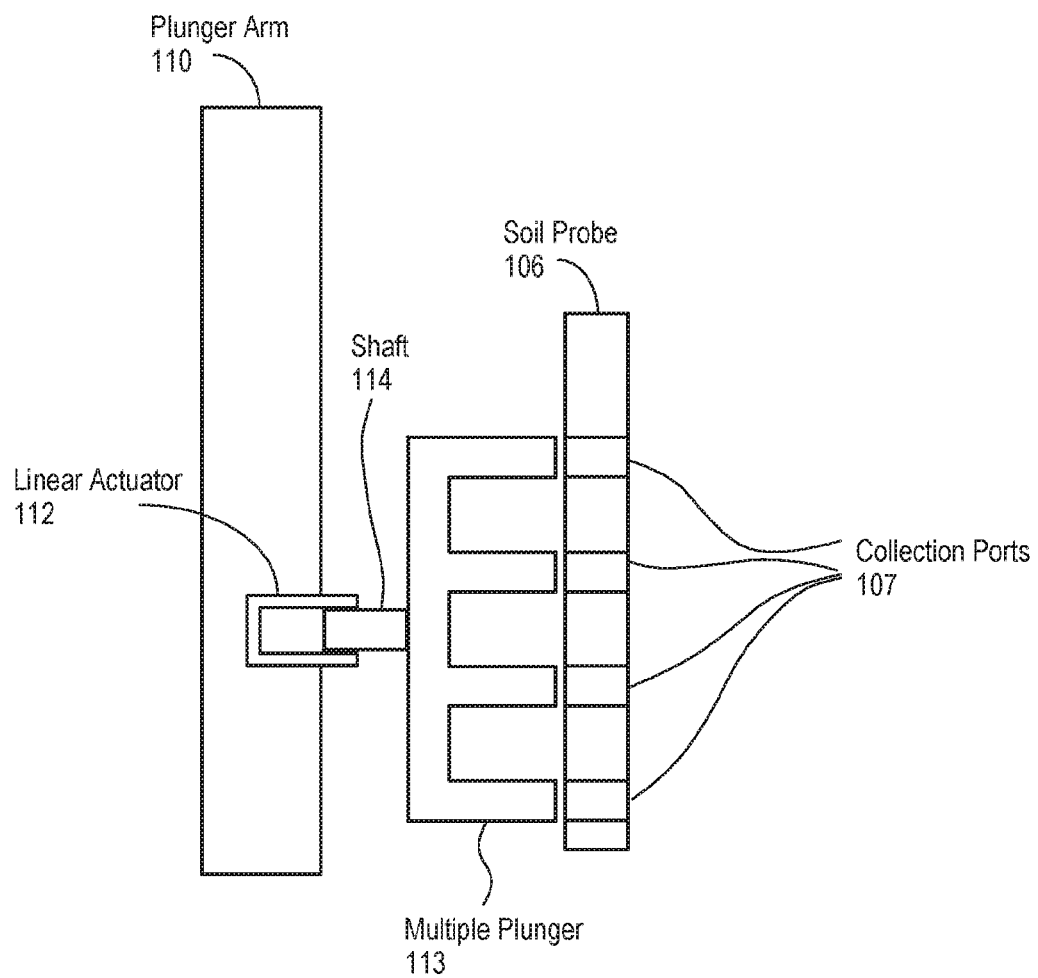
FIG. 5 is a side elevation view of a soil probe and multiple plunger according to one embodiment.
Figure 6:
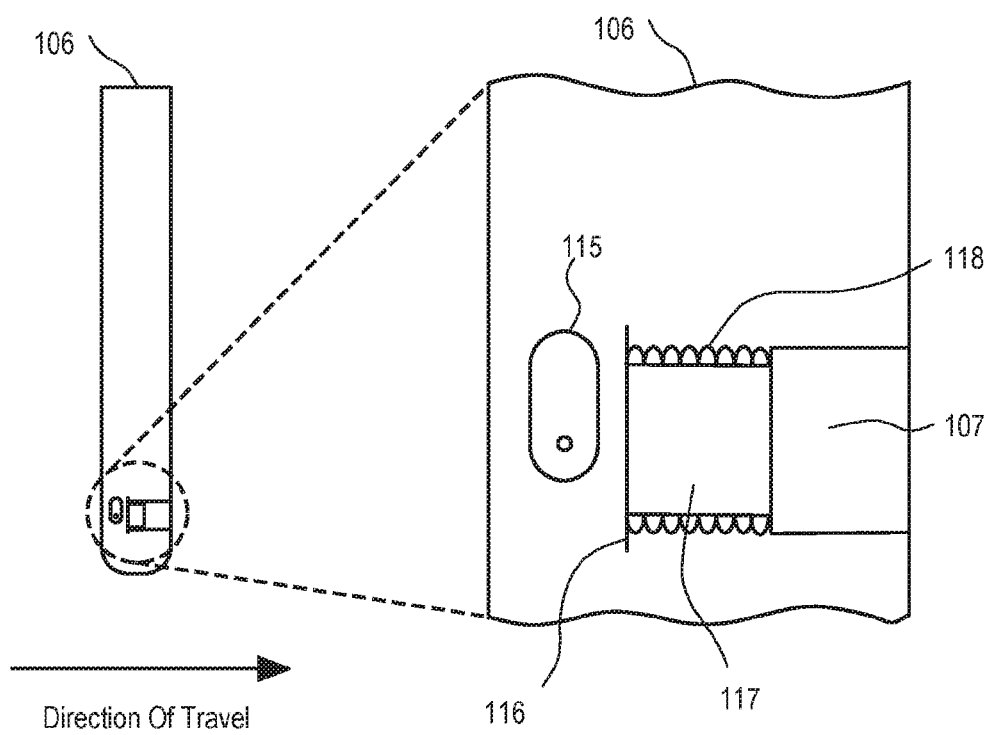
FIG. 6 is a side sectional view of a soil probe according to one embodiment.
Figure 7A:
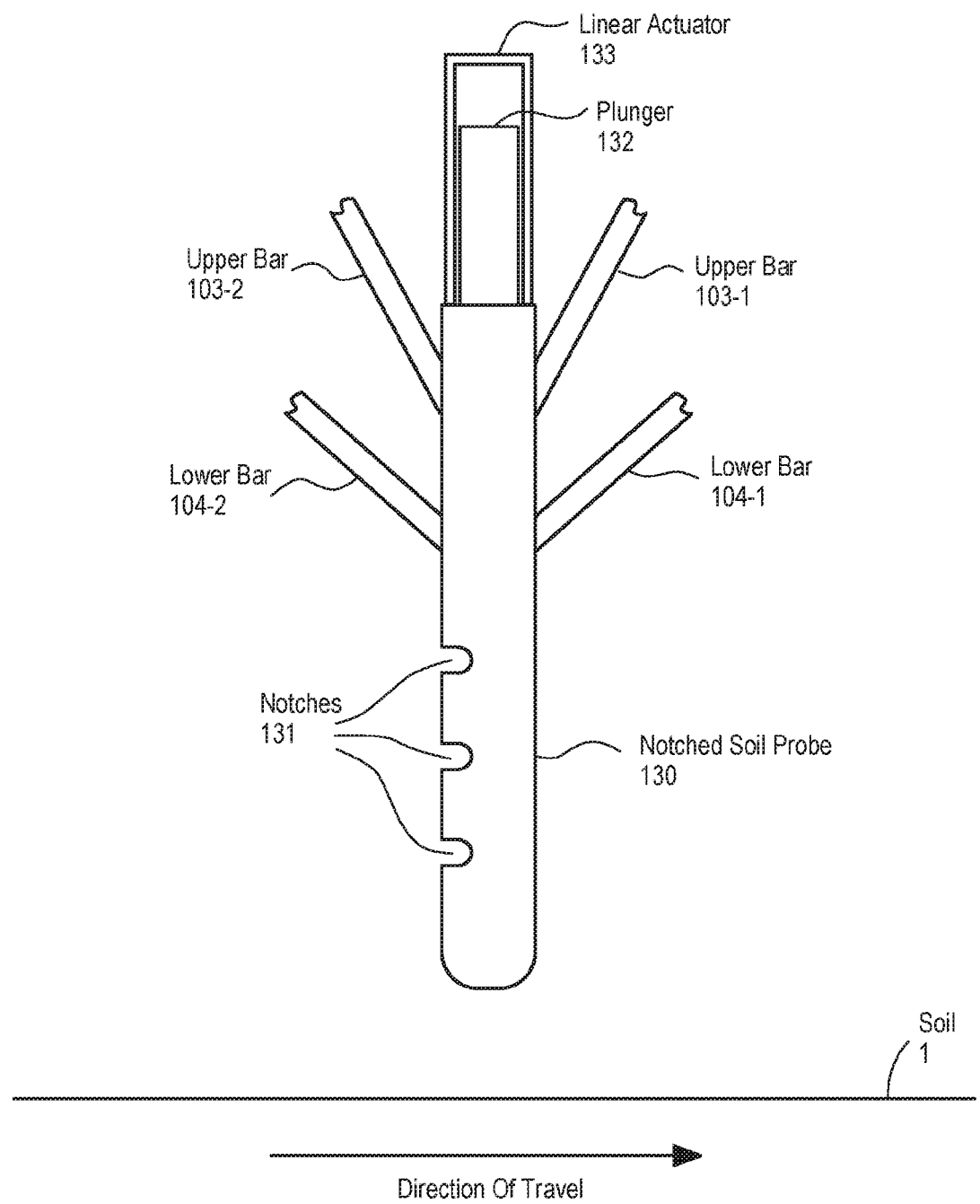
FIG. 7A is a side elevation view of a soil probe according to one embodiment.

In one embodiment, an agricultural implement 5 includes a vehicle 10 for moving across a field. The vehicle 10 can be any vehicle. In one embodiment, the vehicle 10 is an agricultural vehicle that performs at least one agricultural function including, but not limited to planting, fertilizing, tilling, harvesting. The vehicle 10 is equipped with a sampling implement 100 for sensing and/or sampling at least one of soil and vegetation. The sampling implement 100 is disposed on the vehicle 10 at any location that allows for sensing and/or sampling. In one embodiment as illustrated in FIG. 3, the sampling implement 100 is disposed on a front axle housing 11 (or frame member 11) via axle bracket 12. Disposing sampling implement 100 on front axle housing 11 provides for rigid mounting that does not have significant transverse movement compared to the direction of travel of the vehicle 10. Some vehicles 10 are steered from the rear, which can create transverse motion to the direction of travel. Alternatively, sampling implement 100 can be disposed on vehicle 10 adjacent to axle housing 11 similar to as shown in FIG. 1.

The vehicle 10 includes a location system 10000 for determining the position of vehicle 10 on the earth. Location system 10000 can be any system that uses signals from a known source for determining position. Location system 10000 can be a global positioning system 10001, and location system 10000 can further include a differential global positioning system (DGPS) 10002.

In one embodiment, a map 10003 that has field positions is used to send a signal to sampling implement 100 to direct sampling implement 100 to sense and/or sample soil and/or vegetation at each field position in map 10003 as the vehicle 10 traverses a field. Map 10003 can be stored in memory 2805 in a central processing unit (CPU) 2820 (e.g., processing system 2820) or memory 2805 that is associated with the CPU. CPU 2820 can be disposed on vehicle 10 or it can be remote from vehicle 10 and in wireless data communication with sampling implement 100.

The map 10003 that is used to indicate where to sense or take a sample can be any map that has information about the field that was previously measured. Examples of maps include, but are not limited to, yield, moisture, soil nutrient content, pH, organic matter content, electrical conductivity, soil compaction, elevation, drainage, and NDVI (normalized difference vegetation index). Soil nutrients include, but are not limited to, nitrogen, phosphorus, potassium, calcium, sulfur, magnesium, zinc, manganese, boron, chlorine, copper, iron, and molybdenum. Points in the field for sensing and/or sampling can be selected based on points in the field that had high, average, low measurements, or combinations thereof for the characteristic measured. These maps are not based on geo selection such that the points are chosen to evenly sample a field. The points are chosen based on the previously tested values.

In one embodiment, disclosed is an agricultural implement 5 that includes vehicle 10, a collection system 15, and a testing system 16. Additionally, if needed, a processing system 17 can be further included to process the samples prior to testing.

In one embodiment shown in FIGS. 1 to 8, collection system 15 is a probe collection system 15. Probe collection system 15 is attached to the vehicle 10, and it has a four bar linkage 102 with upper bars 103-1, 103-2 and lower bars 104-1, 104-2 attached at their first ends to vehicle 10 and connected to a soil probe 106 at their second ends to an upper end of soil probe 106. At a lower end of soil probe 106, there is a collection port extending through soil probe 106 along a direction of travel of vehicle 10. To drive soil probe 106 into the soil and withdraw soil probe 106, an actuator 105 is disposed between soil probe 106 and vehicle 10. A signal from CPU 2820 is sent to actuator 105 to lower soil probe 106. Once in the soil, soil probe 106 is pulled downward by the contact with the soil. When a sample has been taken, CPU 2820 sends a signal to actuator 105 to raise soil probe 106. Also, the position of the sample is stored in memory 2805. A plunger 111 on plunger arm 110 attached to vehicle 10 receives a signal from CPU 2820 to move to soil probe 106 and align plunger 111 with collection port 107. A signal from CPU 2820 causes plunger 111 to extend into collection port 107 and eject the sample from the collection port 107. Waiting for the sample is collection container 121, which is attached to collection arm 120, which is attached to vehicle 10. Prior to the plunger ejecting the sample, CPU 2820 sends a signal to collection arm 120 to move collection container 121 to a position adjacent to the collection port 107 opposite of the plunger 111. After the sample has been delivered to collection container 121, collection arm 120 is actuated to move collection container 121 to a processing system described below. In an alternative embodiment shown in FIG. 6, the plunger 111 in not attached to plunger arm 110. Plunger 117 is in soil probe 106 adjacent to collection port 107. Soil probe 106 has a plunger lip 116 disposed on plunger 117 opposite the side of the collection port 107. Plunger lip 116 has a diameter greater than plunger 117 such that a biasing member 118 (such as a spring) is disposed between plunger lip 116 and collection port 107 to keep plunger 117 retracted and collection port 107 open. Disposed behind plunger 117 opposite of collection port 107 is a cam 115. Cam 115 when rotated will cause plunger 117 to extend into collection port 107 to eject the sample. Cam 115 is in communication with CPU 2820 to receive signals to actuate when samples need to be ejected. In another embodiment (not shown), biasing member 118 need not be included. The force from soil entering collection port 107 will cause plunger 117 to retract along with cam 115 being commanded by CPU 2820 to allow plunger 117 to not be in collection port 107. In another embodiment shown in FIG. 5, soil probe 106 can have multiple collection ports 107. To eject samples, a multiple plunger 113 having a shaft 114 is driven by a linear actuator 112, which is attached to plunger arm 110. Linear actuator 112 is in communication with CPU 2820 to allow multiple plunger 113 to enter then withdraw from the collection ports 107.

Figure 8:
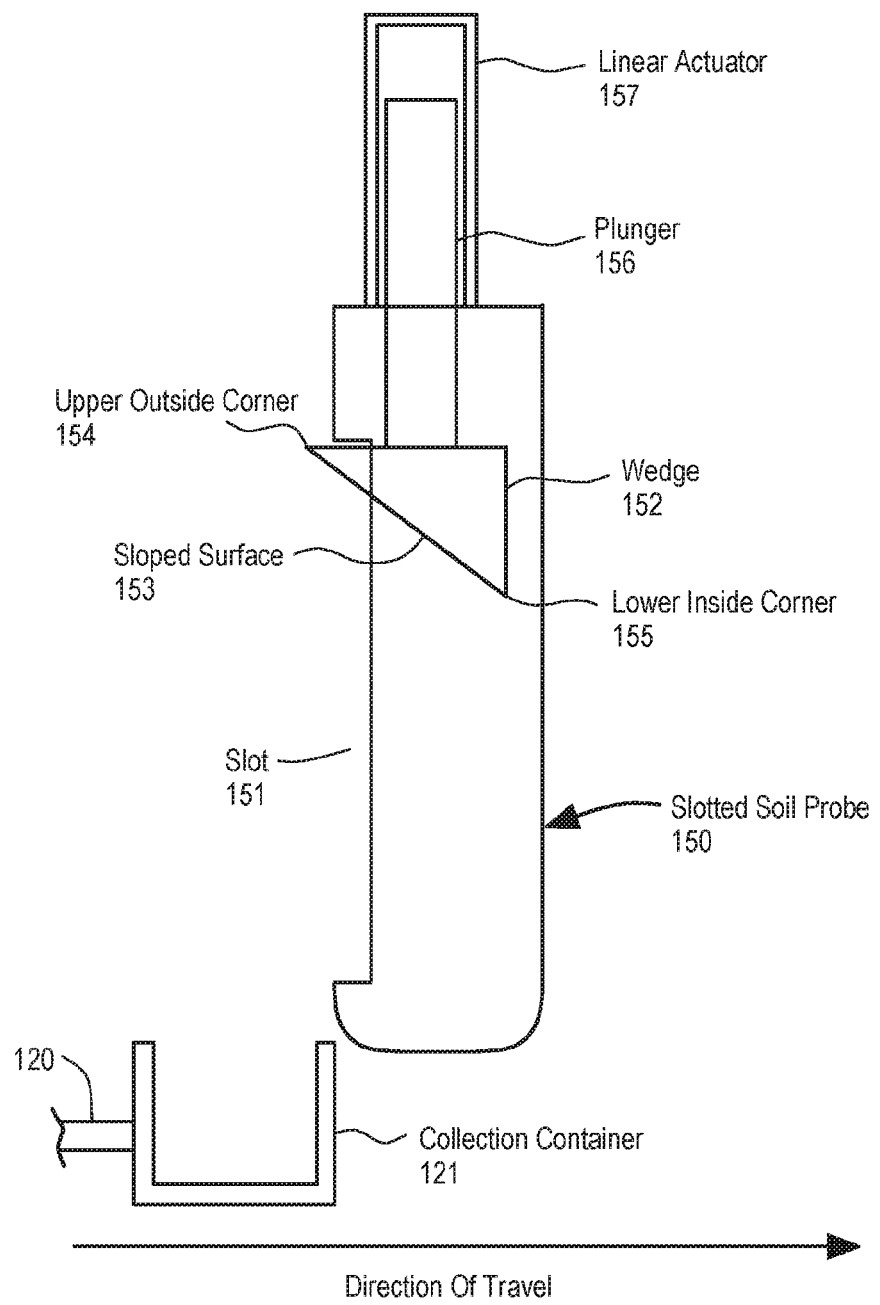
FIG. 8 is a side elevation view of a soil probe according to one embodiment.

In another embodiment as shown in FIGS. 7A to 7D, a notched soil probe 130 replaces soil probe 106 as in FIG. 1 with notched soil probe 130 connected to upper bars 103-1, 103-2 and lower bars 104-1, 104-2. Notched soil probe 130 has notches 131 on a side rearward of a direction of travel. Notched soil probe 130 is plunged into soil by actuator 133 to collect soil inside of notched soil probe 130 and then withdraw. There will be soil exposed in notches 131. Disposed adjacent to notched soil probe 130 is a rod 142 having scooper discs 141 that align with the notches 131. Rod 142 is attached to vehicle 10 through a rotary actuator 144, which allows rotation of rod 142 to allow scooper discs 141 to scoop soil from notches 131. Rod actuator 144 is attached to rod arm 143, which is attached to vehicle 10. Rotary actuator 144 is in communication with CPU 2820 to receive signals to cause rotary actuator 144 to rotate. Soil is removed from notches 131 and falls under gravity to collection container 121 (described above). After soil is removed from notches 131, there is a plunger 132 disposed within notched soil probe 130 at the top of notched soil probe 130 and is actuated by linear actuator 133, which is in communication with CPU 2820. Linear actuator 133 receives a signal from CPU 2820 to extend plunger 132 into notched soil probe 130 to expel soil out of notched soil probe 130. In another embodiment as shown in FIG. 8, notched soil probe 130 is replaced with slotted soil probe 150. This embodiment eliminates the need to use rod 142 and scooper discs 141. Slotted soil probe 150 has a slot 151 rearward of a direction of travel. Plunger 156 further has a wedge 152 disposed on its end. Wedge 152 extends the full inner diameter of slotted soil probe 150 and has a sloped surface 153 from top outside corner 154 to lower inside corner 155. When slotted soil probe 150 is withdrawn from the soil, linear actuator 157 receives a signal from CPU 2820 to extend plunger 156 and wedge 152 down through slotted soil probe 150. The soil within slot 151 falls under gravity into collection container 121 (as described above).

Figure 9A:
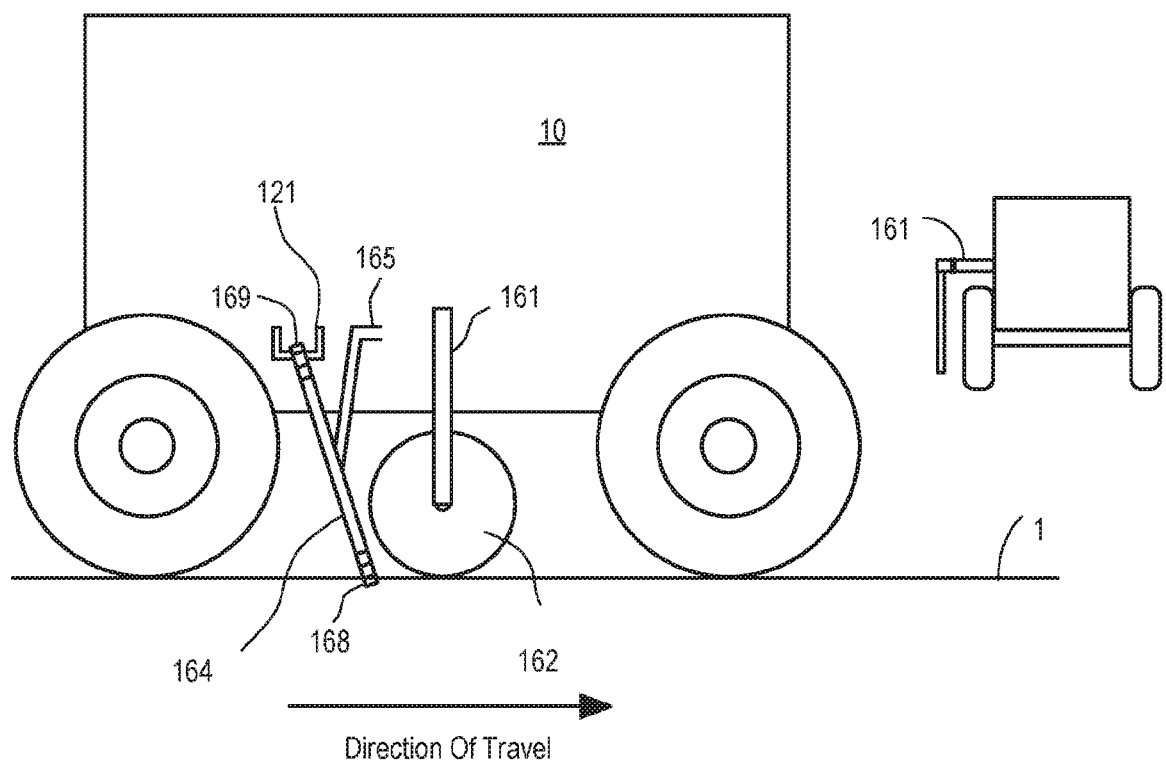
FIG. 9A is a side elevation view of a vehicle with a disc and auger collection system according to one embodiment.

In another embodiment as shown in FIGS. 9A to 9B, collection system 15 is a disc and auger collection system 15. Disc 162 is connected to vehicle 10 by arm 161. In one embodiment, disc 162 is offset from vertical. As disc 162 rotates, a trench 2 is formed in soil 1. An auger 164 is connected to the vehicle, and auger 164 has a soil entrance end 168 that extends into trench 2 for collecting soil. The soil is transported up the auger to a soil exit end 169 and then dispensed into collection container 121. Auger 164 is in data communication with CPU 2820, which commands auger 164 to actuate to collect soil. After soil is collected in collection container 121, auger 164 can be raised out of trench 2 and commanded to actuate to empty auger 164 of soil.

In an alternative embodiment as shown in FIG. 9B, a disc collection system 15 is shown. Cutter disc 166 is connected to vehicle 10 by arm 161. Cutter disc 166 is tapered along its radial edge. As cutter disc 166 rotates, a trench 2 is formed in soil 1. An auger 164 is connected to the vehicle, and auger 164 has a soil entrance end 168 that extends into trench 2 for collecting soil. The soil is transported up the auger to a soil exit end 169 and then dispensed into collection container 121. Auger 164 is in data communication with CPU 2820, which commands auger 164 to actuate to collect soil. After soil is collected in collection container 121, auger 164 can be raised out of trench 2 and commanded to actuate to empty auger 164 of soil.

Figure 10A:
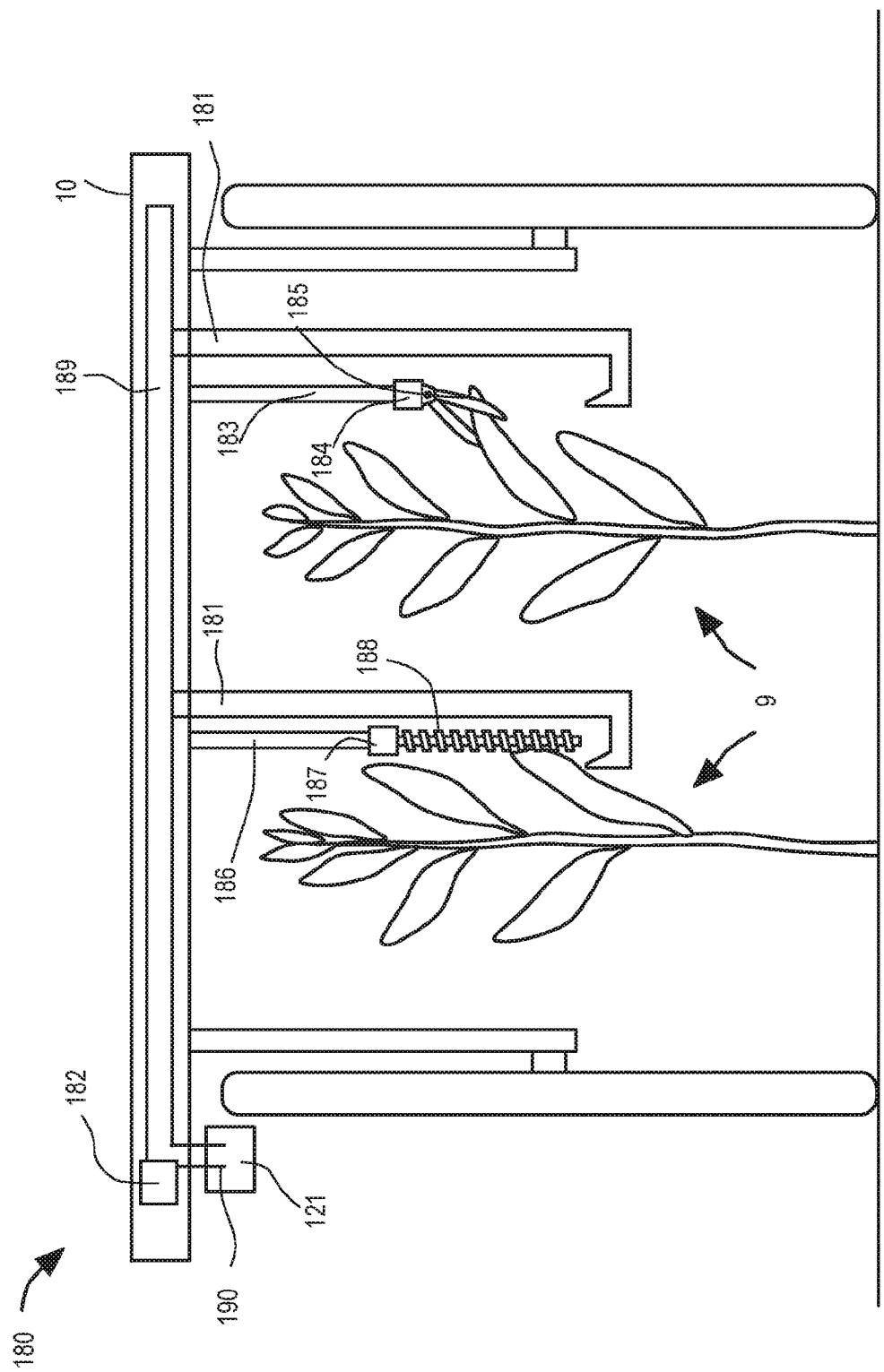
FIG. 10A is a front elevation view of a vegetation collection system according to one embodiment.
Figure 10B:
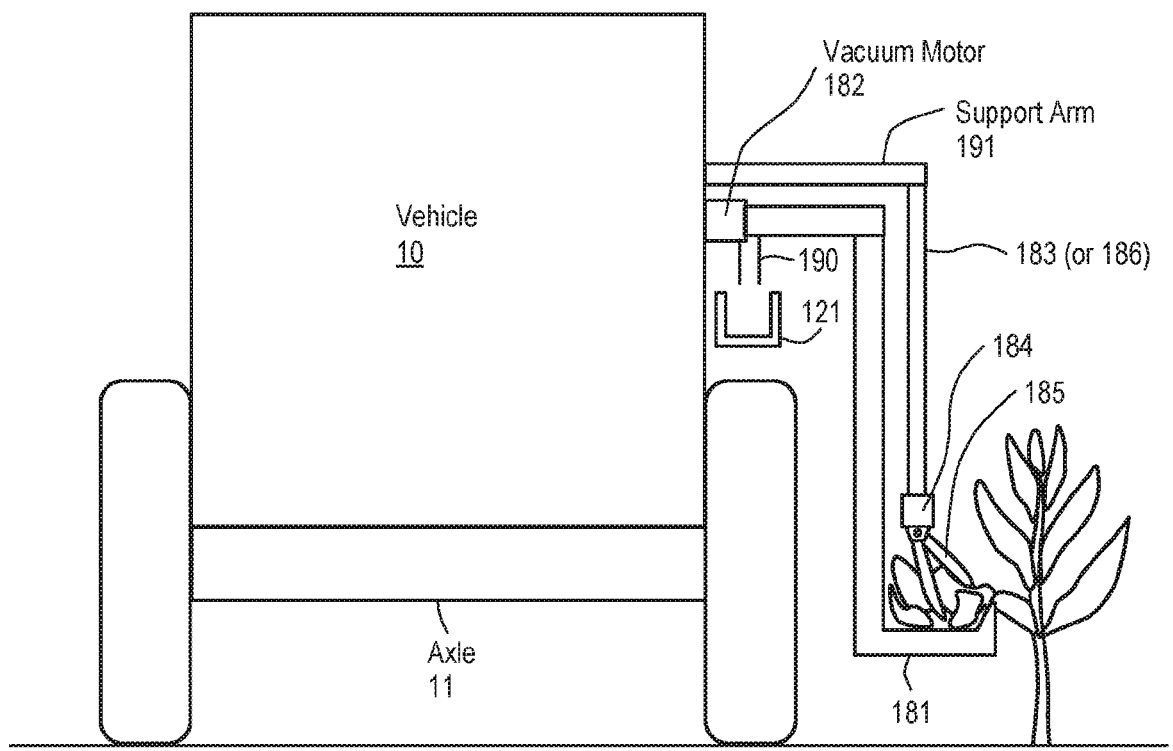
FIG. 10B is a front elevation view of a vegetation collection system according to one embodiment.
Figure 10C:
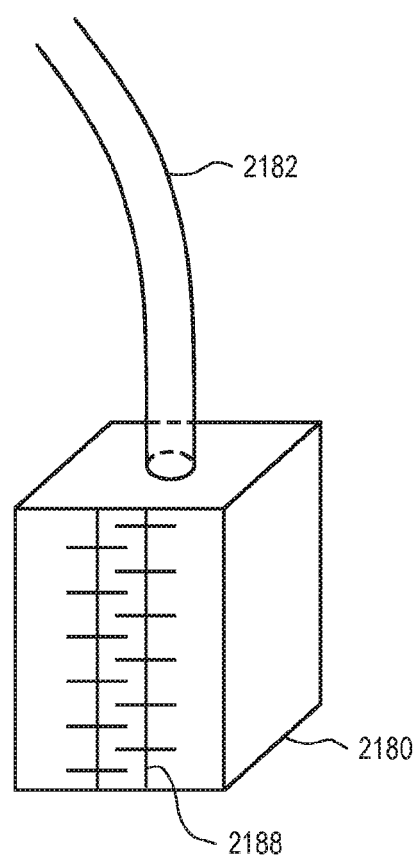
FIG. 10C is a perspective view of a vegetation collection system according to one embodiment.

As illustrated in FIG. 10A, vegetation collection system 180 cuts and collects vegetation. FIG. 10A illustrates two separate embodiments. Both embodiments have a main vacuum line 189 in communication with a vacuum motor 182 and a vacuum tube exit 190. In both of these embodiments, the vehicle 10 passes over the vegetation to be collected. Main vacuum line 189 has a vacuum tube 181 extending down from the main vacuum line 189 and ending proximate to a cutter (scissors 185 or sickle 188). In one embodiment, a sickle arm is disposed under vehicle 10 and extends downward. A motor 187 is disposed at the end of sickle arm 186 and is connected to sickle 188. Motor 187 is in communication with CPU 2820 to receive signals to actuate to drive sickle 188. In the other embodiment, a scissor arm 183 is disposed under vehicle 10 and extends downward. An actuator 184 is disposed at the end of scissor arm 183 and is connected to scissors 185. Actuator 184 is in communication with CPU 2820 to receive signals to actuate scissors 185. In an alternative embodiment illustrated in FIG. 10B, the vegetation collection system 180 is disposed on the side of vehicle 10. Support arm 191 is disposed on the side of vehicle 10 projecting out from vehicle 10. Scissor arm 183 (or sickle arm 186) is then disposed at the end of support arm 191. Either of the above embodiments for sickle 188 or scissors 185 can be used in this embodiment. Another embodiment that can be used with either embodiment shown in FIG. 10A or 10B is illustrated in FIG. 10C. This embodiment is similar to the device described in U.S. Pat. No. 5,142,786. A body 2180 has a sickle 2188 disposed on an opening 2182 on a side of body 2180. A vacuum hose 2182 is attached to body 2180 to pull clippings through hose 2182 for collection. Vacuum pulls vegetation into body 2180 where sickle 2188 cuts the vegetation.

The sample when taken is associated with a location by location system 10000. The sample with its specific location is stored in memory 2805, and tracked by CPU 2820 as the sample transfers from one system to the next system such that results from testing are associated with the location tested.

Processing

A processing system 2820 can be a soil processing system or a vegetation processing system.

Figure 11A:
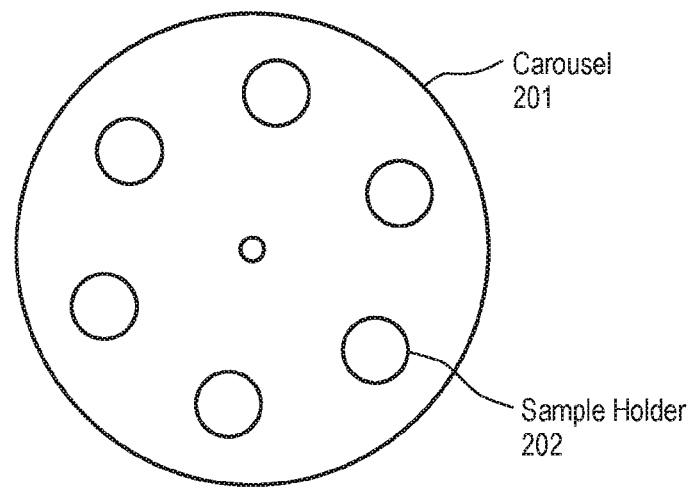
FIG. 11A is a top elevation view of a carousel according to one embodiment.
Figure 11B:
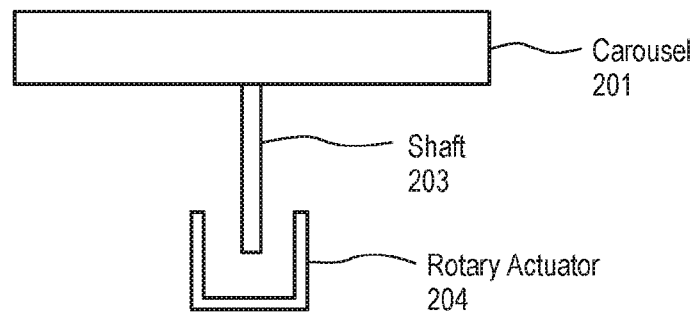
FIG. 11B is a side elevation view of the carousel of FIG. 11A according to one embodiment.
Figure 11C:
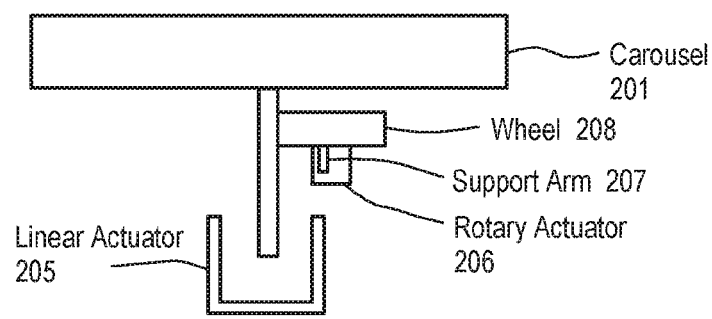
FIG. 11C is a side elevation view of the carousel of FIG. 11A according to one embodiment.

To accommodate multiple samples during collection, during processing, or during testing, samples can be conveyed by sample conveyors. In one embodiment as shown in FIG. 11, a carousel 201 has multiple sample holders 202 for holding collection containers 121 or test containers 60 (not shown). Carousel 201 is rotatable by having a rotary actuator 204 turning shaft 203, which is connected to carousel 201. Rotary actuator 204 is in communication with CPU 2820 for receiving signals to rotate carousel 201. In another embodiment, shaft 203 is actuated by linear actuator 205, which is in communication with CPU 2820, to raise or lower carousel 201 to deliver or remove a sample from a location. To rotate carousel 201, a wheel 208 is in contact with shaft 203. Wheel 208 is driven by rotary actuator 206, which is in communication with CPU 2820.

Figure 12A:
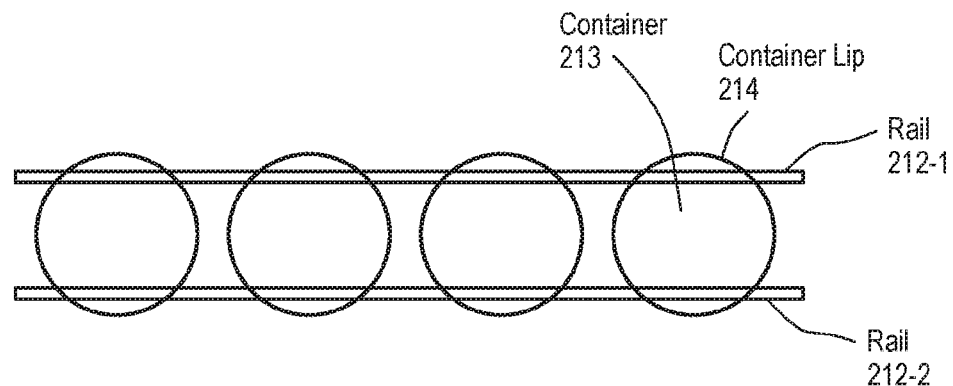
FIG. 12A is a top elevation view of a conveyor system according to one embodiment.
Figure 12B:
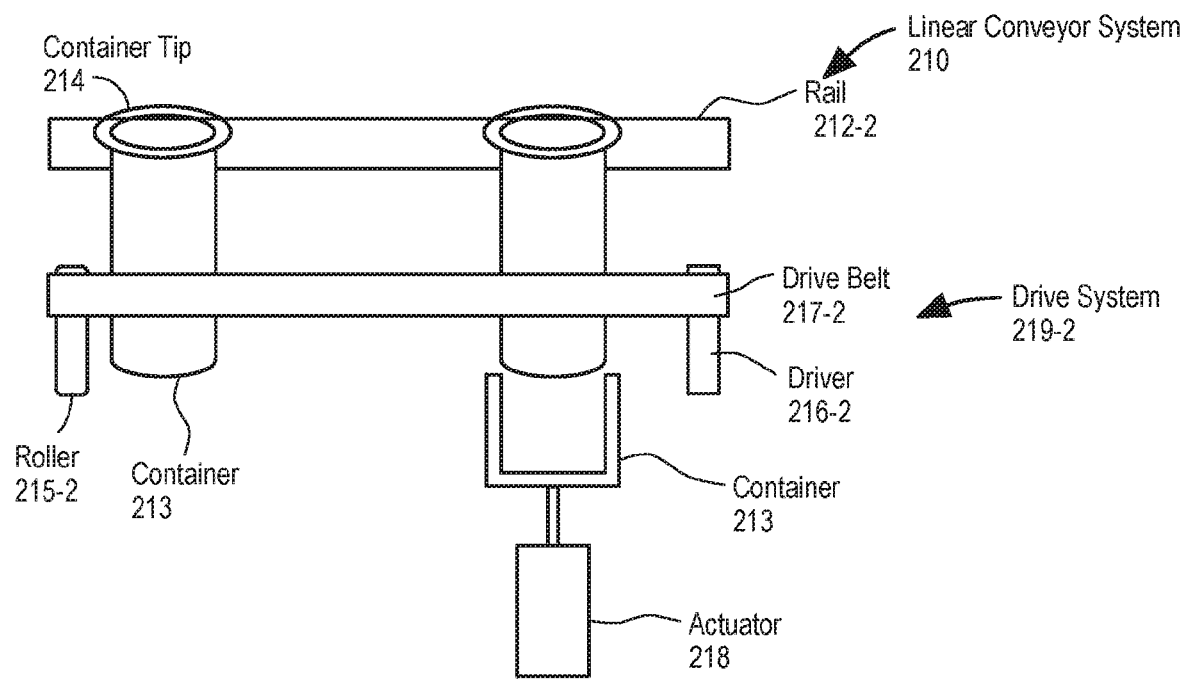
FIG. 12B is a side elevation view of the conveyor system of FIG. 12A according to one embodiment.

In another embodiment as shown in FIGS. 12A to 12B, a linear conveyor system 210 moves containers 213 (either collection containers 121 or test containers 60). Containers 213 have a lip 214. Container 213 is positioned between rails 212-1 and 212-2, and container lip 214 rests on rails 212-1 and 212-2. Positioned under rails 212-1 and 212-2 on each side of container 213 are drive systems 219-1 and 219-2. Each drive system 219-1 and 219-2 has a drive belt 217-1 or 218-2, respectively, disposed over drivers 216-1 and 216-2, respectively, and roller 215-1 and 215-2 respectively. Drive belts 217-1 and 217-2 frictionally engage containers 213. Drivers 216-1 and 216-2 are in communication with CPU 2820 to receive signals to move containers 213 along linear conveyor system 210. Containers 216 can be positioned in linear conveyor system 210 such that each container 213 is at a separate location for processing or testing. Optionally, container 213 can be positioned over an actuator 218, which is in communication with CPU 2820. Actuator 218 can either be linear (to raise or lower container 213) or rotary (to spin container 213).

Soil samples can be processed before testing to provide a more refined sample without aggregates and smaller particles for increased surface area. To remove aggregates, such as rocks, stones, or pebbles, soil samples can be strained through a screen. Examples of a screen include, but are not limited to, a screen with auger, soil trammel, roto-screen, push screen, and shake screen.

Figure 13A:
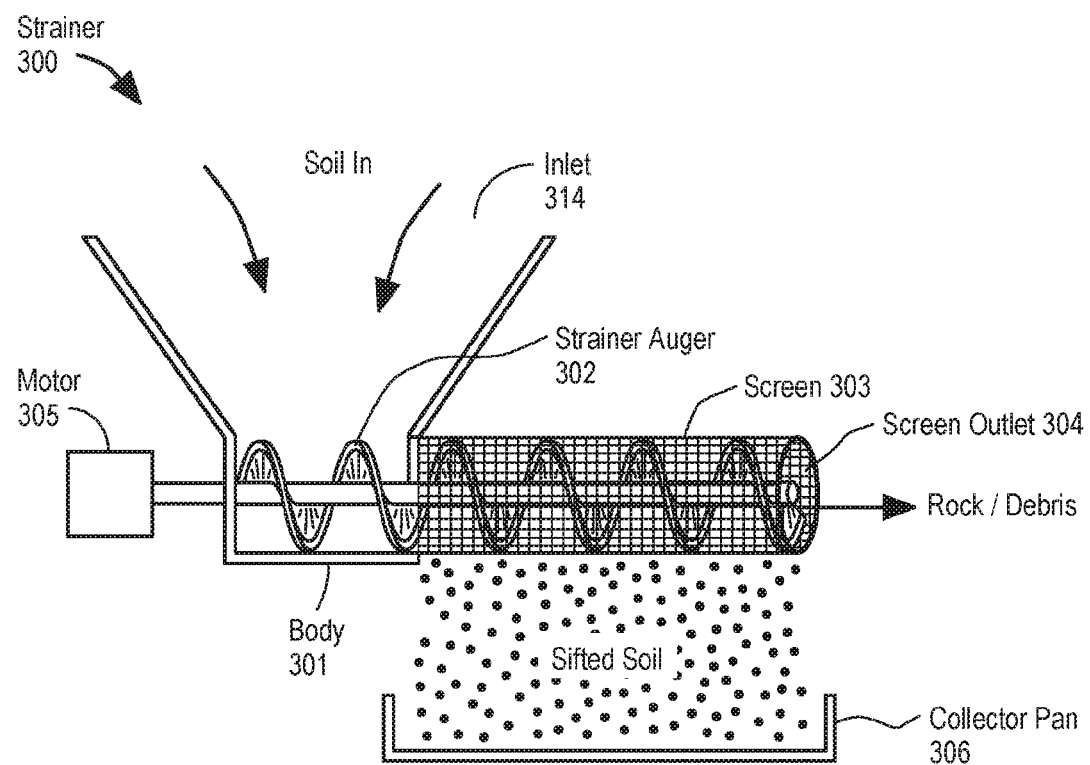
FIG. 13A is a side elevation view of a strainer according to one embodiment.

As shown in FIG. 13A, soil can be separated from larger debris, such as rocks, through a strainer 300. Strainer 300 has in inlet 314 into body 301. A strainer auger 302 is disposed within the strainer body 301 and extends into screen 303, which is attached to strainer body 301. A motor 305 is connected to strainer auger 302 for driving strainer auger 302, and motor 305 is in communication with CPU 2820. Screen 303 can be a cylinder, or it can be tapered. Screen 303 has a screen outlet 304 opposite to where screen 303 attaches to strainer body 301. Screen outlet 304 allows rocks and other debris to exit the strainer 303. Screen 303 can have any desired mesh size. Sifted soil exits through screen 303. The sifted soil can be collected in collection pan 306.

Figure 13B:
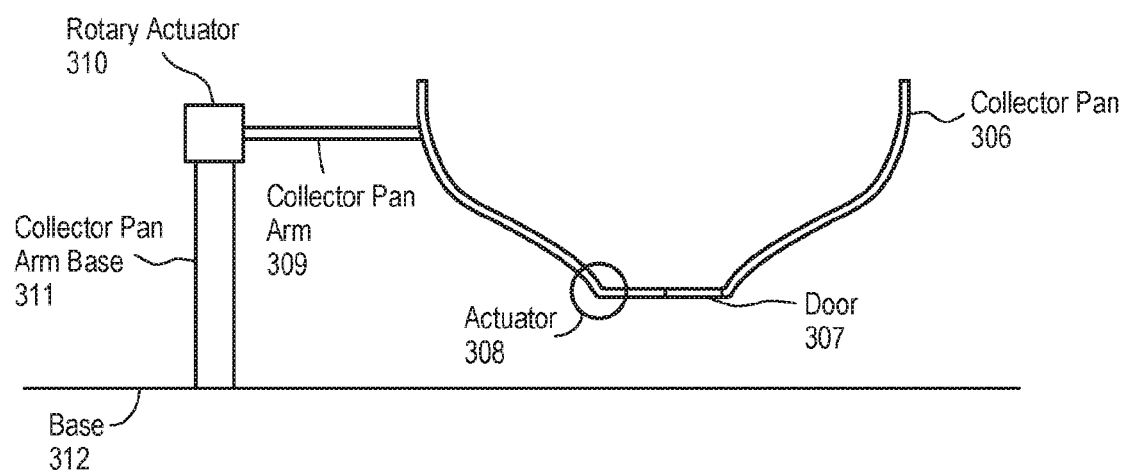
FIG. 13B is a side elevation view of the collection pan of FIG. 13A according to one embodiment.
Figure 13C:
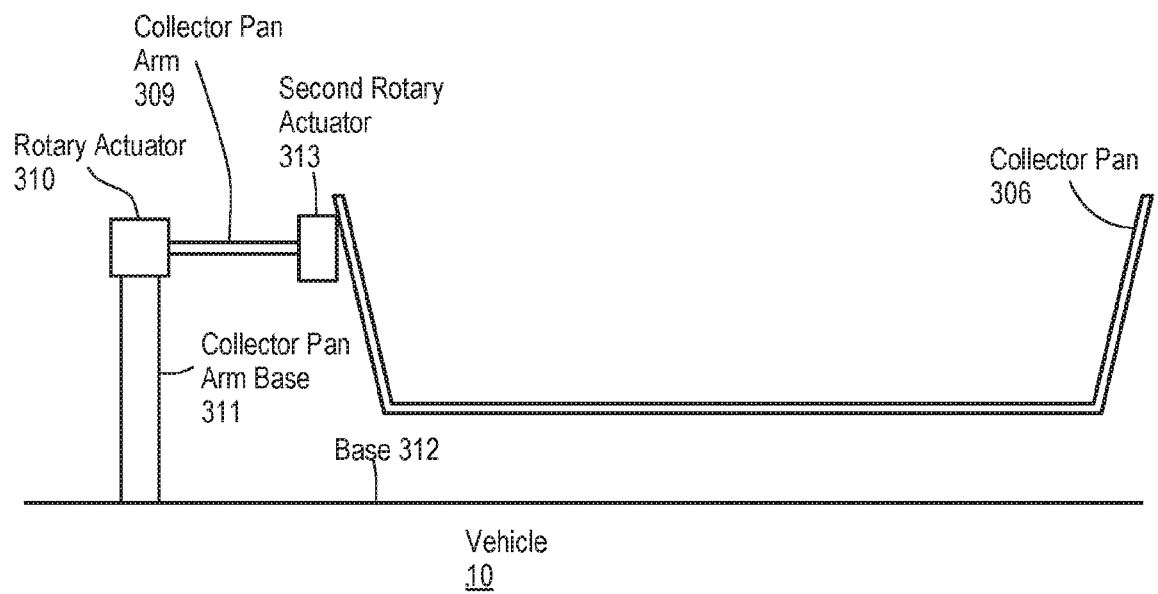
FIG. 13C is a side elevation view of the collection pan of FIG. 13A according to one embodiment.

From collection pan 306, as illustrated in FIG. 13B, the sample can be transferred directly to testing, or the sample can be further processed. A collection pan arm base 311 is attached to a base 312, which can be vehicle 10, and has a rotary actuator 310 at the end opposite to the end attached to base 312. A collection pan arm 309 is attached to the rotary actuator 310 and extends to a second rotary actuator 313, which is then connected to collection pan 306. Rotary actuator 310 and second rotary actuator 313 are in communication with CPU 2820, which can send signals to move collection pan 306 and then pour out collection pan 306 via the second rotary actuator 313. In another embodiment shown in FIG. 13A, the second rotary actuator 313 can be removed, and the collection pan 306 can be connected to the collection pan arm. The collection pan 306 can have a door 307 with actuator 308 that is in communication with CPU 2820 for opening and closing the door 308. To remove the sample, door 307 can be opened to allow the sample to fall under gravity. The sample can be further processed as described below or tested directly.

Figure 14:
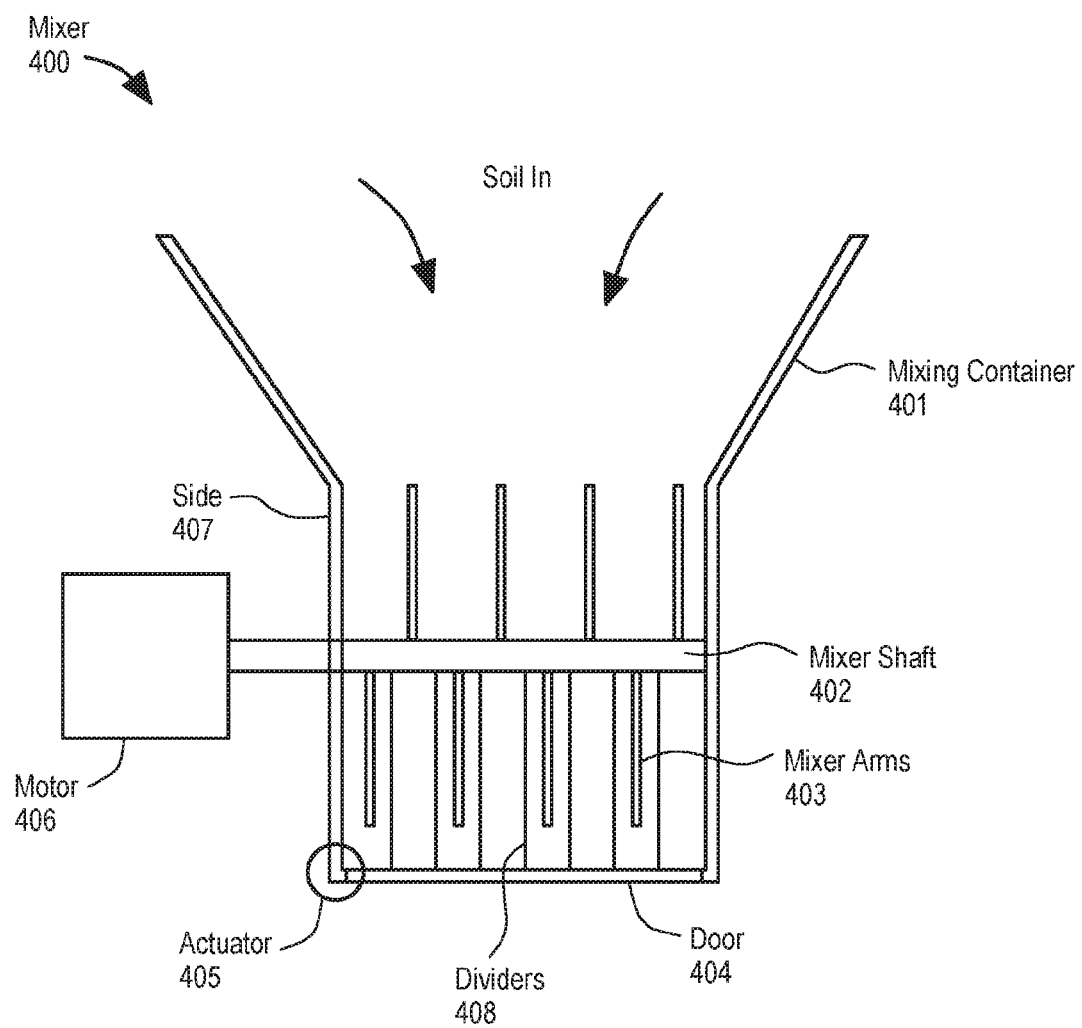
FIG. 14 is a side sectional view of a mixer according to one embodiment.

In one embodiment shown in FIG. 14, multiple samples can be mixed together or individual samples may be homogenized. Mixer 400 has a mixing container 401 and a mixer shaft 402 with mixing fingers 403 disposed through a side 407 of mixer 400. Mixer shaft 402 is driven by a motor 406, which is in communication with CPU 2820. Optionally, mixing container 401 can have dividers 408 disposed in mixing container 401 attached to walls within mixing container 401 and spaced to be between mixer arms 403. Mixer shaft 402 is rotated to mix the sample (or samples) to achieve desired mixing. When mixing is complete, mixer 400 has a door 404 with actuator 405 that is in communication with CPU 2820 for opening and closing the door 404. To remove the sample, door 404 can be opened to allow the sample to fall under gravity.

Figure 15A:
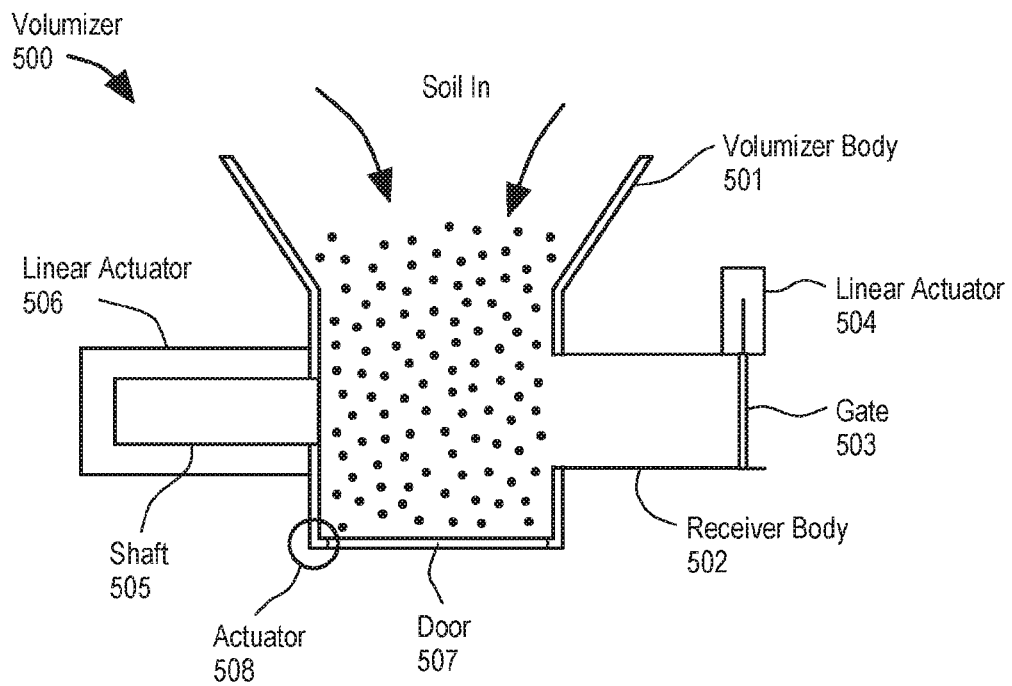
FIG. 15A is a side section view of a volumizer according to one embodiment.
Figure 15B:
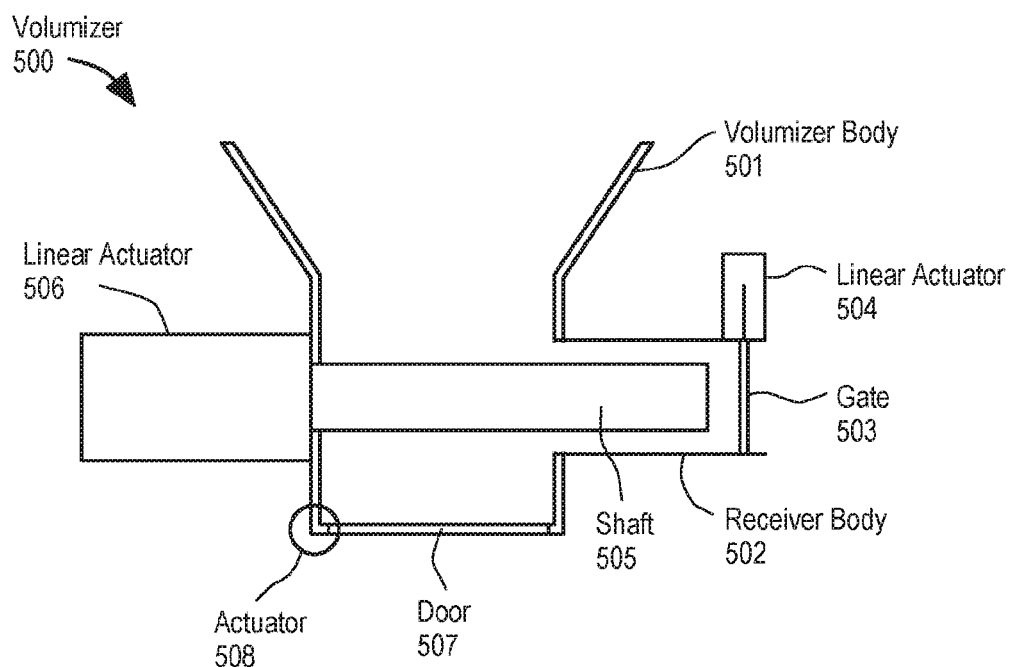
FIG. 15B is a side section view of the volumizer of FIG. 15A with the shaft actuated.

In addition to or instead of mixing, samples can be volumized. As shown in FIGS. 15A and 15B, volumizer 500 has a volumizer body 501. Disposed through volumizer body 501 is a shaft 505, which is driven by linear actuator 506, which is in communication with CPU 2820. Opposite to where shaft 505 enters volumizer body 501 is a receiver body 502. When a select amount of soil has been collected, CPU 2820 sends a signal to linear actuator 504 to extend shaft 505 to force soil into receiver body 502 to a gate 503. Gate 503 is disposed at the end of receiver body 502 and is driven by a linear actuator 504, which is in communication with CPU 2820. Shaft 505 is extended until a specified force is obtained on the sample. This will indicate that the sample has achieved a specified density. Once the sample has a specified density, then a known volume of sample is obtained. CPU 2820 sends a signal to linear actuator 504 to open gate 503, and CPU 2820 sends a signal to extend shaft 505 a set distance to expel the sample of a known volume, and linear actuator 504 is then activated to close gate 503. After the sample is obtained, gate 503 is opened, and linear actuator 506 is activated to drive shaft 505 to expel the remaining material in the receiver body 502. Alternatively, gate 503 can be opened and shaft 505 extended to a point that leaves a known volume in the receiver body 502 and gate 503 is closed. This expelled sample is waste. Gate 503 is then opened and shaft 505 is extended fully to eject the sample of known volume. Volumizer body 501 further has a door 507 with actuator 508 that is in communication with CPU 2820 for opening and closing the door 507. To remove the excess sample, door 507 can be opened to allow the excess sample to fall under gravity.

Figure 20A:
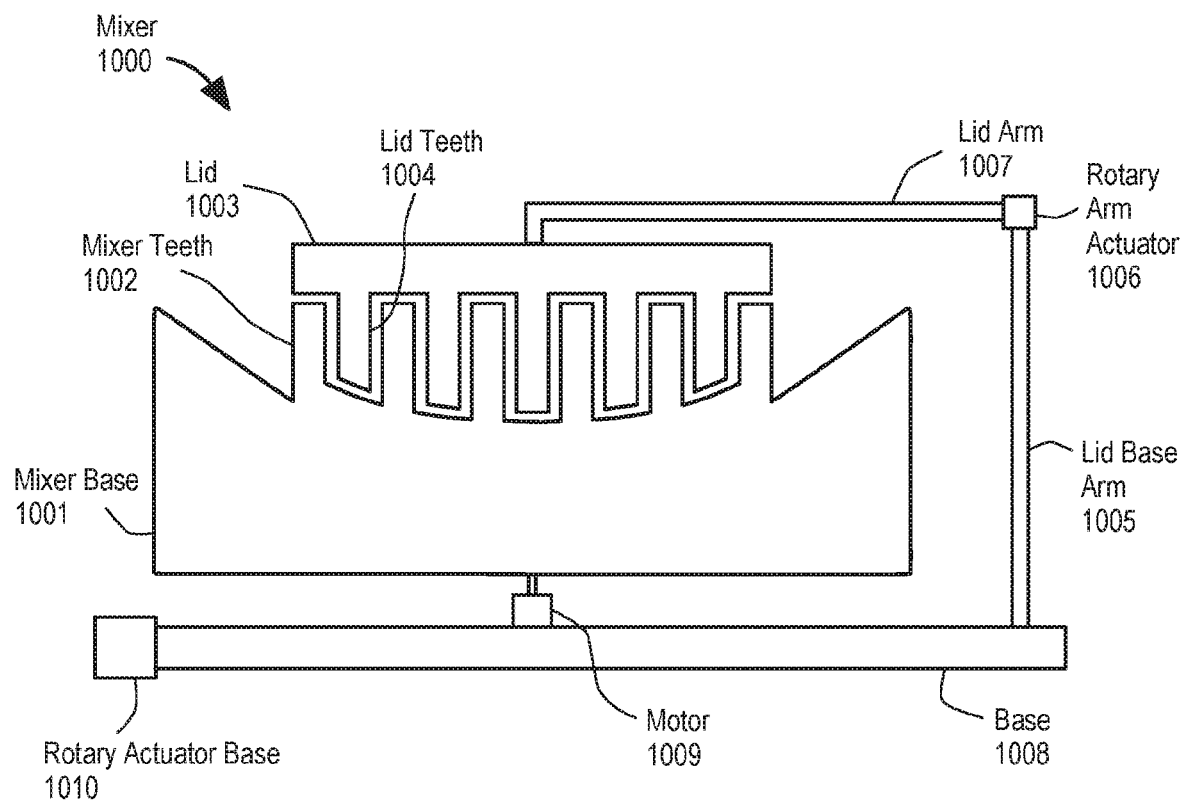
FIG. 20A is a side sectional view of a mixer according to one embodiment.
Figure 20B:
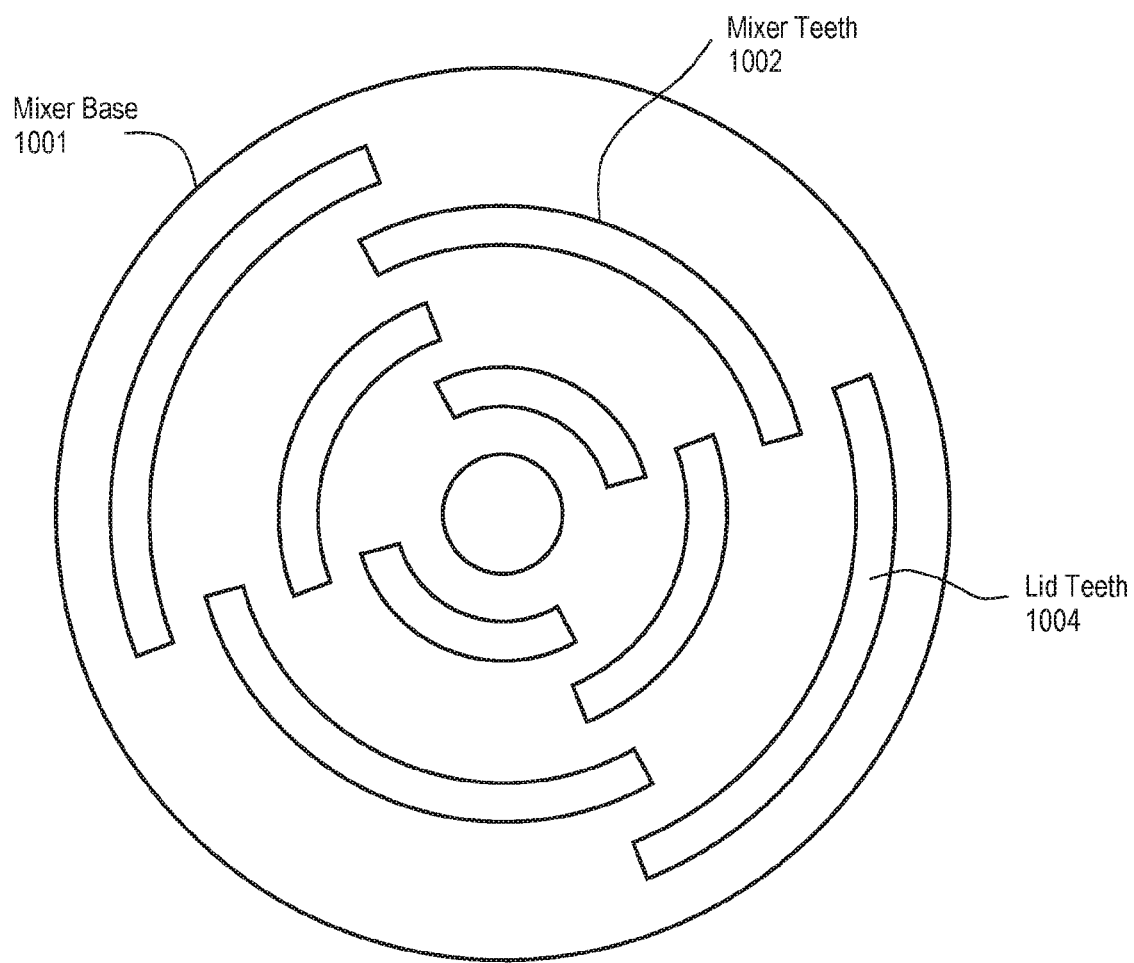
FIG. 20B is a top view of the mixer of FIG. 20A.

In another embodiment as illustrated in FIGS. 20A and 20B, another mixer 1000 is described. Mixer 1000 has a mixer base 1001 that is disposed on motor 1009 for spinning mixer base 1001. Motor 1009 is disposed on base 1008, which is connected to rotary actuator 1010 for rotating the base 1008 to empty the contents of mixer base 1001. Motor 1009 is in communication with CPU 2820 to actuate mixer base 1001. Extending above mixer base 1001 are mixer teeth 1002, which are curved about radii of mixer based 1001. A lid 1003 is disposed over mixer base 1001, and lid 1003 has lid teeth 1004 that are curved about radii of lid 1003. The mixer teeth and lid teeth are interposed with one another when lid 1003 is disposed on mixer base 1001. To raise and lower lid 1003 to permit samples to be added and removed, lid 1003 is connected to a lid arm 1007, which is connected to rotary actuator 1006, which is connected to lid base arm 1005, which is connected to base 1008. Actuator 1006 is in communication with CPU 2820 to raise or lower lid 1003.

Figure 16:
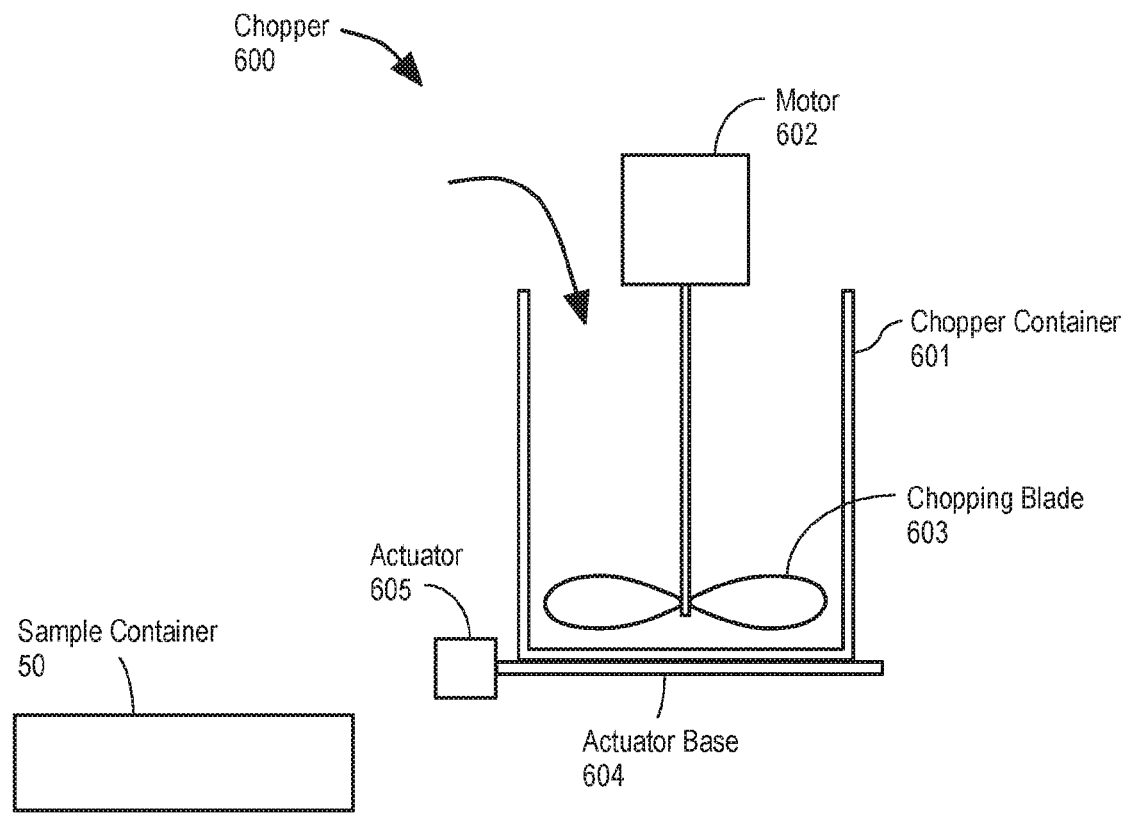
FIG. 16 is a side elevation view of a chopper according to one embodiment.

Vegetation samples can be processed to make smaller pieces of vegetation. A chopper 600 as shown in FIG. 16 can chop vegetation. Chopper 600 has a chopper container 601 with a chopping blade 603 inserted into the chopping container 601. Chopping blade 603 is driven by motor 602, which is in communication with CPU 2820 for actuating the chopper 600. Chopper 600 is disposed on base 604, which is connected to actuator 605, which is in communication with CPU 2820. After the vegetation is chopped, actuator 605 receives a signal to rotate base 604 to empty the contents of chopper container 601 into sample container 50.

Once the soil and/or vegetation sample is taken, a test sample 61 is prepared. An extractant and the sample are added to test container 60 and mixed with mixer 706. Mixer 706 is in communication with CPU 2820 to receive signals to mix. Alternatively, test container 60 can be a blender. The extractant is specifically chosen for extracting a chemical to be tested. In some embodiments, the extractant is water. In other embodiments, the extractant is any chemical extractant used to test for nutrients in soil and/or vegetation. Examples of extractants include, but are not limited to water, Mehlich 3 extractant, NaCl, DTPA (diethylenetriaminepentaacetic acid). AB-DTPA (ammonium bicarbonate-diethylenetriaminepentaacetic acid). Mehlich 1. Mehlich 2, Mehlich 3, $NH_4OAc$, Olsen P test extractant, Morgan extractant, Modified Morgan extractant, Bray-Kurtz extractant, $CaCl_2$, $BaCl_2$, $SrCl_2$, Hot Water, Truog extractant, Ambic extractant, $HNO_3$, LiCl, calcium-acetate-lactate, oxalate, citrate-bicarbonate-dithionite, HCl, acid ammonium oxalate.

Figure 17:
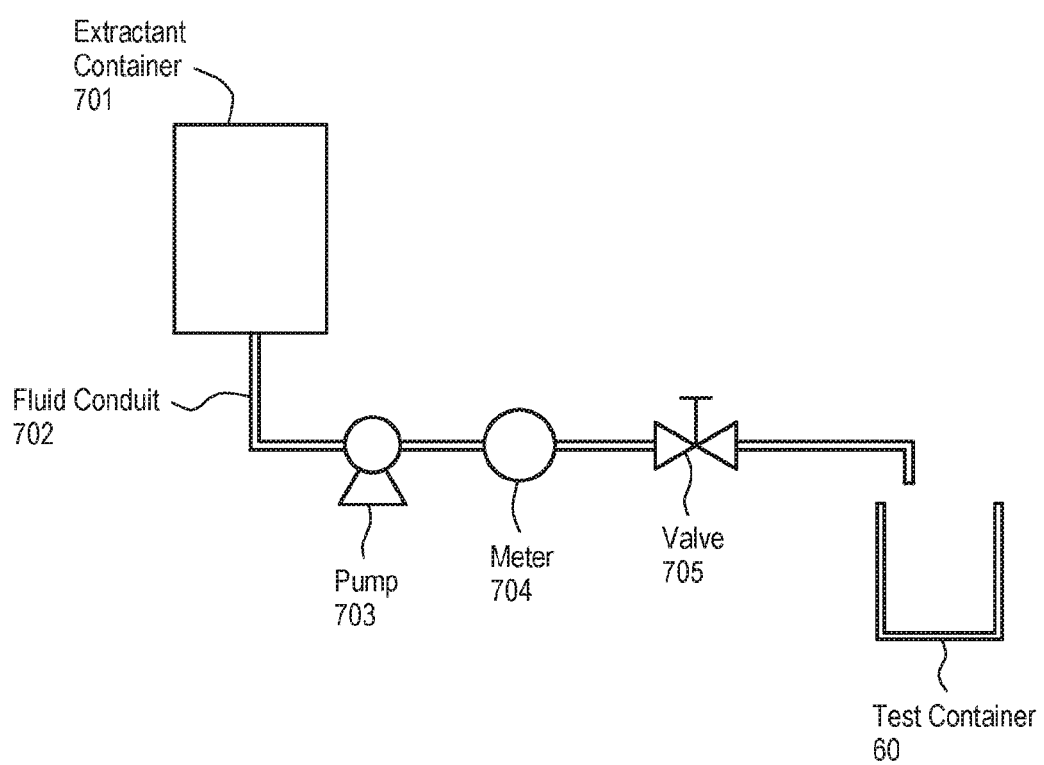
FIG. 17 is a side elevation view of a flow system for extractant according to one embodiment.
Figure 18A:
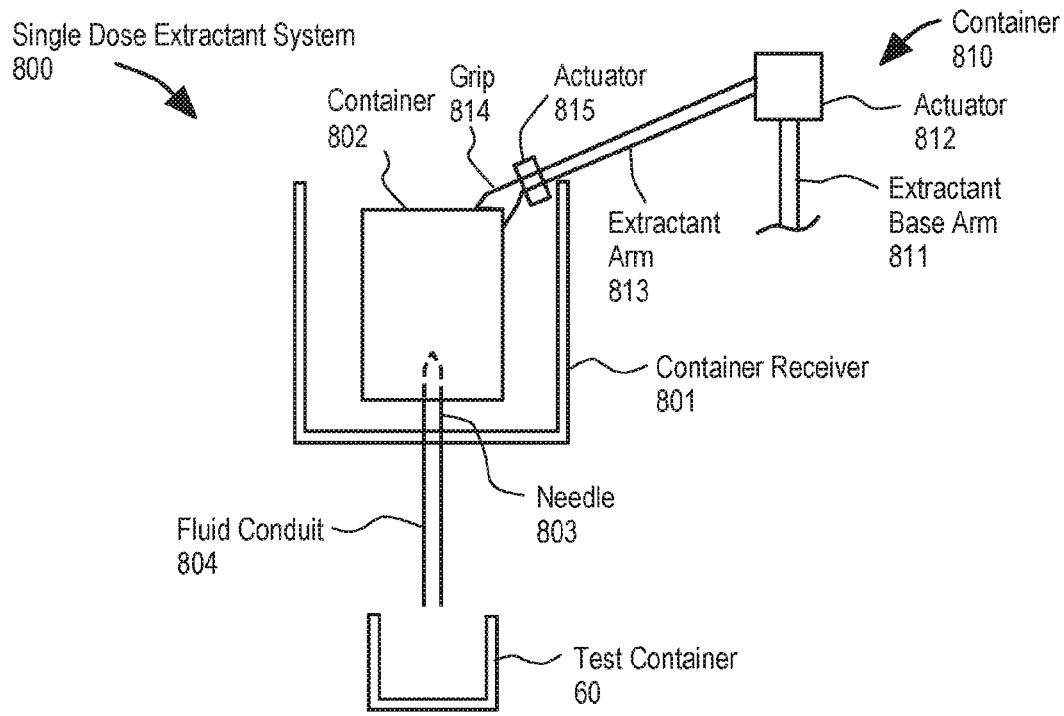
FIG. 18A is a side elevation view of a single dose extractant system according to one embodiment.

In one embodiment illustrated in FIG. 17, the extractant is contained in extractant container 701. From extractant container 701, the extractant flows through fluid conduit 702 through pump 703, meter 704, and valve 705 to test container 60. Meter 704 is in signal communication with valve 705 and pump 703 through CPU 2820 to open and close the valve 705 to add a selected amount of extractant to the test container 60. The extractant and the sample amounts are measured to create the test sample with a known amount of sample per extractant to then provide a concentration of extracted chemical in the extractant. In another embodiment illustrated in FIG. 18A, extractant container 701 is a single dose extractant container 802. Single dose extractant container 802 is placed into container receiver 801 that has a needle 803 to puncture single dose extractant container 802 to allow the extractant to flow out of single dose extractant container 802 and into container receiver 801. Container receiver 801 can then be in place of extractant container 701 in the system described above. Alternatively, pump 703, meter 704, and valve 705 can be omitted with container receiver 801 flowing to test container 60. For extractants that are non-fluid, a solvent, such as water, can be injected into single dose extractant container 802 via injector that is in fluid communication with a solvent container (not shown). Container receiver 801 can contain a container ejector 810 to remove the single dose extractant container 802 so that a new single dose extractant container 802 can be used. Container ejector 810 is in communication with CPU 2820. Container ejector 810 has an ejector base arm 811 directly or indirectly connected to vehicle 10. An actuator 812 is disposed on ejector base arm 811 for moving ejector arm 813. Disposed on ejector arm 813 is an actuator 812 for actuating grip 814 for gripping and removing single dose extractant container 802. Each actuator 812 and 815 of container ejector 810 is in communication with CPU 2820. Upon ejection, the used single dose extractant container 802 can be collected for disposal. Container ejector 810 can also be commanded to grab and insert the single dose extractant container 802 into the container receiver 801.

Figure 18B:
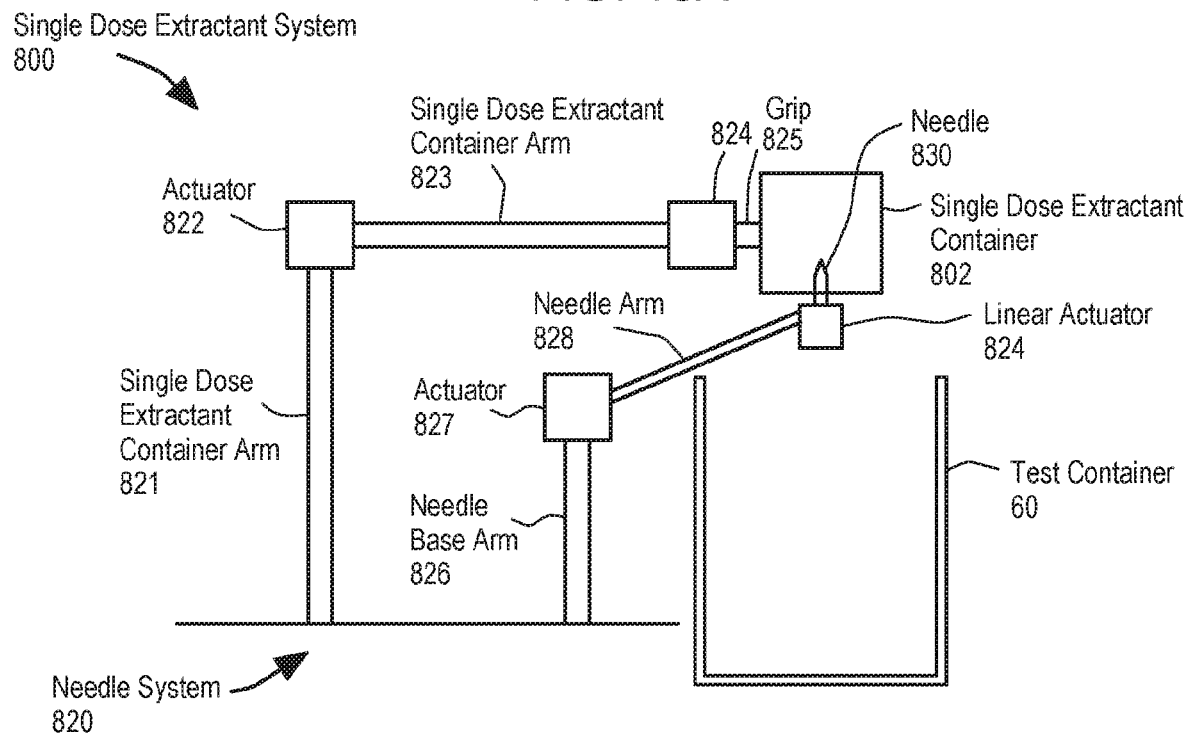
FIG. 18B is a side elevation view of a single dose extractant system according to one embodiment.
Figure 18C:
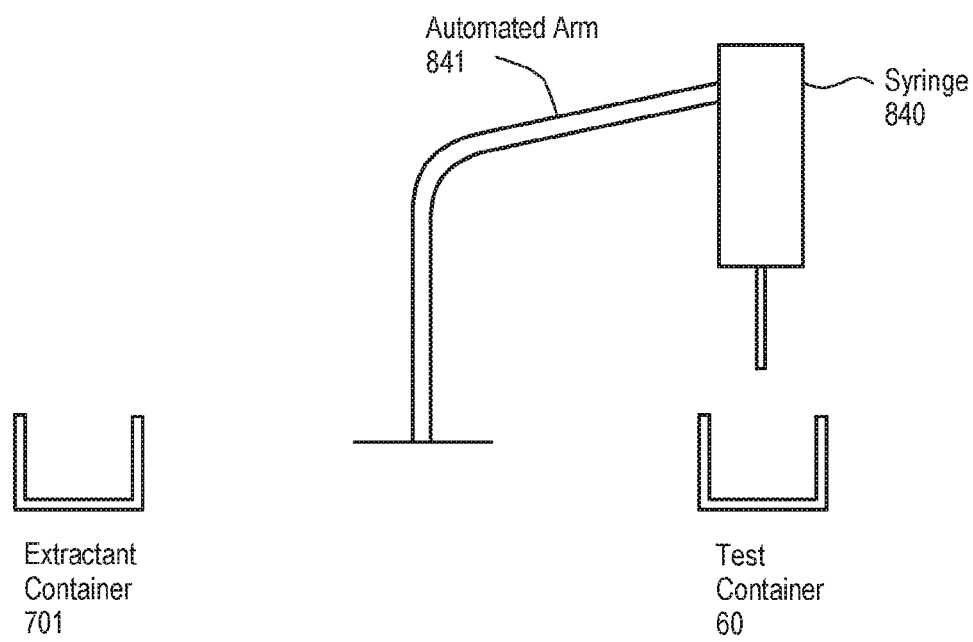
FIG. 18C is a side elevation view of a syringe system according to one embodiment.

In another embodiment shown in FIG. 18B, single dose container extractant container 802 is positioned over test container 60 by a single dose extractant system 800. Single dose extractant system 800 has a single dose extractant container base arm 821 directly or indirectly connected to vehicle 10. An actuator 822 is disposed on single dose extractant container base arm 821 for actuating a single dose extractant container arm 823. Disposed on single dose extractant container arm 823 is an actuator 824 actuating grip 825 for gripping single dose extractant container 802. Each actuator 822 and 824 are in communication with CPU 2820 for receiving signals to actuate. Single dose extractant system 800 takes a single dose extractant container 802 and moves it over the test container 60. A needle system 820 has a needle base arm 826 directly or indirectly connected to vehicle 10. An actuator 827 is disposed on needle base arm 826 to actuate needle arm 828. A linear actuator 829 is disposed on needle arm 827 to actuate a needle 830 to puncture single dose extractant container 802. Each actuator 824 and 829 are in communication with CPU 2820 for receiving signals to actuate.

The extractant can be ready to use such that no dilution of the extractant is needed. In another embodiment, the extractant can be stored on vehicle 10 as a concentrate that is then diluted to use concentration with water. In this embodiment, water would be added to sample container 50 as described above, and extractant is added to sample container with a similar fluid conduit 702, pump 703, meter 704, and valve 705. In another embodiment, the reagent can be a non-fluid. Examples of non-fluids include, but are not limited to, solids, powder, granules, pellets, dissolvable patch, pod (solid inside a dissolvable film).

Pump 703 can be any pump that is sized to deliver the needed amount of extractant. In certain embodiments, pump 703 is a peristaltic pump.

In another embodiment, fluid conduit 702, pump 703, meter 704, and valve 705 are replaced with a syringe 840. This can be used in the embodiment for delivering extractant to sample container 50 for dilution since syringe 840 can be sized to measure smaller quantities. In one embodiment, syringe 840 is a SGE™ eVol™ Handheld Automated Analytical Syringe from Fisher Scientific that is in data communication with CPU 2820. Syringe 840 is moved by automated arm 841 that is in data communication with CPU 2820. A signal is sent to automated arm 841 to move syringe 840 into contact with the extractant in extractant container 701. A signal is sent to syringe 840 to withdraw a specified amount of extractant. Automated arm 841 then receives a signal from CPU 2820 to move syringe 840 to test container 60, and then CPU 2820 sends a signal to syringe 840 to dispense the extractant into test container 60.

Multiple extractants can be used to test for different nutrients. In this embodiment, there is an extractant container 701, fluid conduit 702, meter 703, pump 704, and valve 705 for each extractant. In this embodiment, the amount of soil and/or vegetation collected at each point can be sized such that when divided there is enough sample for each test.

Figure 19A:
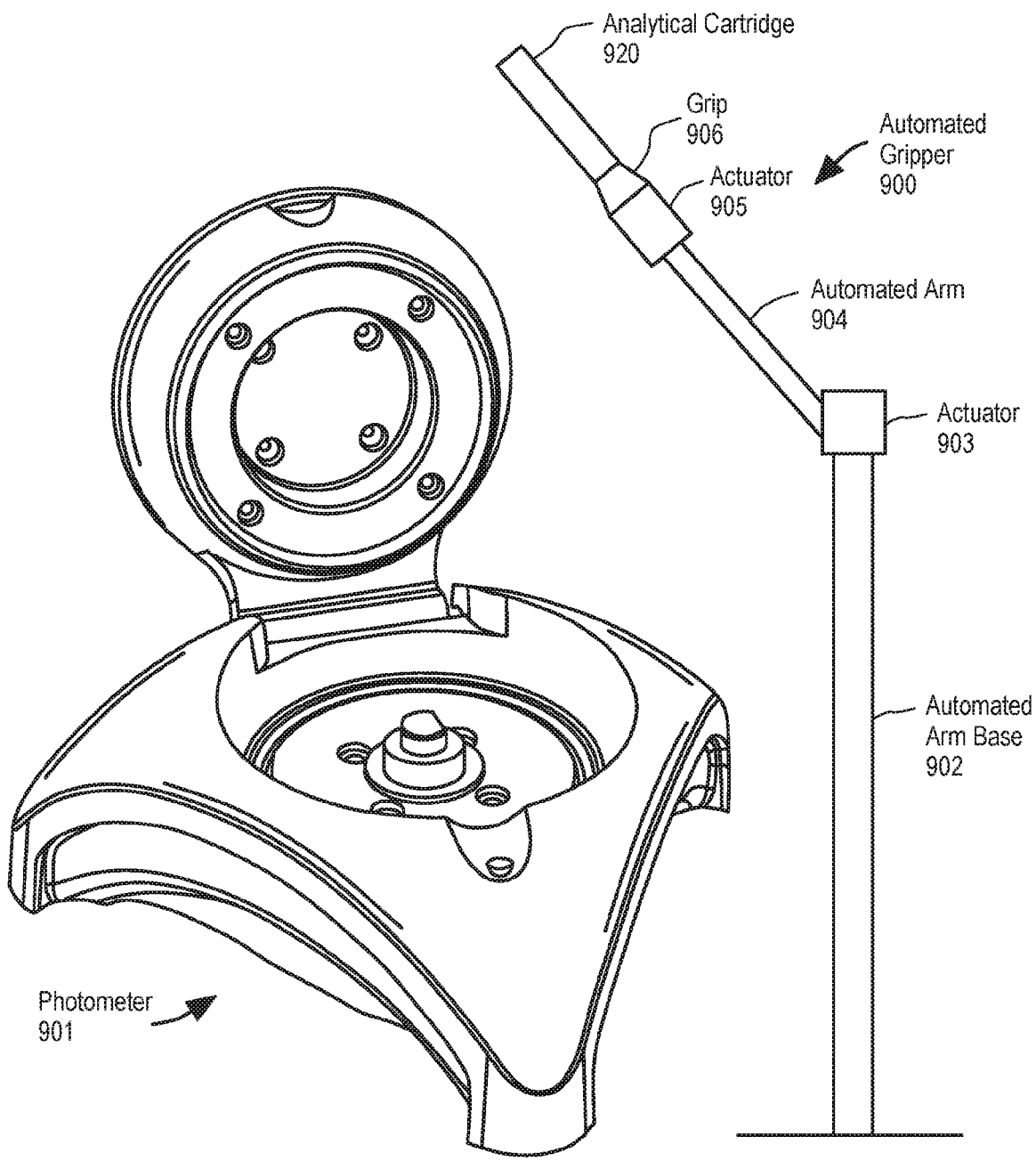
FIG. 19A is a perspective view of a photometer and analytical cartridge system according to one embodiment.
Figure 19B:
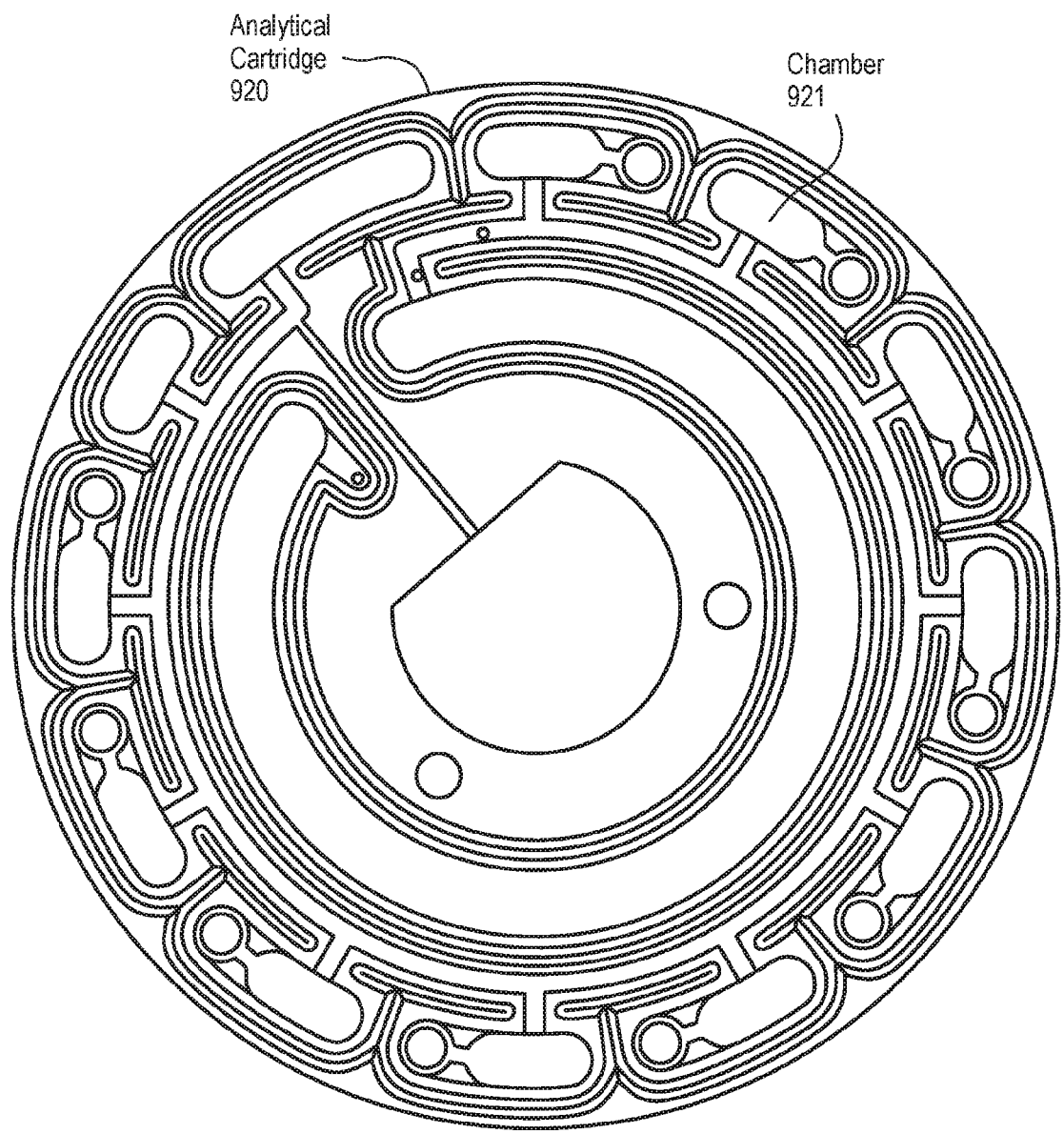
FIG. 19B is a top elevation view of the analytical cartridge of FIG. 19A.

In another embodiment as illustrated in FIGS. 19A and 19B, one or more extractants can be in an analytical cartridge 920, such as described in U.S. Pat. No. 8,734,734. Each chamber 921 of analytical cartridge 920 can have a different extractant. For extractants that can mix easily, the magnetically moveable element may not be needed. Test sample 61 is added to the analytical cartridge 920 and flows to each chamber 921 to mix with the extractant in each chamber 921. Analytical cartridge 920 is spun in a photometer 901, which is in communication with CPU 2820. First, automated gripper 900 receives a signal from CPU 2820 to take an analytical cartridge 920 and insert analytical cartridge 920 into photometer 901. Automated gripper 900 has an automated arm base 902 that is directly or indirectly connected to vehicle 10. An actuator 903 is connected to automated arm base to actuate an automated arm 904. Automated arm 904 has an actuator 905 to actuate grip 906 to grip analytical cartridge 920. Each actuator 903 and 905 are in communication with CPU 2820 to actuate. To add test sample 61, test syringe 922 (which can be similar to syringe 840 above) is moved by automated gripper 900, which is in data communication with CPU 2820. Automated gripper 900 has an automated arm base 902, which is connected directly or indirectly to vehicle 10. An actuator 903 is disposed on automated arm base 902 for actuating automated arm 904. Disposed on automated arm 904 is an actuator 905 actuating grip 906 for gripping analytical cartridge 920. Each actuator 903 and 905 are in communication with CPU 2820 for receiving signals to actuate. A signal is sent to automated gripper 900 to move test syringe 922 into contact with test sample 61. A signal is sent to test syringe 922 to withdraw a specified amount of sample. Automated gripper 900 then receives a signal from CPU 2820 to move test syringe 922 to analytical cartridge 920, and then CPU 2820 sends a signal to test syringe 922 to dispense the sample into analytical cartridge 920. Photometer 901 receives a signal from CPU 2820 to spin analytical cartridge 920 and then measure color in each chamber 921 and communicate the results to CPU 2820. Automated gripper 900 can then receive a signal to move the used analytical cartridge 920 from photometer 901 for disposal.

Figure 21:
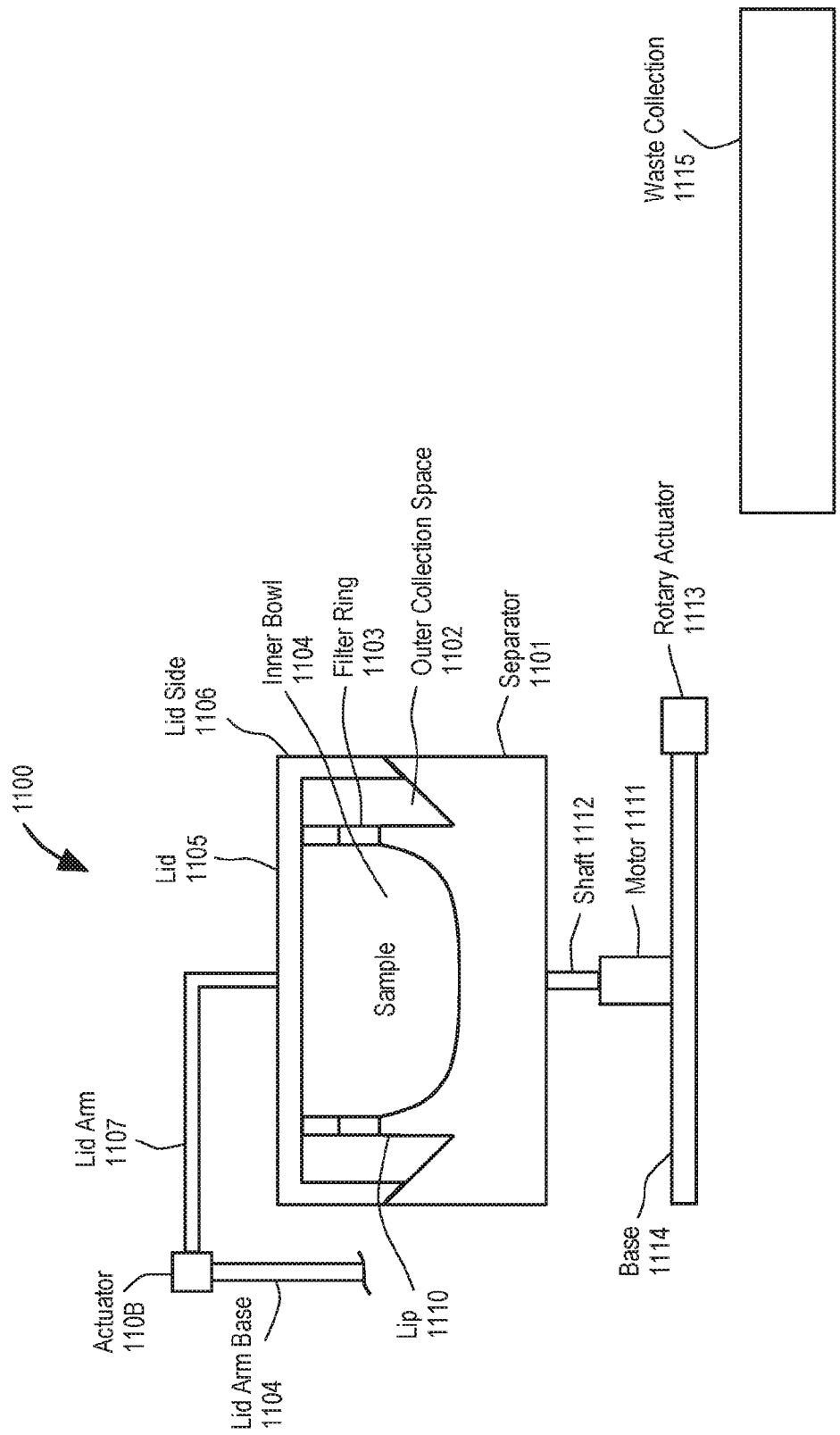
FIG. 21 is a side sectional view of a separator according to one embodiment.

In another embodiment as illustrated in FIG. 21, a separation system 1100 can be included after test sample 61 is prepared above to separate the extracted fluid from the soil and/or vegetation. A separator 1101 has an inner bowl 1104 for receiving samples, and an outer collection space 1102 for collecting filtered samples. Disposed on a lip 1110 between inner bowl 1104 and outer collection space 1102 is a filter ring 1103. A lid 1105 is connected to lid arm 1107, which is connected to an actuator 1108, which is connected to a lid arm base 1104, which is connected directly or indirectly to the vehicle 10. Actuator 1108 is in communication with CPU 2820 to receive signals to raise or lower lid 1105 to engage or disengage from separator 1101. Lid side 1106 extends down to contact separator 1101 at an outer portion of outer collection space 1102 to provide a seal for outer collection space 102. Separator 1101 has a shaft 1112 connected to its bottom, which is driven by motor 1111, which is in communication with CPU 2820 to receive signals to spin separator 11101. Motor 1111 is connected to a base 1114, which is connected to a rotary actuator 1113, which is in communication with CPU 2820. A sample is placed in inner bowl 1104, lid 1105 is engaged with separator 1101, and then separator 1101 is spun. The spinning allows fluid to separate from the sample and flow through filter ring 1103 to the outer collection space 1102. Once separated, separator 1101 is stopped from spinning. Lid 1105 is retracted from separator 1101. Test syringe 922, described above, is inserted into the fluid in outer collection space 1102 to withdraw a test sample 61. Separator 1101 is then emptied of the sample by rotary actuator 1113 receiving a signal from CPU 2820 to rotate the base 1114 such that separator 1101 pours its contents into waste collection 1115. Alternatively, base 1114 and rotary actuator 1113 can be replaced with the rotary actuator 1207, arms 1205-1 and 1205-2 and pivot 1206 described below.

Test samples can be prepared based on a single sample, or multiple samples from multiple points in the field can be combined to provide an average across the multiple points.

Figure 22:
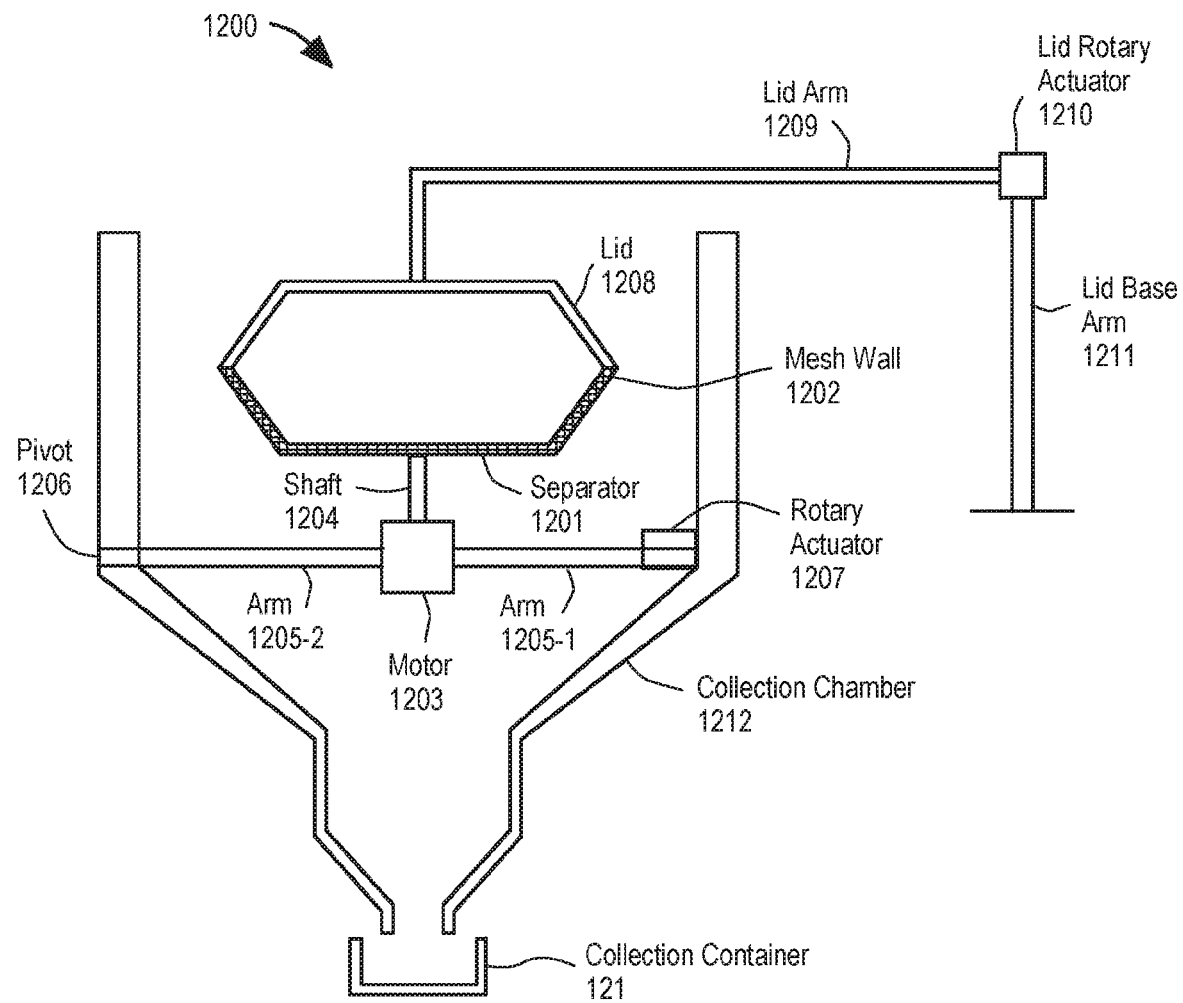
FIG. 22 is a side sectional view of a separator according to one embodiment.

In another embodiment illustrated in FIG. 22, separator system 1200 is described. Separator system 1200 has a collection chamber 1212. Disposed across collection chamber 1212 is a rotary actuator 1207 connected to arm 1205-1, connected to motor 1203, connected to arm 1205-2, connected to pivot 1206. Actuator 1207 and motor 1203 are in communication with CPU 2820. Motor 1203 is connected to a shaft 1204, which is connected to separator 1201. Separator 1201 has a mesh wall 1202 for allowing fluid to flow through it while retaining solids. Engaging separator 1201 is lid 1208. Lid 1208 is connected to lid arm 1209, which is connected to rotary actuator 1210, which is connected to lid base arm 1211, which is directly or indirectly connected to vehicle 10. When a sample is added to separator 1201, CPU 2820 sends a signal to rotary actuator 1210 to close lid 1208. CPU 2820 then sends a signal to motor 1203 to spin separator 1201. Liquid is expelled through mesh wall 1202 into collection chamber 1212 and then drains into collection container 121. When separation is complete, motor 1203 is stopped, and lid 1208 is raised by actuating rotary actuator 1210. After collection container 121 is removed, rotary actuator 1207 is actuated to rotate separator to pour the contents into collection chamber 1212 to flow out the bottom of collection chamber 1212.

Figure 23A:
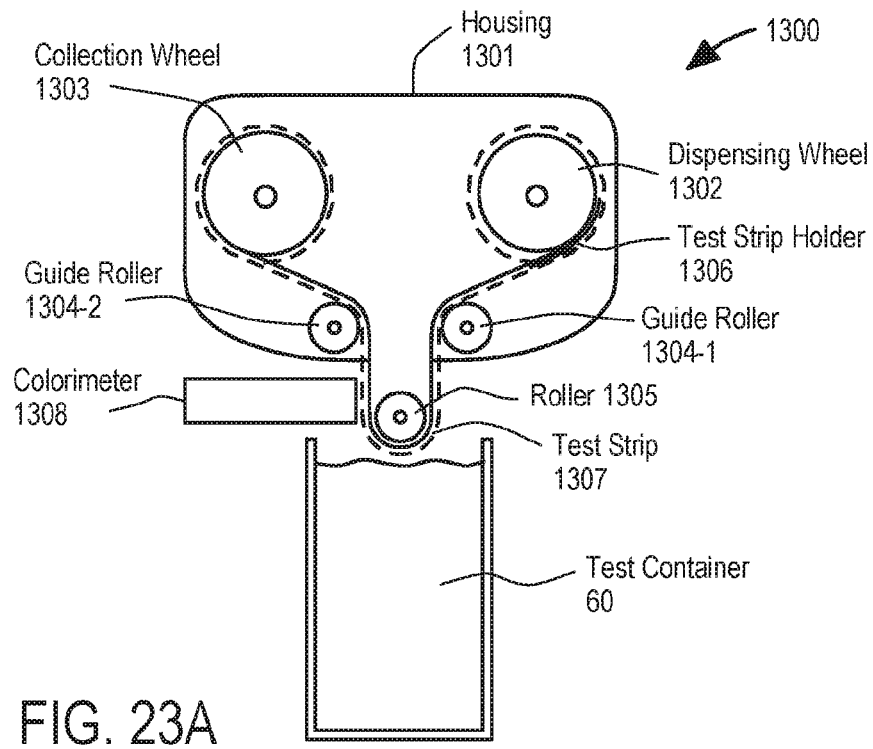
FIG. 23A is a side sectional view of a test strip cassette according to one embodiment.
Figure 23B:
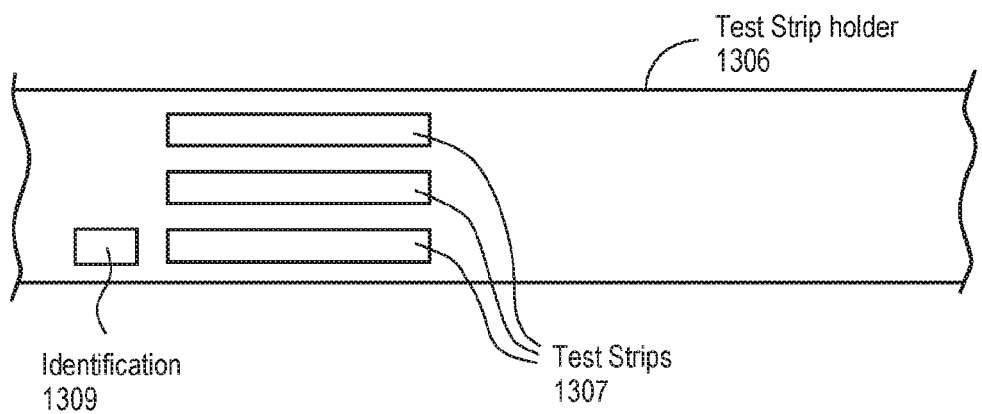
FIG. 23B is a top elevation view of a test strip holder with test strips according to one embodiment.
Figure 23C:
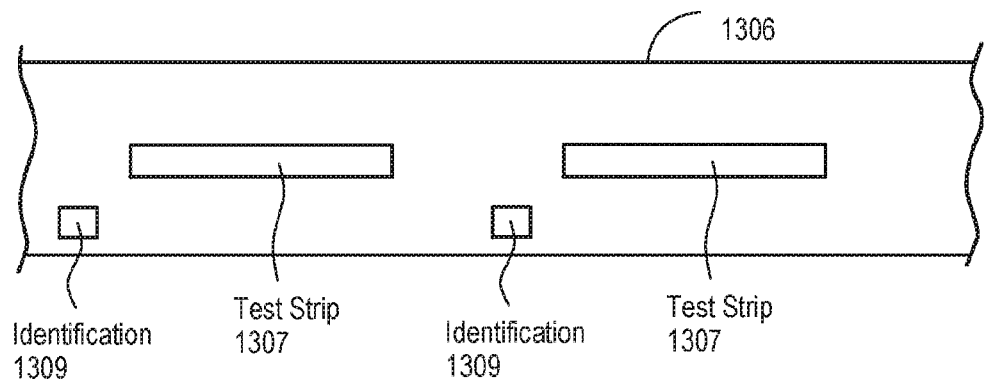
FIG. 23C is a top elevation view of a test strip holder with test strips according to one embodiment.

In one embodiment, a test strip apparatus 1300 is used to test the test sample 61. As illustrated in FIG. 23, test strip apparatus 1300 includes a test strip holder 1306 loaded onto dispensing wheel 1302 and wound around a roller 1305 to a collection wheel 1303. Roller 1305 allows for test strip holder 1306 to be positioned to allow for the test strip holder 1306 to be placed in test sample 61. Optionally, guide rollers 1304-1, 1304-2 can be included to further guide test strip holder 1306. A motor (not shown) drives collection wheel 1303 to pull test strip holder from dispensing wheel 1302. The motor can be an electrical motor or an electromechanical motor, and it is in data communication with CPU 2820 for controlling the advancement of test strip holder 1306 to the next available test strip 1307 for testing samples.

On test strip holder 1306 are test strips 1307 that are chemically reactive to selected chemicals and change color based on the chemical concentration in the test solution. Each test strip 1307 has an identification 1309 that is associated with a geo-referenced location of a test sample 61 that is tested by test strip 1307. When multiple test strips 1307 are used to test sample 61 (such as with different chemicals), test strips 1307 can share the same identification 1309 or each can have its own identification 1309. Test strip holder 1306 can hold multiple types of test strips 1307 for testing different chemicals. Test strips 1307 for different chemicals can be disposed side by side of each other on test strip holder 1306, or they can be disposed sequentially along test strip holder 1306.

If not already set to have an untested test strip 1307, collection wheel 1303 is advanced to have an untested test strip 1304 positioned at roller 1305. Test strip apparatus 1300 can be lowered to submerge test strip 1307 at roller 1305 into sample container 50, or sample container 50 can be raised to submerge test strip 1307. Test strip 1307 remains submerged in test sample 61 in sample container 50 for a specified amount of time for test strip 1307 to react with the test sample 61. The amount of time varies based on the type of chemical tested. After the amount of time has been reached, test strip 1307 is removed from test sample 61 by either raising test strip apparatus 1300 or lowering sample container 50. Test sample 61 is then disposed of. If the extractant is water, test sample 61 can be drained to the ground, or test sample 61 can be transferred to a disposal container (not shown) for later disposal. Sample container 50 is then rinsed with water and is ready for another sample.

In another embodiment as shown in FIGS. 24A to 24E, a reel 1402 has a pouch strip 1401 wound onto reel 1402. Pouch strip 1401 has pouches 1403 disposed within it. Each pouch 1403 has a reagent stored within the pouch 1403. On each side of pouch strip 1403, there are drive strips 1405-1 and 1405-2. In one embodiment, each drive strip 1405-1 and 1405-2 can be driven by strip drive wheels 1406-1 and 1406-2 by friction. In another embodiment, at least one drive strip 1405-1 and 1405-2 contains sprocket holes 1407-1 and 1407-2 to be driven by at least one sprocket drive wheel 1707 as illustrated in FIG. 24E.

To add test sample 61, test syringe 1402 (which can be similar to syringe 840 above) is moved by a similar system that moves syringe 840.

In one embodiment, a colorimeter 1308 can be included to read the color of each test strip 1307 after it leaves test sample 61 and before winding onto collection wheel 1303, which is enclosed within housing 1301. Colorimeter 1308 can then be in data communication with memory storage 2805 and CPU 2820. Alternatively, test strip holder 1306 can be collected and tested after all sampling is completed. In any of these embodiments, a data map 10003 can be generated that associates test results for each chemical tested at each location in the field. The identification can be any identification that uniquely identifies the sample tested. The identification includes, but is not limited to, an alpha indicia, a numeric indicia, an alphanumeric indicia, a bar code, or a QR code.

In other embodiments, test strip apparatus 1300 and colorimeter 1308 are replaced by one or more ion-selective electrodes (not shown) that are immersed in test sample 61. Ion-selective electrodes are in data communication with CPU 2820 and memory 2805 to record the results for each sample tested. In other embodiments, a spectrophotometer (not shown) is used to analyze the samples. The spectrophotometer is in data communication with CPU 2820 and memory 2805.

Figure 26:
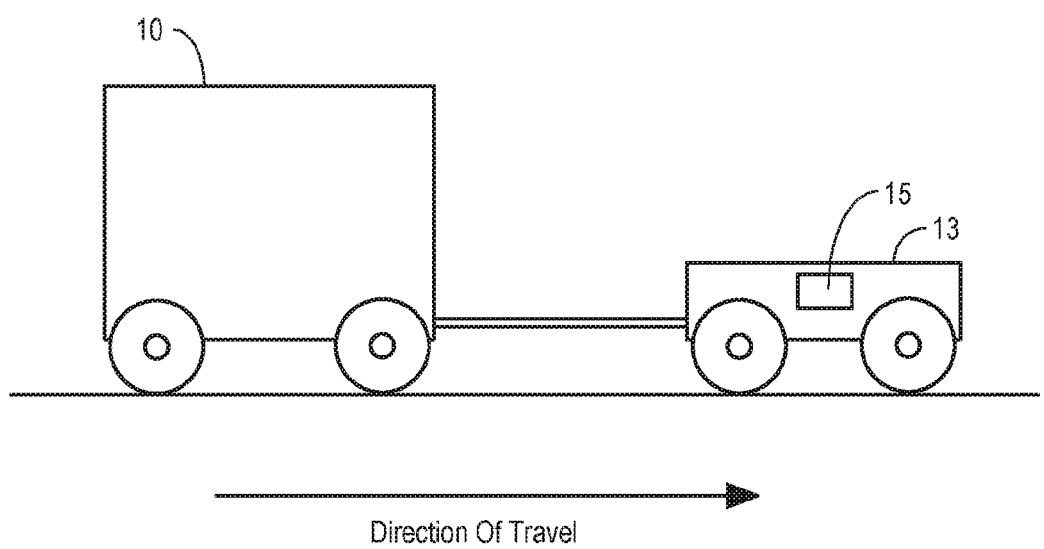
FIG. 26 is a side elevation view of a vehicle with a cart disposed ahead of the vehicle with collection, processing, and testing according to one embodiment

In one embodiment, the collection system 15 can be disposed on the front of vehicle 10 in a direction of travel (not shown) or ahead of vehicle 10 in a direction of travel on a cart 13 as illustrated in FIG. 26. Cart 13 can also have any of the above described equipment to process and/or test samples. Having the collection system 15 ahead of vehicle 10 allows for testing of soil and/or vegetation to provide data about the tested property to then change an agricultural operation on the vehicle 10. For example, an amount of a nutrient being applied to the field by vehicle 10 can be varied based on an amount needed for the specific location. In this embodiment, it is not necessary to associate the test strip 1307 with the identification 1309 since the test results are immediately used to change the agricultural operation. While not required, it is preferable to include the identification 1309 to so that a map can be created.

Figure 25:
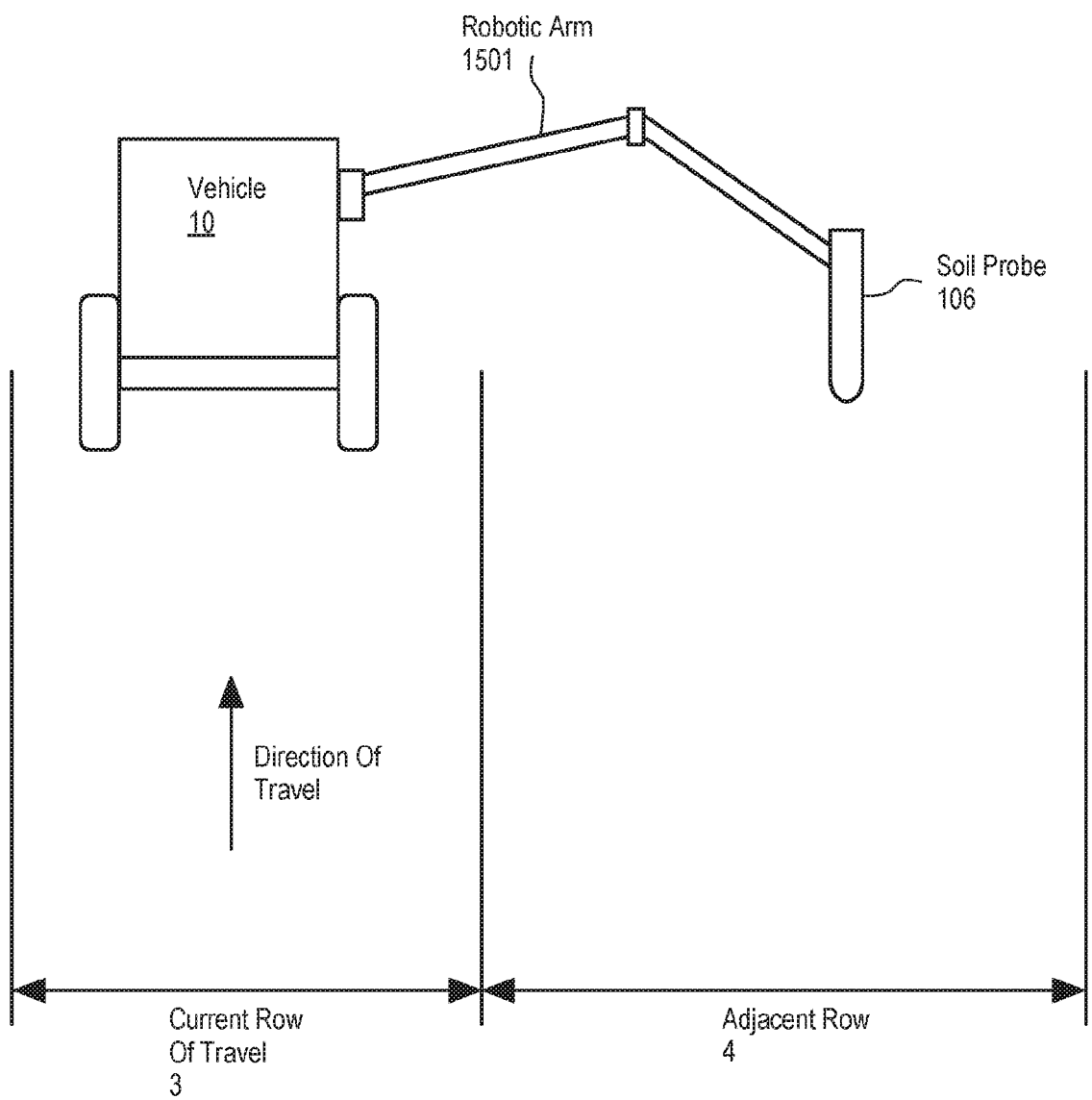
FIG. 25 is a rear elevation view of a vehicle with soil probe according to one embodiment.

As illustrated in FIG. 25, collection system 15 can be configured to sample in a row adjacent to the current rows of travel. This provides time to process and test the sample to obtain a result that can be used to change an agricultural function on the vehicle 10 as vehicle 10 crosses the point. As shown in FIG. 25, any of the soil probes (e.g., 106) described above can be mounted to robotic arm 1501. Robotic arm 1501 is mounted to vehicle 10 and extends to an adjacent row 4. Robotic arm 1501 is in communication with CPU 2820. CPU 2820 sends a signal to robotic arm 1501 to extend to adjacent row 4 and to lower soil probe 106 into soil. Robotic arm 1501 then receives a signal from CPU 2820 to move robotic arm 1501 to vehicle 10 to have the soil collected in collection container 121 as described above.

To facilitate the time it takes to process and then test soil and/or vegetation samples, provided are multiple testing systems each working in parallel to test samples while still collecting additional samples. Optionally, there can be multiple processing systems. The number of processing systems and testing systems can be chosen to account for the maximum speed of vehicle 10 during sampling and the number of samples to be taken per area. Depending on timing, one processing system 17 can process all samples for testing in testing system 16. Described herein is a system with multiple processing systems 2801. CPU 2820 can send a signal to collection system 15 to actuate and collect a sample and then deliver the sample to a first processing system 2801. CPU 2820 can then send a signal to processing system 2801 to process the sample. In the meantime, CPU 2820 can send a signal to collection system 15 to collect another sample and then deliver the sample to a second processing system 17-2. As each processing system 17 completes processing, which can be based on a fixed amount of time, the sample can be transferred to via a transfer system (such as shown in FIG. 1A to 12B) to an available testing system 16. A signal is sent from CPU 2820 to the transfer system to retrieve the sample. Once retrieved, CPU 2820 signals the transfer system to transfer the sample to an available testing system 16.

Figure 27A:
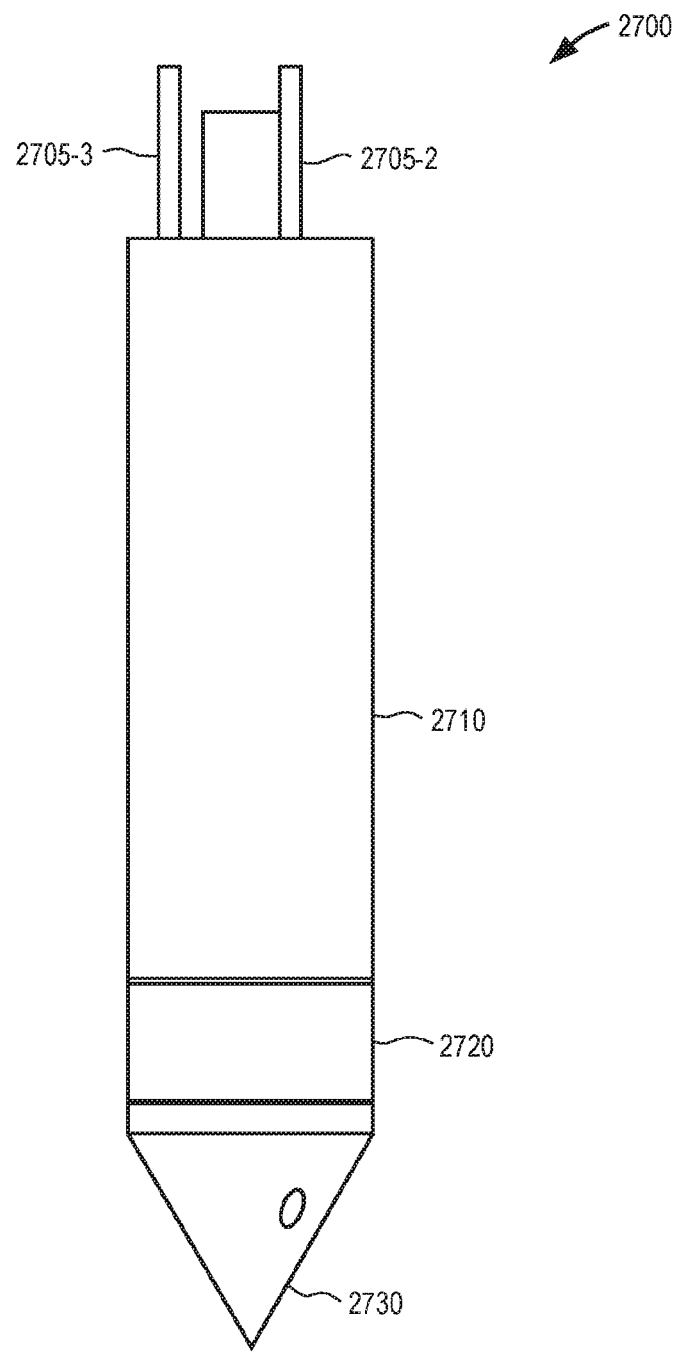
FIG. 27A is a side view of a sample probe according to one embodiment.

A sample probe according to another embodiment is illustrated in FIG. 27A. Sample probe 2700 allows for the collection of solid soil, fluidization of the solid soil, and then pumping of the fluidized sample. This simplifies the system by eliminating mechanical transfer of samples from soil probes to other parts of the system. Sample probe 2700 has three components: a first body 2710, a second body 2720, and a center body 2730. First body 2710 and second body 2720 are connected together (not shown) by a fastener, such as a screw/bolt.

Figure 27B:
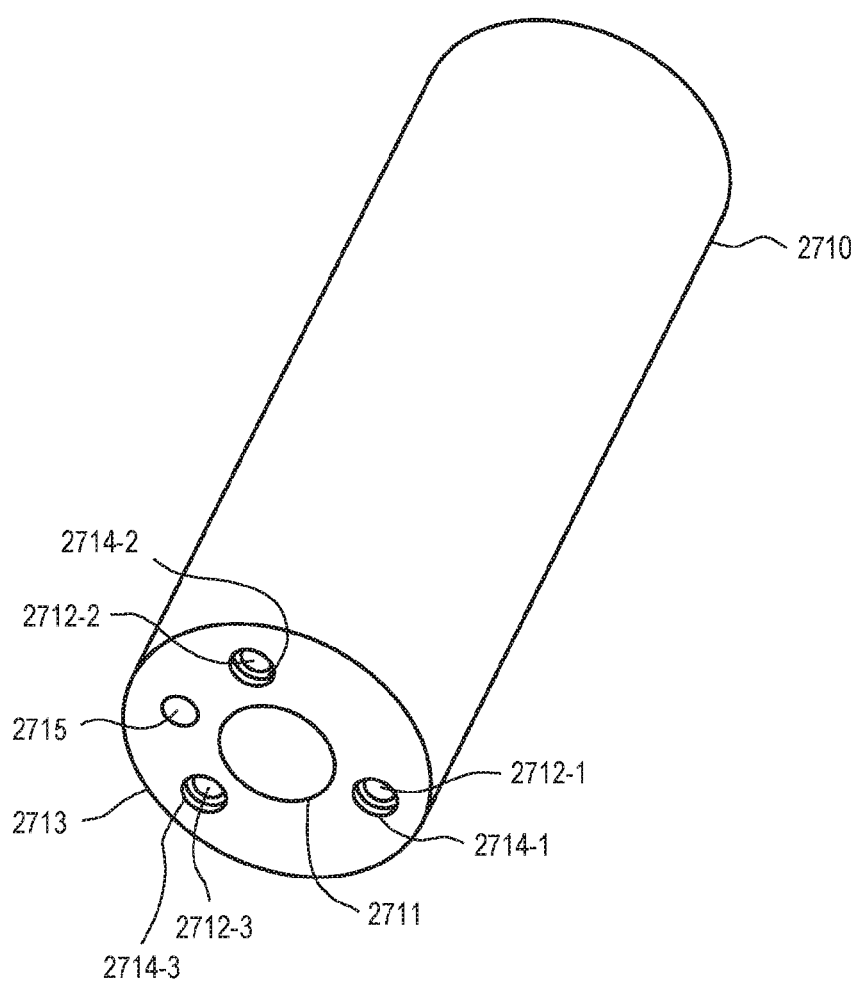
FIG. 27B is a perspective view of a first body of the sample probe of FIG. 27A.

As illustrated in FIG. 27B, first body 2710 in one embodiment has a cylindrical shape. Disposed through a center of first body 2710 is a center body conduit 2711. Disposed through first body 2710 are piston conduits 2712. There can be any number of piston conduits from 1 to a maximum number that can fit around first body 2710. As illustrated, there are three piston conduits 2712-1, 2712-2, and 2712-3. At the bottom 2714 of first body 2710 there can be o-ring seats 2714-1, 2714-2, and 2714-3 for piston conduits 2712-1, 2712-2, and 2712-3, respectively. Also, disposed through first body 2710 is a fluid conduit 2715.

Figure 27C:
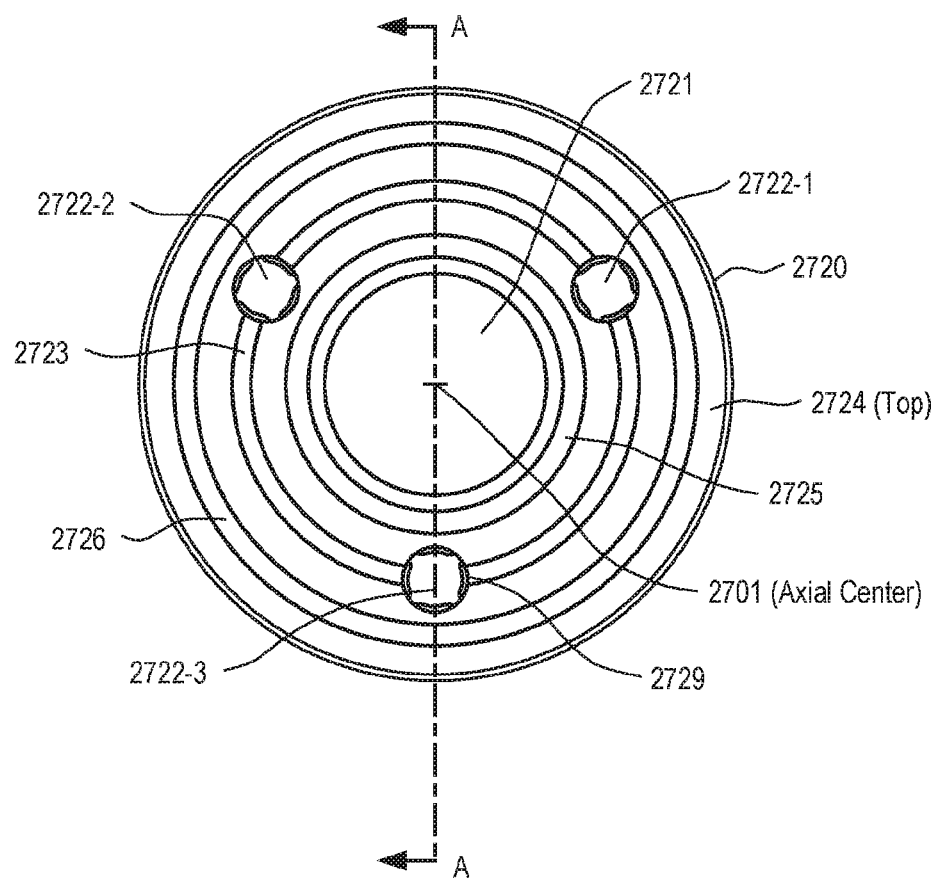
FIG. 27C is a top view of the second body of the sample probe of FIG. 27A.
Figure 27D:
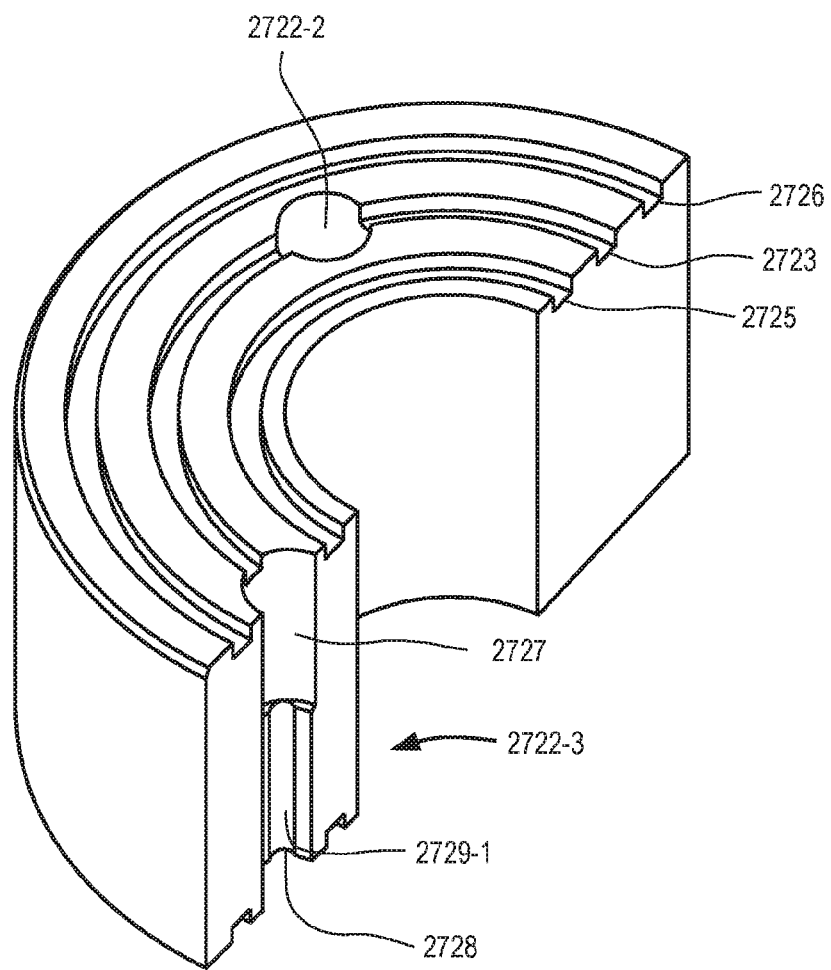
FIG. 27D is a top perspective section view of the second body of the sample probe of FIG. 27A taken along line A-A.
Figure 27E:
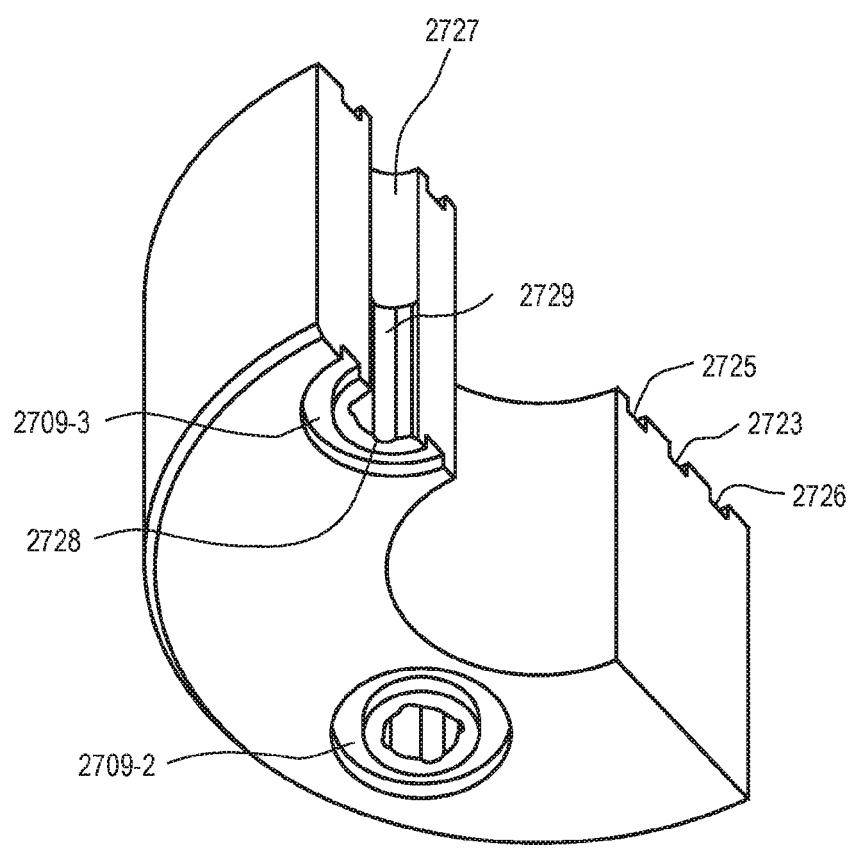
FIG. 27E is a bottom perspective section view of the second body of the sample probe of FIG. 27A taken along line A-A.

As illustrated in FIGS. 27C to 27E, second body 2720 has a center body conduit 2721 that aligns with first body conduit 2711. Second body has piston conduits 2722 that match in number and alignment to the piston conduits 2712 of the first body. As shown, there are three piston conduits, 2722-1, 2722-2, and 2722-3. Piston conduits 2712-1, 2712-2, 2712-3, 2722-1, 2722-2, and 2722-3 all are disposed the same radial distance from the axial center 2701 of sample probe 2700.

There is a fluid channel 2723 disposed in the top 2724 of second body 2720. The fluid channel 2723 is in fluid communication with piston conduits 2722-1, 2722-2, and 2722-3. Fluid conduit 2715 terminates and is in fluid communication with fluid channel 2723. In one embodiment, there are an inner o-ring seat 2725 for accepting an o-ring and an outer o-ring seat 2726 for accepting an o-ring. The o-ring seats 2725 and 2726 provide a seal to fluid channel 2723. As best seen in FIGS. 27D and 27E, piston conduits 2722-1, 2722-2, and 2722-3 have a first diameter 2727 that extends partially through second body 2720 and a second diameter 2728 that extends the remaining distance through second body 2720. The diameter of second diameter 2728 is approximately the same as the outer diameter of pistons 2705. The first diameter 2720 is greater than the second diameter 2728. Fluid from fluid channel 2723 is able to flow into first diameter 2727 of piston conduits 2722. Disposed coaxially along second diameter 2728 are one or more slots 2729. As shown, there are four slots 2729 in each piston channel 2722. The slots 2729 provide fluid communication from the first diameter 2727 through the second body 2720 such that a radius of first diameter 2727 and a radius of slot 2729. There can be an o-ring that sits in an o-ring seat 2709-1, 2709-2, and 2709-3 disposed around the outlets for piston conduits 2722-1, 2722-2, and 2722-3.

Figure 27F:
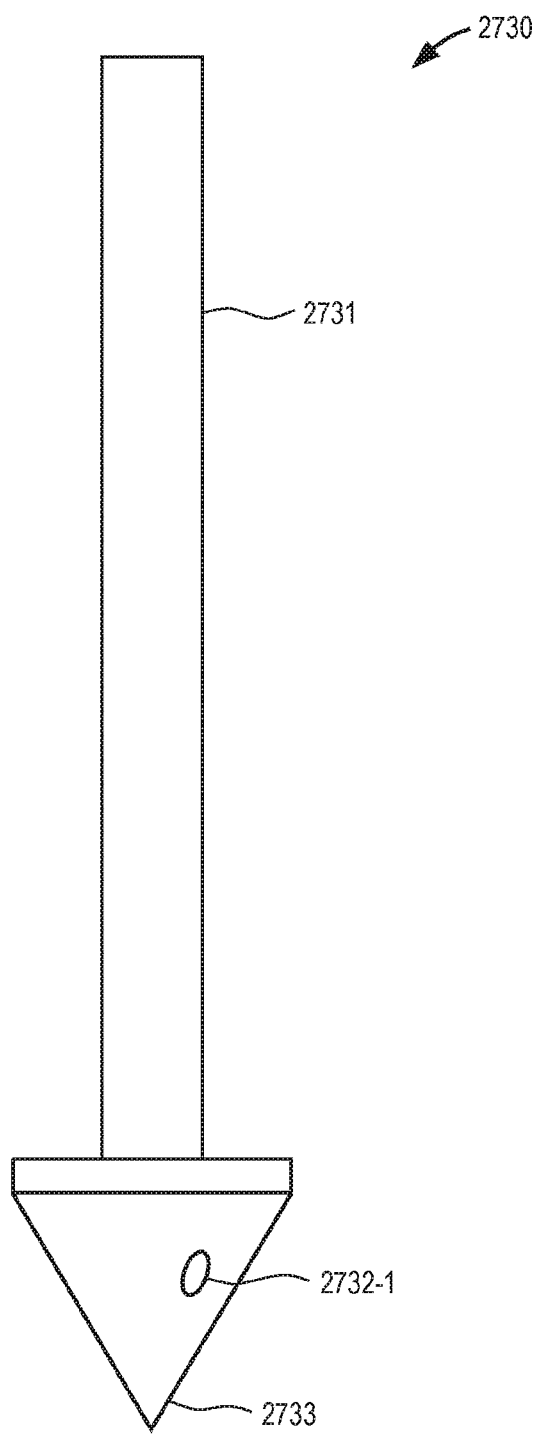
FIG. 27F is a perspective view of the central body of the sample probe of FIG. 27A.
Figure 27G:
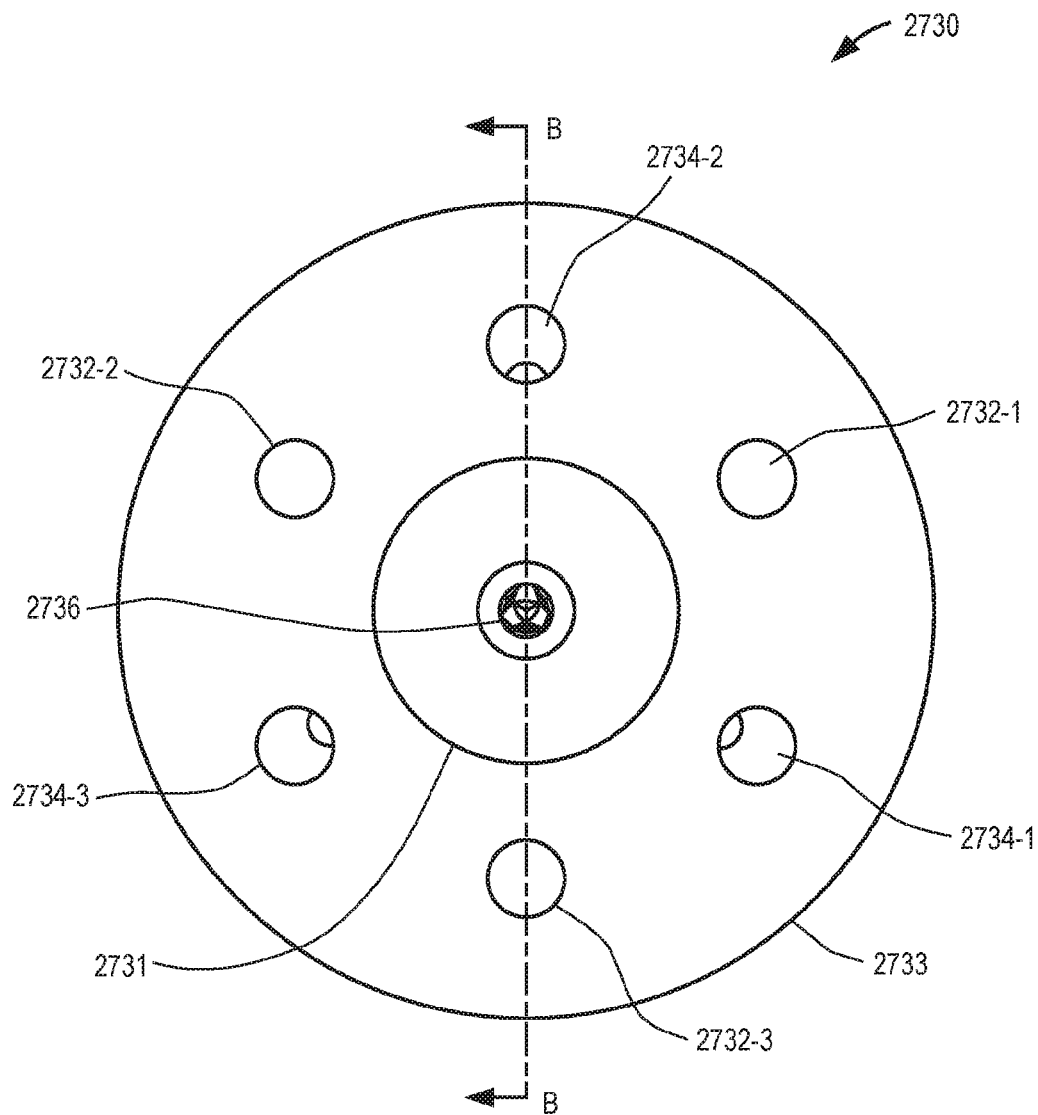
FIG. 27G is a top view of the central body of the sample probe of FIG. 27A.
Figure 27H:
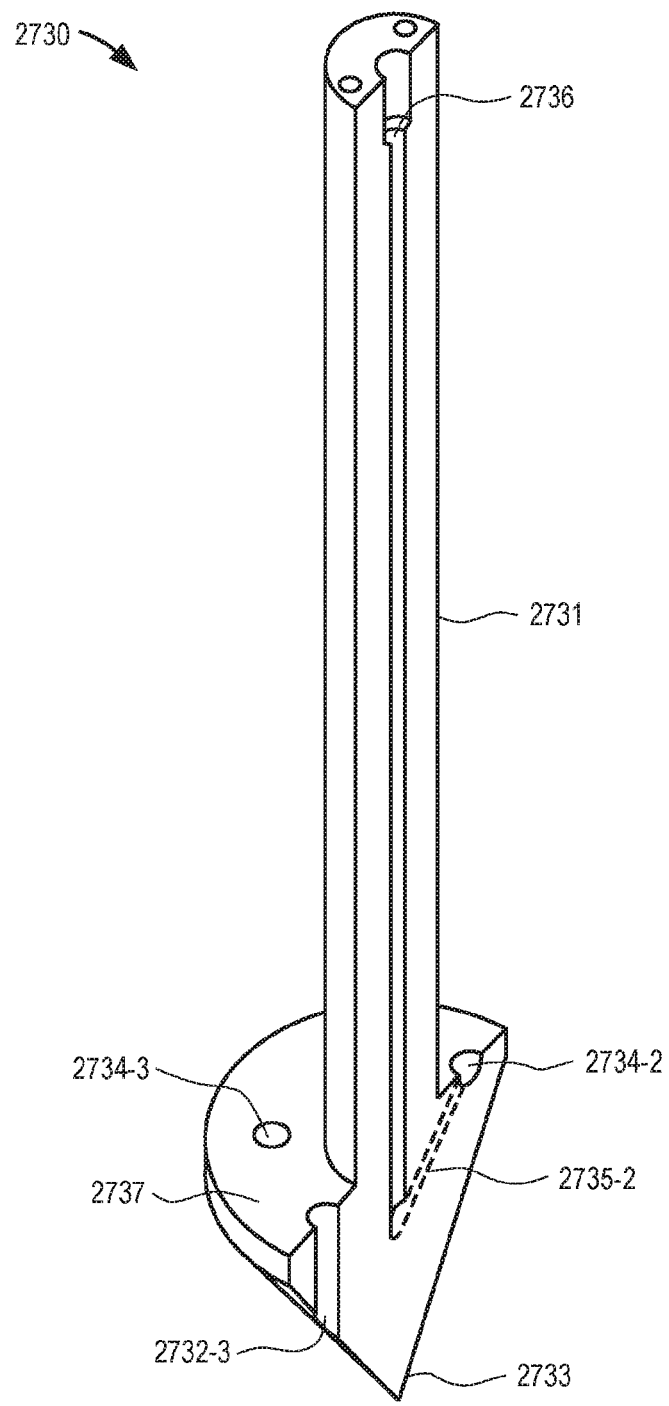
FIG. 27H is a perspective section view of the central body of FIG. 27A taken along line B-B.

The center body 2730 is illustrated in FIGS. 27F to 27H. Center body 2730 has a shaft 2731 whose outside diameter is the same as the diameter of center body conduit 2711 and center body conduit 2712. Shaft 2731 is connected to a tip 2733. Tip 2733 is a cone whose base is the same diameter as first body 2710 and 2720 and tapers to a point. Piston conduits 2732-1, 2732-2, and 2732-3 are disposed through tip 2733. Disposed through shaft 2731 and into tip 2733 is sample fluid conduit 2736. Sample fluid conduit 2736 is in fluid communication with processing or testing systems. In the top 2737 of tip 2733 are fluid inlet ports 2734-1, 2734-2, and 2734-3, which are in fluid communication with fluid conduits 2735-1, 2735-2, and 2735-3, respectively. Fluid conduits 2735-1, 2735-2, and 2735-3 are in fluid communication with sample fluid conduit 2736.

Pistons 2705-1, 2705-2, and 2705-3 are disposed through piston conduits 2712-1, 2712-2, 2712-3, 2722-1, 2722-2, 2722-3, 2732-1, 2732-2, and 2732-3, respectively, and they are driven by linear actuators, not shown, to raise and lower the pistons 2705-1, 2705-2, and 2705-3. In one embodiment, the pistons 2705-1, 2705-2, and 2705-3 operate in unison. Center body 2730 is rotatable by a rotary actuator, not shown. Pistons 2705-1, 2705-2, and 2705-3 can have ends that are flat or pointed, or any shape that can assist in mixing. Also, pistons 2705-1, 2705-2, and 2705-3 can be an ultrasonic horn to break up soil and assist in mixing.

In operation, center body 2730 is rotated so that piston conduits 2722-1, 2722-2, 2722-3 are aligned with piston conduits 2732-1, 2732-2, and 2732-3, respectively. Pistons 2705-1, 2705-2, and 2705-3 are retracted so that a desired void volume is formed in piston conduits 2722-1, 2722-2, 2722-3, 2732-1, 2732-2, and 2732-3, and optionally 2712-1, 2712-2, 2712-3. Alternatively, pistons 2705-1, 2705-2, and 2705-3 can be fully extended to outlets of 2732-1, 2732-2, and 2732-3 first. Soil probe 2700 is plunged into soil (and pistons 2732-1, 2732-2, and 2732-3 are retracted if not already retracted), and soil fills piston conduits 2722-1, 2722-2, 2722-3, 2732-1, 2732-2, and 2732-3, and optionally 2712-1, 2712-2, 2712-3. At this point, pistons 2732-1, 2732-2, and 2732-3 are not in piston conduits 2732-1, 2732-2, and 2732-3. Center body 2730 is then rotated so that piston conduits 2722-1, 2722-2, 2722-3 are not in communication with piston conduits 2732-1, 2732-2, and 2732-3 and fluid inlet ports 2734-1, 2734-2, and 2734-3. Pistons 2705-1, 2705-2, and 2705-3 are extended downward to compact the soil in piston conduits 2722-1, 2722-2, 2722-3. Center body 2730 is then rotated such that piston conduits 2722-1, 2722-2, 2722-3 and piston conduits 2732-1, 2732-2, and 2732-3 are aligned. Pistons 2705-1, 2705-2, and 2705-3 are actuated downward to a specified distance so that a known volume of soil in piston conduits 2722-1, 2722-2, 2722-3 is obtained. This expels any excess soil through piston conduits 2732-1, 2732-2, and 2732-3. Center body 2730 is then rotated to align piston conduits 2722-1, 2722-2, 2722-3 with fluid inlet ports 2734-1, 2734-2, and 2734-3, respectively. Fluid (such as extractant or other fluid, such as water) is injected through fluid conduit 2715 which communicates fluid to fluid channel 2723 which communicates fluid into piston conduits 2722-1, 2722-2, 2722-3 and slots 2729. Optionally, pistons 2705-1, 2705-2, and 2705-3 can be oscillated up and down and/or rotated at any specified frequency to facilitate mixing of fluid with the soil. As the soil becomes fluidized, fluidized soil flows into fluid inlet ports 2734-1, 2734-2, and 2734-3 to fluid conduits 2735-1, 2735-2, and 2735-3, respectively, and then into sample fluid conduit 2736. Fluid flow is stopped, and then center body 2730 is rotated to align piston conduits 2722-1, 2722-2, 2722-3 with piston conduits 2732-1, 2732-2, and 2732-3, and the pistons are extended to expel any remaining soil.

In an alternative embodiment, sample probe 2700 can be operated with the reverse flow of fluid. Fluid can flow from fluid conduit 2736 to fluid conduits 2735-1, 2735-2, and 2735-3 and then enter piston conduits 2722-1, 2722-2, and 2722-3 from the bottom and flow up to fluid channel 2723 and then to fluid conduit 2715. In this embodiment, slots 2729 act like a screen by only permitting soil that is sized to move through slots 2729. In this embodiment, oscillation of pistons 2705-1, 2705-2, and 2705-3 can draw fluid up to the top of soil and dissolve the soil in the fluid. This can minimize the amount of fluid needed to fluidize the soil.

Figure 28:
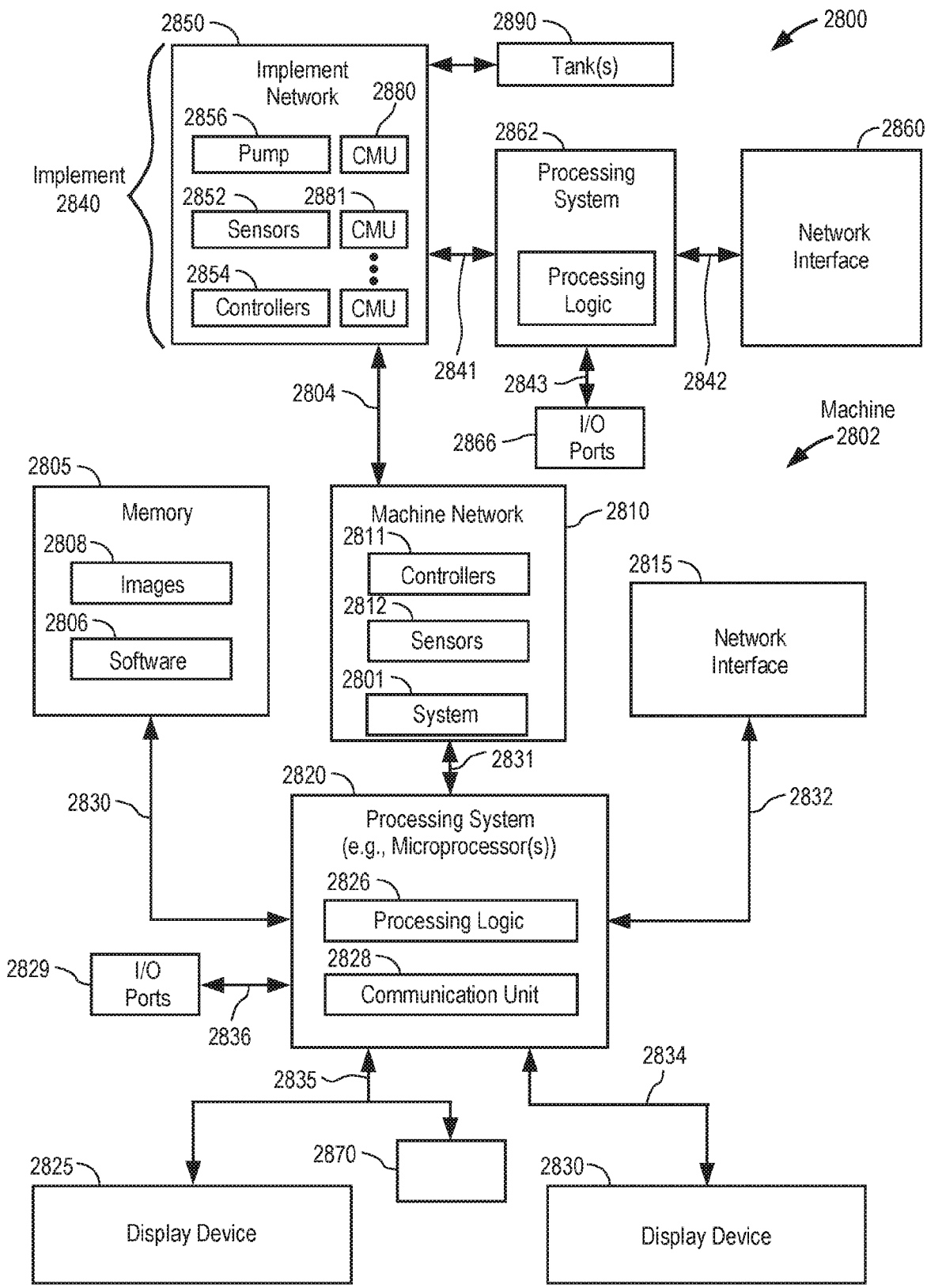
FIG. 28 shows an example of a system 2800 that includes a machine 2802 (e.g., vehicle, tractor, combine harvester, etc.) and an implement 2840 (e.g., planter, cultivator, plough, sprayer, spreader, irrigation implement, etc.) in accordance with one embodiment.

FIG. 28 shows an example of a system 2800 that includes a machine 2802 (e.g., vehicle, tractor, combine harvester, etc.) and an implement 2840 (e.g., planter, cultivator, plough, sprayer, spreader, irrigation implement, etc.) in accordance with one embodiment. The machine 2802 includes a processing system 2820, memory 2805, machine network 2810 (e.g., a controller area network (CAN) serial bus protocol network, an ISOBUS network, etc.), and a network interface 2815 for communicating with other systems or devices including the implement 2840. The machine network 2810 includes sensors 2812 (e.g., sensors for measuring properties of soil and vegetative samples, speed sensors, etc.), controllers 2811 (e.g., GPS receiver, radar unit) for controlling and monitoring operations of the machine or implement. The network interface 2815 can include at least one of a GPS transceiver, a WLAN transceiver (e.g., WiFi), an infrared transceiver, a Bluetooth transceiver, Ethernet, or other interfaces from communications with other devices and systems including the implement 2840. The network interface 2815 may be integrated with the machine network 2810 or separate from the machine network 2810 as illustrated in FIG. 28. The I/O ports 2829 (e.g., diagnostic/on board diagnostic (OBD) port) enable communication with another data processing system or device (e.g., display devices, sensors, etc.).

In one example, the machine performs operations of a tractor or vehicle that is coupled to an implement for agricultural operations. The processing system 2820 may include one or more microprocessors, processors, a system on a chip (integrated circuit), or one or more microcontrollers. The processing system includes processing logic 2826 for executing software instructions of one or more programs and a communication unit 2828 (e.g., transmitter, transceiver) for transmitting and receiving communications from the machine via machine network 2810 or network interface 2815 or implement via implement network 2850 or network interface 2860. The communication unit 2828 may be integrated with the processing system or separate from the processing system. In one embodiment, the communication unit 2828 is in data communication with the machine network 2810 and implement network 2850 via a diagnostic/OBD port of the I/O ports 2829.

Processing logic 2826 including one or more processors may process the communications received from the communication unit 2828 including agricultural data (e.g., test data, testing results, GPS data, liquid application data, flow rates, etc.). The system 2800 includes memory 2805 for storing data and programs for execution (software 2806) by the processing system. The memory 2805 can store, for example, software components such as testing software for analysis of soil and vegetation samples for performing operations of the present disclosure, or any other software application or module, images (e.g., captured images of crops), alerts, maps, etc. The memory 2805 can be any known form of a machine readable non-transitory storage medium, such as semiconductor memory (e.g., flash; SRAM; DRAM; etc.) or non-volatile memory, such as hard disks or solid-state drive. The system can also include an audio input/output subsystem (not shown) which may include a microphone and a speaker for, for example, receiving and sending voice commands or for user authentication or authorization (e.g., biometrics).

In the embodiments with sampling system 2801 (e.g., processing system 2801), vehicle 2802 (e.g., machine 2802) can further include a sensing system 2812 or be coupled to an implement 2840 that includes a sensing system 2852. Sensing system (e.g., sensing system 2812, sensing system 2852) is in data communication with processing system 2820 (e.g., microprocessor(s), CPU). Additional data at each point sampled can be tested by the sensing system. Sensing system can include one or more of the following: spectrographic measurement, electrical conductivity, apparent electrical conductivity, LIDAR, radar, ground penetrating radar, sonar, optical height, camera, time of flight camera. Examples of spectrographic measurement include, but are not limited to, visible light, laser, near-infrared, infrared, transient infrared spectroscopy, RAMAN spectroscopy, ultraviolet, and x-ray. The combination of soil and/or vegetation sampling along with sensing can provide a more detailed analysis of the conditions in the field.

The processing system 2820 communicates bi-directionally with memory 2805, machine network 2810, network interface 2815, display device 2830, display device 2825, and I/O ports 2829 via communication links 2830-2836, respectively.

Display devices 2825 and 2830 can provide visual user interfaces for a user or operator. The display devices may include display controllers. In one embodiment, the display device 2825 is a portable tablet device or computing device with a touchscreen that displays data (e.g., test results of soil, test results of vegetation, liquid application data, captured images, localized view map layer, high definition field maps of as-applied liquid application data, as-planted or as-harvested data or other agricultural variables or parameters, yield maps, alerts, etc.) and data generated by an agricultural data analysis software application and receives input from the user or operator for an exploded view of a region of a field, monitoring and controlling field operations. The operations may include configuration of the machine or implement, reporting of data, control of the machine or implement including sensors and controllers, and storage of the data generated. The display device 2830 may be a display (e.g., display provided by an original equipment manufacturer (OEM)) that displays images and data for a localized view map layer, as-applied liquid application data, as-planted or as-harvested data, yield data, controlling a machine (e.g., planter, tractor, combine, sprayer, etc.), steering the machine, and monitoring the machine or an implement (e.g., planter, combine, sprayer, etc.) that is connected to the machine with sensors and controllers located on the machine or implement.

A cab control module 2870 may include an additional control module for enabling or disabling certain components or devices of the machine or implement. For example, if the user or operator is not able to control the machine or implement using one or more of the display devices, then the cab control module may include switches to shut down or turn off components or devices of the machine or implement.

The implement 2840 (e.g., planter, cultivator, plough, sprayer, spreader, irrigation implement, etc.) includes an implement network 2850, a processing system 2862, a network interface 2860, and optional input/output ports 2866 for communicating with other systems or devices including the machine 2802. In one example, the implement network 2850 (e.g., a controller area network (CAN) serial bus protocol network, an ISOBUS network, etc.) includes a pump 2856 for pumping liquid from a storage tank(s) 2890 to control monitoring units (CMUs) 2880, 2881, . . . N of the implement, sensors or sensing system 2852 (e.g., soil sensors, vegetation sensors, soil probe, speed sensors, seed sensors for detecting passage of seed, downforce sensors, actuator valves, OEM sensors, flow sensors, etc.), controllers 2854 (e.g., GPS receiver), and the processing system 2862 for controlling and monitoring operations of the machine. The CMUs control and monitor the application of the liquid to crops or soil as applied by the implement. The liquid application can be applied at any stage of crop development including within a planting trench upon planting of seeds, adjacent to a planting trench in a separate trench, or in a region that is nearby to the planting region (e.g., between rows of corn or soybeans) having seeds or crop growth. Alternatively, solids can be applied via the spreader.

The OEM sensors may be moisture sensors or flow sensors for a combine, speed sensors for the machine, seed force sensors for a planter, liquid application sensors for a sprayer, or vacuum, lift, lower sensors for an implement. For example, the controllers may include processors in communication with a plurality of seed sensors. The processors are configured to process data (e.g., testing data for soil and vegetation, liquid application data, seed sensor data) and transmit processed data to the processing system 2862 or 2820. The controllers and sensors may be used for monitoring motors and drives on a planter including a variable rate drive system for changing plant populations. The controllers and sensors may also provide swath control to shut off individual rows or sections of the planter. The sensors and controllers may sense changes in an electric motor that controls each row of a planter individually. These sensors and controllers may sense seed delivery speeds in a seed tube for each row of a planter.

The network interface 2860 can be a GPS transceiver, a WLAN transceiver (e.g., WiFi), an infrared transceiver, a Bluetooth transceiver, Ethernet, or other interfaces from communications with other devices and systems including the machine 2802. The network interface 2860 may be integrated with the implement network 2850 or separate from the implement network 2850 as illustrated in FIG. 28.

The processing system 281262 communicates bi-directionally with the implement network 2850, network interface 2860, and I/O ports 2866 via communication links 2841-2843, respectively.

The implement communicates with the machine via wired and possibly also wireless bi-directional communications 2804. The implement network 2850 may communicate directly with the machine network 2810 or via the networks interfaces 2815 and 2860. The implement may also by physically coupled to the machine for agricultural operations (e.g., planting, harvesting, spraying, etc.).

The memory 2805 may be a machine-accessible non-transitory medium on which is stored one or more sets of instructions (e.g., software 2806) embodying any one or more of the methodologies or functions described herein. The software 2806 may also reside, completely or at least partially, within the memory 2805 and/or within the processing system 2820 during execution thereof by the system 2800, the memory and the processing system also constituting machine-accessible storage media. The software 2806 may further be transmitted or received over a network via the network interface 2815.

In one embodiment, a machine-accessible non-transitory medium (e.g., memory 2805) contains executable computer program instructions which when executed by a data processing system cause the system to performs operations or methods of the present disclosure including measuring properties and testing of soil and vegetative samples. While the machine-accessible non-transitory medium (e.g., memory 1205) is shown in an exemplary embodiment to be a single medium, the term "machine-accessible non-transitory medium" should be taken to include a single medium or multiple media (e.g., a centralized or distributed database, and/or associated caches and servers) that store the one or more sets of instructions. The term "machine-accessible non-transitory medium" shall also be taken to include any medium that is capable of storing, encoding or carrying a set of instructions for execution by the machine and that cause the machine to perform any one or more of the methodologies of the present disclosure. The term "machine-accessible non-transitory medium" shall accordingly be taken to include, but not be limited to, solid-state memories, optical and magnetic media, and carrier wave signals.

Data from soil and/or vegetation sampling can be used to generate a map of the field to be used later during an agricultural operation, such as nutrient application.

Figure 29:
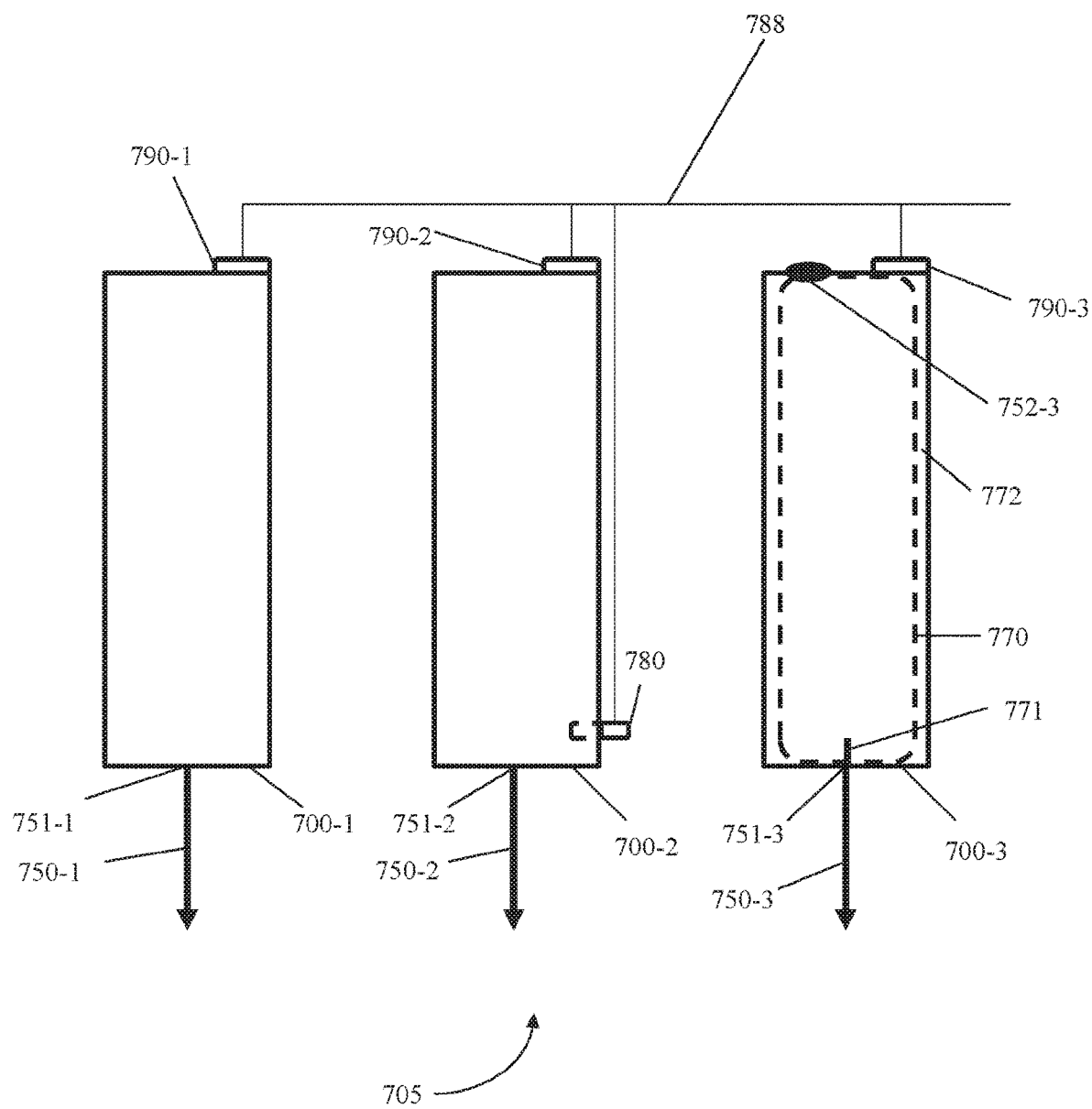
FIG. 29 illustrates an embodiment of at least one cartridge.

FIG. 29 illustrates a reagent cartridge 700 having an authentication device 790 attached to reagent cartridge 700. Cartridge 700 can be part of a system 705 having a plurality of reagent cartridges 700 (700-1, 700-2, and 700-3). Part of system 705, authentication device 790, in one embodiment, can be connected to a network 788 (e.g., network 2810, network 2850, etc.), which can be wired or wireless.

Figure 30:
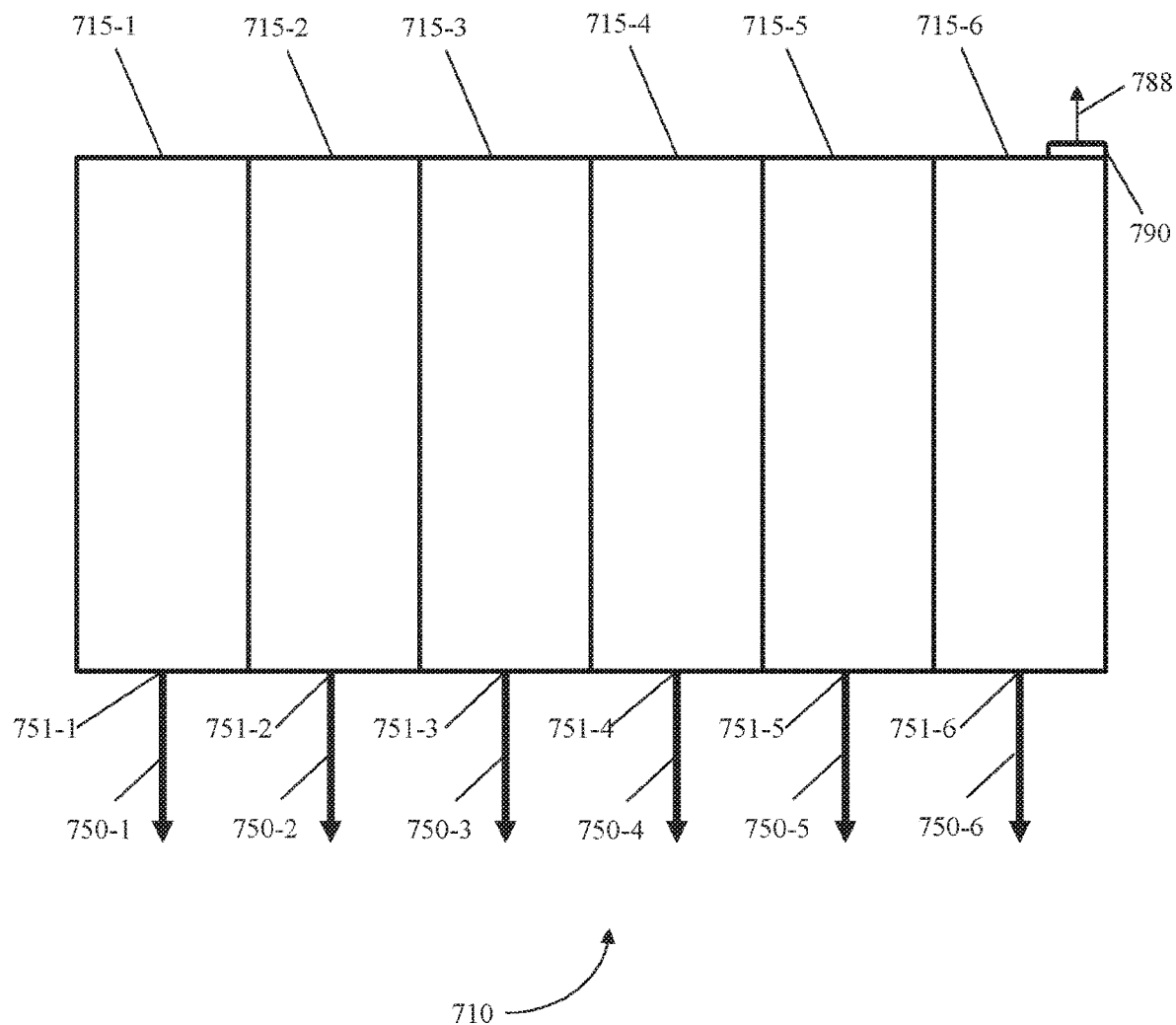
FIG. 30 illustrates an embodiment of a cartridge with a plurality of chambers.

FIG. 30 illustrates cartridge 710 having a plurality of chambers 715 (715-1, 715-2, 715-3, 715-4, 715-5, 715-6). While illustrated with six chambers 715, there could be any number of 2 or greater in cartridge 710.

Figure 31:
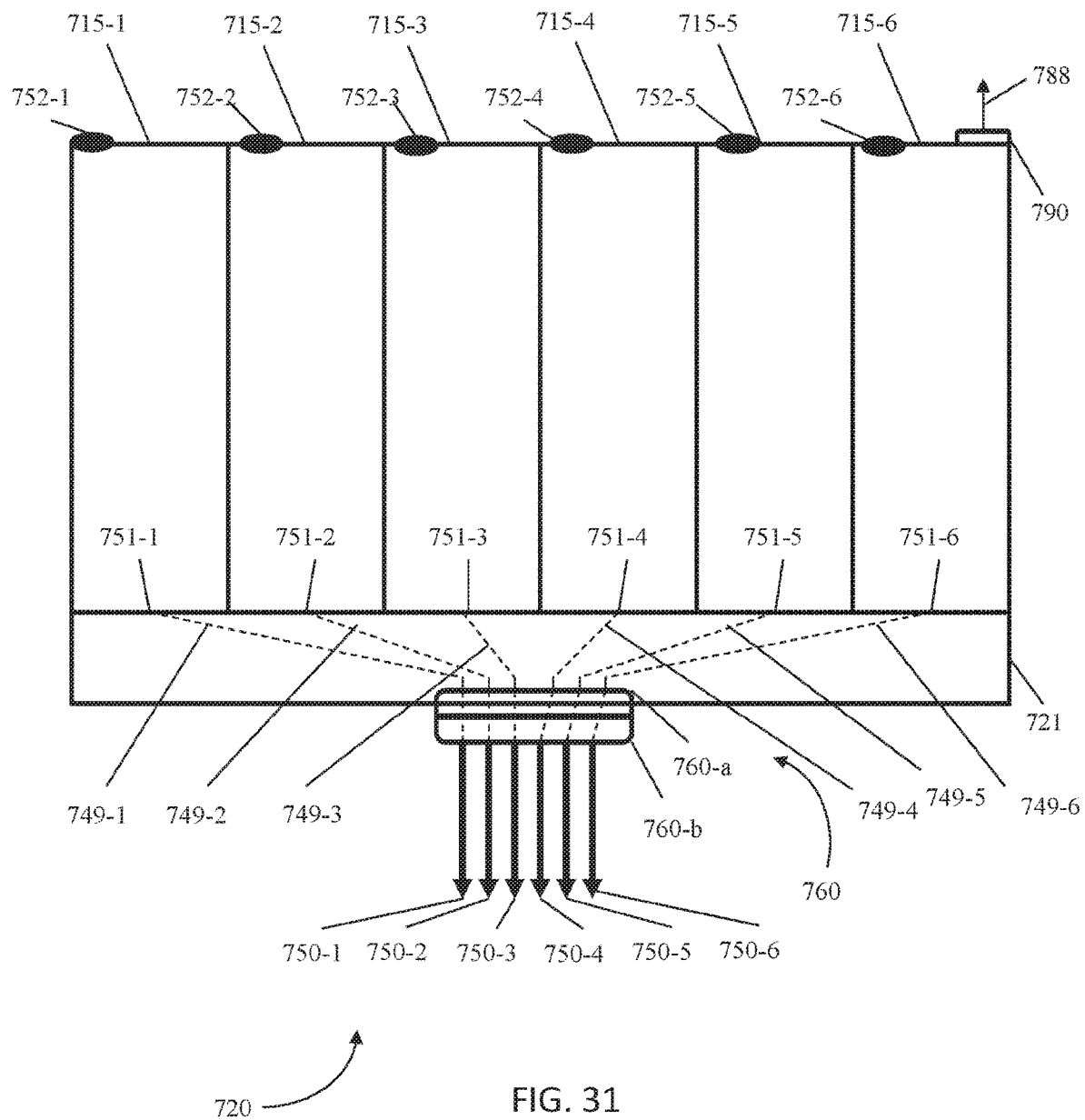
FIG. 31 illustrates an embodiment of a cartridge with a plurality of chambers having a connection.

FIG. 31 illustrates cartridge 720 having a plurality of chambers 715 (715-1, 715-2, 715-3, 715-4, 715-5, 715-6), which can be similar to cartridge 710. Cartridge 720 has a connector 760 having a first portion 760-a and a second portion 760-b that can connect and disconnect from first portion 760-a.

Cartridge 700 (700-1, 700-2, and 700-3) or chamber 715 has at least one opening 751 (751-1, 751-2, 751-3) for filling or dispensing from cartridge 700 or chamber 715. Optionally, a separate inlet 752 can be provided, which is illustrated in FIG. 29 with cartridge 700 having inlet 752-3. In FIGS. 29 and 30, a fluid line 750 (750-1, 750-2, 750-3, 750-4, 750-5, 750-6) is connected to each opening 751 (751-1, 751-2, 751-3, 751-4, 751-5, 751-6), respectively. Fluid line 750 transfers fluid from cartridge 700 or chamber 715 to a test apparatus (not shown), which uses a reagent to test a sample material. In FIG. 31, a transfer line 749 (749-1, 749-2, 749-3, 749-4, 749-5, 749-6) connects each opening 751 (751-1, 751-2, 751-3, 751-4, 751-5, 751-6) to first portion 760-a. When first portion 760-a is connected to second portion 760-b, transfer line 749 (749-1, 749-2, 749-3, 749-4, 749-5, 749-6) is in fluid communication with fluid line 750 (750-1, 750-2, 750-3, 750-4, 750-5, 750-6), respectively. While illustrated with inlet 752 (752-1, 752-2, 752-3, 752-4, 752-5, 752-6) in cartridge 720, inlet 752 is not necessary, and chambers 715 can be filled via transfer line 749 (749-1, 749-2, 749-3, 749-4, 749-5, 749-6). Also illustrated in FIG. 31 is a compartment 721 on cartridge 720 for housing transfer line 749 (749-1, 749-2, 749-3, 749-4, 749-5, 749-6) and to which first portion 760-a is disposed.

FIGS. 30 and 31 illustrate an embodiment in which authentication device 790 is in signal communication with a network 788 (e.g., network 2810, network 2850, etc.).

Authentication of the cartridge 700, 710, 720 can be based on checking for and confirming an identifier on authentication device 790 to ensure that cartridge 700, 710, 720 is an authorized cartridge having the specified reagent. If the cartridge 700, 710, 720 is not authorized, processing system 2820 will not allow testing using cartridge 700, 710, 720.

As illustrated, authentication device can be a chip, such as the chip in an EMV credit card. In other embodiments, authentication device 790 can be an RFID (radio frequency identification) tag, a NFC (nearfield communication) system, a bar code, a QR code, an ink that reflects a specific wavelength of light that is detected by a light detector, or a magnetic emitting/receiving coil. Examples of authentication systems can be found in U.S. Patent Publications US2017/0134610; US2013/0206653; US2007/0127936; US20040158742; US2018/0032776; US2017/0215632; US2015/0185160; US2012/0098526; US2012/0260805; US2012/0255448; US2010/0132564; US2012/0097041; US2012/0100264; US2014/0134299; US2014/0340078; US2013/0043304; US2013/0095214; US2017/0355514; US2017/0347831; International Publication Nos. WO2013174789; WO201315091; WO201780281; WO201806265; European Patent Publication No. EP2578119; and Chinese Patent Publication No. CN105398224.

Checking for and confirming the identifier on device 790 can be done locally by processing system 2820. In another embodiment, the authentication can be done through network interface 2815 to a remote computer (not shown). In another embodiment, authentication can be through an RFID tag.

In one embodiment, authentication device 790 can be a device that can be written to in addition to being read, such as a chip or and RFID tag. There may be times when cartridge 700, 710, 720 is in an analysis system that is used on a first implement, such as a planter, during one time of the season. The analysis system could be moved to a second implement, such as a combine harvester, during a second time of the season. Each of the first implement and the second implement could have a separate processing system 2820. Writing an authentication to the authentication device 790 allows the analysis system with cartridge 700, 710, 720 to be moved between implements.

To ensure that cartridge 700, 710, 720 only contains the correct reagent, authentication can further include measuring an amount of usage of the correct reagent. When the reagent remaining in 700, 710, 720 is less than an amount needed for a test, cartridge 700, 710, 720 can be deauthorized so that cartridge 700, 710, 720 will no longer work. Once deauthorized, cartridge 700, 710, 720 can be removed and sent to an authorized refiller to ensure the correct reagent is added to cartridge 700, 710, 720. After refilling, cartridge 700, 710, 720 can be reset to authorized.

One method for determining the amount of reagent in cartridge 700, 710, 720 is to count the number of uses of the reagent from cartridge 700, 710, 720. The amount of reagent in cartridge in new or refilled condition is known from filling. The amount used in one test is also known. By counting the number of tests, the consumed volume of the reagent is known. Each time a test is run, a count can be stored in memory 2805 or in any memory, whether it is on the implement, or on a remote computer. In one example, a cartridge further includes a counter to count a number of times reagent is dispensed from the cartridge. In another example, a cartridge further includes a time counter. Another method is to measure the amount of reagent dispensed from cartridge 700, 710, 720 through a meter (not shown). The meter can be disposed anywhere between cartridge 700, 710, 720 and the chemical test. The meter can measure either mass or volume. The meter is in signal communication with a network (e.g., network 2810, network 2850, etc.) to communicate the amount of reagent dispensed from cartridge 700, 710, 720. The cartridge information (e.g., amount of reagent dispensed from a cartridge, any information from the cartridge, reagent information) can be communicated to any device that communicates with the network (e.g., network 2810, network 2850, etc.). As above, the amount can be stored in memory 2805 or in any memory, whether it is on the implement, or on a remote computer. In another method, an amount of time can be measured that a pump runs. The pump transfers the reagent from the cartridge 700, 710, 720 to the chemical test. When operated at a constant flow rate, the amount of time that the pump runs will provide the amount of reagent. The pump is in signal communication with a network (e.g., network 2810, network 2850, etc.) to communicate the amount of reagent dispensed from cartridge 700, 710, 720. As above, the amount of time or amount of reagent can be stored in memory 2805 or in any memory, whether it is on the implement, or on a remote computer. In another embodiment, an amount of time since cartridge 700, 710, 720 is installed on a sampling apparatus or a machine can be measured and stored in memory 2805 or in any memory, whether it is on the implement, or on a remote computer. For reagents that may have a shelf life, the cartridge 700, 710, 720 can be deactivated after expiration of the reagent. In another embodiment, a level sensor 780 can measure the level of reagent in cartridge 700 or chamber 715. Level sensor 780 is in signal communication with a network (e.g., network 2810, network 2850, etc.) to communicate the amount of reagent remaining. This amount can be stored in memory 2805 or in any memory, whether it is on the implement, or on a remote computer. Level sensor 780 can be any sensor that measures a level. Examples of level sensors include, but are not limited to, capacitive, mass, ultrasonic, and visual level gauge.

The reagent can be any chemical composition that is used in a chemical analysis to test a sample material for the presence of a chemical in the sample material. Examples of reagents include, but are not limited to, reagents to test for one or more of nitrogen, phosphorous, potassium, boron, magnesium, calcium, zinc, manganese, copper, sulfur, sodium, organic matter, pH, and plant nutrients. The reagents can be used in a colorimetric and/or turbidimetric analysis.

One or more cartridges 700 or chambers 715 can contain water, such as deionized water, to be used as a control fluid or as a flush. Again, the quality of the water can be controlled as above with the reagent to ensure that the water is of the correct quality to be used in tests.

In another embodiment, cartridge 700 or chamber 715 can further include a bag 770 to contain the reagent and isolate the reagent from the atmosphere. When used in a field, there can be dust that is generated as the implement is driven across the field. As reagent is removed from cartridge 700 or chamber 715, a vacuum can be generated. To relief the vacuum to allow reagent to be removed, air can be allowed to enter cartridge 700 or chamber 715. FIG. 29 illustrates cartridge 700-3 having bag 770 with nozzle 771, which is in fluid communication with fluid line 750-3. Inlet 752 can allow air to enter chamber 700-3 as vacuum is created by reagent being removed. Bag 770 isolates the reagent from the air to prevent the reagent from reacting with the air or being contaminated by any dust. The bag 770 can be collapsible. Also, the bag 770 can be impermeable to gas and liquids. This keeps the reagent separated from any gas or liquid that can degrade the reagent. Instead of allowing air in to replace the volume of reagent dispensed, cartridge 700 or chamber 715 can contain a fluid 772, such as gas or liquid, around the bag 770. Fluid 772 can be pressurized such that no vacuum is realized in bag 770 as reagent is dispensed. Fluid 772 can be an inert gas other than air or oxygen. Examples of inert gas include, but are not limited to, nitrogen, argon, or helium.

Figure 32:
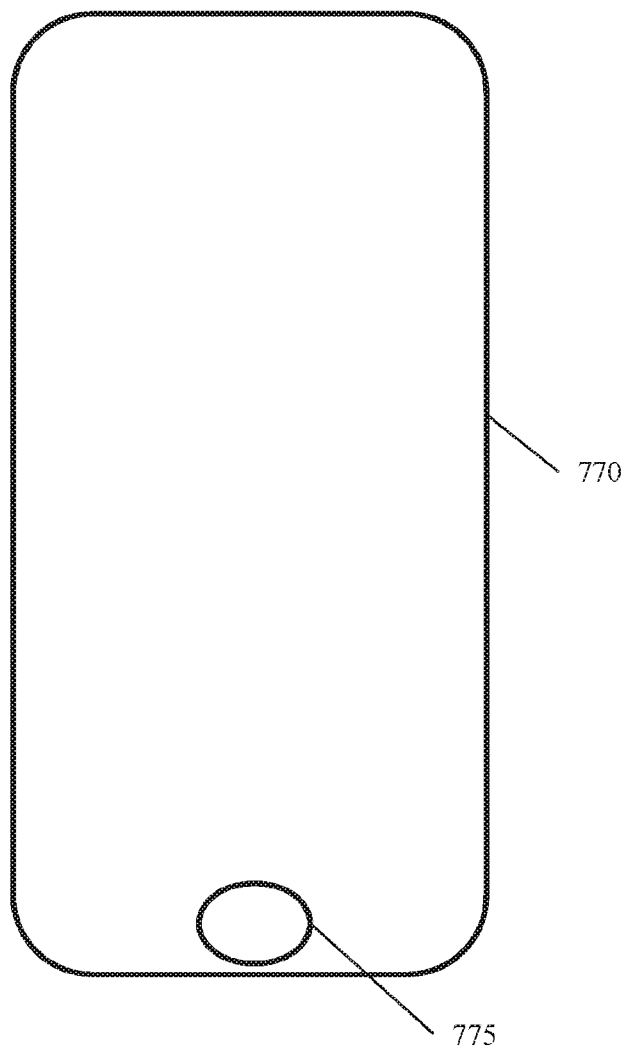
FIG. 32 illustrates a bag with a seal in accordance with an embodiment.

In another embodiment, bag 770 can be one time use bag. Illustrated in FIG. 32, bag 770 has a seal 775. In this embodiment, when bag 770 is punctured, bag 770 does not self seal. Seal 775 can be punctured by nozzle 771 and maintain a seal around nozzle 771, but when nozzle 771 is removed, seal 775 is not resealable. This can be used to prevent incorrect reagents from being refilled into bag 770.

Cartridge 700 or chamber 715 can be sealed. When connected to line 750, cartridge 700 or chamber 715 can be punctured with a connector. As an example as seen in FIG. 29, nozzle 771 can puncture cartridge 700-3 and bag 770 to provide fluid communication for the reagent to fluid line 750-3. In general, when connecting line 750 to cartridge 700 or chamber 715, any type of fitting can be used. Examples of fittings include, but are not limited to, spring loaded check valve, push to connect fittings, and threaded fittings.

In another embodiment, cartridge 700, 710, 720 can further contain insulation to control the temperature of cartridge 700, 710, 720. In addition to or in place of the insulation, resistive heaters can be place around cartridge 700, 710, 720.

In another embodiment, with opening 751 being at the bottom, cartridge 700 or chamber 715 has height to width ratio of at least 1:1. In other embodiments, the height to width ratio is at least 1.1:1, 1.2:1, 1.3:1, 1.4:1, 1.5:1, 2:1, 3:1, 4:1, 5:1, or any number greater than 1:1.

In one embodiment, cartridge 700, 710, 720, can be used in the soil/vegetation analysis system as described above, which is also described in U.S. Application No. 62/418,630, filed on 7 Nov. 2016.

Any of the following examples can be combined into a single embodiment or these examples can be separate embodiments. In one example of a first embodiment, cartridge comprises at least one compartment and a reagent in the at least one compartment. The reagent is a chemical composition for testing at least one of soil and vegetation for a chemical contained in the soil or vegetation. The cartridge is adapted to cooperate with a soil and/or vegetation analysis system to supply the reagent to the soil and/or vegetation analysis system.

In another example of the first embodiment, the cartridge further comprises an authentication device.

In another example of the first embodiment, the authentication device comprises a chip adapted to be connected to a network. When connected to the network, the authentication chip is accessed by the network to confirm that the cartridge is an authorized cartridge containing the reagent that is specific for a soil and/or vegetation test.

In another example of the first embodiment, the cartridge further comprises a meter to measure an amount of reagent dispensed from the cartridge.

In another example of the first embodiment, the meter to communicate the amount of the reagent dispensed from the cartridge to a network.

In another example of the first embodiment, the cartridge further comprises a counter to count a number of times reagent is dispensed from the cartridge to determine consumed volume of reagent.

In another example of the first embodiment, the cartridge further comprises a time counter to count time for determining an amount of reagent dispensed from the cartridge.

In another example of the first embodiment, the cartridge further comprises a level sensor to measure a level of reagent in the cartridge.

In another example of the first embodiment, the level sensor to communicate with a network to communicate the level of the reagent in the cartridge.

In another example of the first embodiment, the cartridge further comprises a bag having a nozzle. During operation of the cartridge the bag to contain the reagent and isolate the reagent from an atmosphere. The nozzle is in fluid communication with the fluid line.

In another example of the first embodiment, the cartridge further comprises an inlet to allow air to enter the cartridge as vacuum is created by reagent being removed from the bag.

In another example of the first embodiment, the cartridge further comprises a fluid to surround the bag with the fluid being pressurized to prevent a vacuum being created when reagent is removed from the bag.

In another example of the first embodiment, the bag is one time use bag having a seal. The seal is capable of being punctured by the nozzle and maintaining a seal around nozzle. When the nozzle is removed, seal is not resealable to prevent incorrect reagents from being refilled into the bag.

In another example of the first embodiment, the cartridge further comprises insulation to control a temperature of the cartridge.

In another example of the first embodiment, the cartridge further comprises an opening of the cartridge that is in fluid communication with a fluid line to transfer fluid from the cartridge to a test apparatus.

In another example of the first embodiment, the opening is positioned at a bottom of the cartridge and the cartridge has a height to width ratio of at least 1:1.

In another example of the first embodiment, a height to width ratio of the cartridge is at least 1.1:1, 1.2:1, 1.3:1, 1.4:1, 1.5:1, 2:1, 3:1, 4:1, 5:1, or any number greater than 1:1.

In another example of the first embodiment, an amount of time since the cartridge is installed on a sampling implement or machine is measured and stored in a memory.

In another example of the first embodiment, the cartridge comprises an analysis system to perform a first analysis with the cartridge being on a first implement during a first time of a planting season and then moved to a second different implement during a second time of a harvesting season to perform a second analysis.

In one example of a second embodiment, a multichamber cartridge comprises a body, a plurality of chambers in the body, each chamber having a fluid line in fluid communication with the chamber. The multichamber cartridge is adapted to cooperate with a soil and/or vegetation analysis system to supply a reagent from at least one of the chambers to the soil and/or vegetation analysis system.

In another example of the second embodiment, the multichamber cartridge further comprises an authentication device.

In another example of the second embodiment, the authentication device comprises a chip adapted to be connected to a network. When connected to the network, the authentication chip is accessed by the network to confirm that the multichamber cartridge is an authorized cartridge containing the reagent that is specific for a soil and/or vegetation test.

In another example of the second embodiment, the authentication device to deauthorize at least one chamber or deauthorize the multichamber cartridge when at least one chamber has less than an amount of reagent needed for a test analysis.

In another example of the second embodiment, the body further comprises a connector, and each fluid line is connected to the connector.

In another example of the second embodiment, the connector comprises a first portion and a second portion that is capable of connecting and disconnecting from the first portion.

In another example of the second embodiment, each chamber comprises an opening in fluid communication with the first portion.

In another example of the second embodiment, the multichamber cartridge further comprises a plurality of transfer lines with each transfer line in fluid communication with one of the openings and the first portion.

In another example of the second embodiment, each transfer line is in fluid communication with a corresponding fluid line when the first portion is connected to the second portion.

In another example of the second embodiment, each chamber is filled via a transfer line and one of the openings.

In another example of the second embodiment, each chamber comprises an inlet for filling each chamber with a fluid.

What is claimed is:

1. A cartridge comprising:
    at least one compartment;
    a reagent in the at least one compartment, wherein the reagent is a chemical composition for testing at least one of soil and vegetation for a chemical contained in the soil or vegetation;
    a readable writable authentication device to authenticate the cartridge as an authorized cartridge containing the reagent; and
    wherein the cartridge is adapted to cooperate with a soil and/or vegetation analysis system to supply the reagent to the soil and/or vegetation analysis system.

2. The cartridge of claim 1, wherein the cartridge is capable of being deactivated after expiration of the reagent.

3. The cartridge of claim 1, wherein the readable writeable authentication device comprises a chip adapted to be connected to a network, wherein when connected to the network, the readable writeable authentication chip is accessed by the network to confirm that the cartridge is an authorized cartridge containing the reagent that is specific for a soil and/or vegetation test.

4. The cartridge of claim 1 further comprising a meter to measure an amount of reagent dispensed from the cartridge, wherein the meter communicates the amount of reagent dispensed from the cartridge to a network, wherein authentication of the cartridge further includes determining an amount of usage of the reagent.

5. The cartridge of claim 1 further comprising a counter to count a number of times reagent is dispensed from the cartridge to determine consumed volume of reagent, wherein the counter communicates with a network to communicate the number of times.

6. The cartridge of claim 1 further comprising a time counter to count time for determining an amount of reagent dispensed from the cartridge, wherein the time counter communicates with a network to communicate the amount of time.

7. The cartridge of claim 1, further comprising a level sensor to measure a level of reagent in the cartridge, wherein the level sensor communicates with a network to communicate the level of reagent in the cartridge.

8. The cartridge of claim 1 further comprising a bag having a nozzle, during operation of the cartridge the bag to contain the reagent and isolate the reagent from an atmosphere, wherein the nozzle is in fluid communication with a fluid line.

9. The cartridge of claim 8 further comprising an inlet to allow air to enter the cartridge as vacuum is created by reagent being removed from the bag.

10. The cartridge of claim 8 further comprising a fluid to surround the bag with the fluid being pressurized to prevent a vacuum being created when reagent is removed from the bag.

11. The cartridge of claim 8, wherein the bag is one time use bag having a seal, wherein the seal is capable of being punctured by the nozzle and maintaining a seal around nozzle, wherein when the nozzle is removed, seal is not resealable to prevent incorrect reagents from being refilled into the bag.

12. The cartridge of claim 1 further comprising insulation to control a temperature of cartridge.

13. The cartridge of claim 1 further comprising an opening of the cartridge that is in fluid communication with a fluid line to transfer fluid from the cartridge to a test apparatus.

14. The cartridge of claim 13, wherein the opening is positioned at a bottom of the cartridge, wherein the cartridge has a height to width ratio of at least 1:1.

15. The cartridge of claim 13, wherein, a height to width ratio of the cartridge is at least 1.1:1, 1.2:1, 1.3:1, 1.4:1, 1.5:1, 2:1, 3:1, 4:1, 5:1, or any number greater than 1:1.

16. The cartridge of claim 1, wherein an amount of time since the cartridge is installed on a sampling implement or machine is measured and stored in a memory.

17. The cartridge of claim 1, wherein the cartridge comprises an analysis system to perform a first analysis with the cartridge being on a first implement during a first time of a planting season and then moved to a second different implement during a second time of a harvesting season to perform a second analysis.

18. A sampling system comprising:
    a vehicle for traversing a field;
    a collection system disposed on the vehicle for collecting a sample chosen from a soil sample, a vegetation sample, or soil and vegetation samples from the field;
    a testing system for testing the sample;
    wherein the cartridge of claim 1 supplies at least one reagent to the testing system.

19. A multichamber cartridge comprising:
    a body;
    a plurality of chambers in the body,
    each chamber having a fluid line in fluid communication with the chamber;
    a readable writable authentication device to authenticate the multichamber cartridge as an authorized multichamber cartridge containing a specified reagent; and
    wherein the multichamber cartridge is adapted to cooperate with a soil and/or vegetation analysis system to supply the specified reagent from at least one of the chambers to the soil and/or vegetation analysis system.

20. The multichamber cartridge of claim 19, wherein writing an authentication to the readable writable authentication device allows the soil and/or vegetation analysis system with the multichamber cartridge to be moved between a first agricultural implement and a second agricultural implement.

21. The multichamber cartridge of claim 19, wherein the readable writable authentication device comprises a chip adapted to be connected to a network, wherein when connected to the network, the readable writable authentication chip is accessed by the network to confirm that the multichamber cartridge is an authorized cartridge containing the specified reagent that is specific for a soil and/or vegetation test.

22. The multichamber cartridge of claim 19, wherein the readable writable authentication device to deauthorize at least one chamber or deauthorize the multichamber cartridge when at least one chamber has less than an amount of reagent needed for a test analysis.

23. The multichamber cartridge of claim 19, wherein the body further comprises a connector, and wherein each fluid line is connected to the connector.

24. The multichamber cartridge of claim 19, wherein the connector comprises:
    a first portion; and
    a second portion that is capable of connecting and disconnecting from the first portion.

25. The multichamber cartridge of claim 24, wherein each chamber comprises an opening in fluid communication with the first portion.

26. The multichamber cartridge of claim 25, further comprises a plurality of transfer lines with each transfer line in fluid communication with one of the openings and the first portion.

27. The multichamber cartridge of claim 26, wherein each transfer line is in fluid communication with a corresponding fluid line when the first portion is connected to the second portion.

28. The multichamber cartridge of claim 25, wherein each chamber is filled via a transfer line and one of the openings.

29. The multichamber cartridge of claim 25, wherein each chamber comprises an inlet for filling each chamber with a fluid.

30. A sampling system comprising:
a vehicle for traversing a field;
a collection system disposed on the vehicle for collecting a sample chosen from a soil sample, a vegetation sample, or soil and vegetation samples from the field;
a testing system for testing the sample;
wherein the multichamber cartridge of claim 19 supplies at least one reagent to the testing system.

* * * * *